United States Patent [19]
Duplantier et al.

[11] Patent Number: 5,814,651
[45] Date of Patent: Sep. 29, 1998

[54] CATECHOL DIETHERS AS SELECTIVE PDE$^{IV}$ INHIBITORS

[75] Inventors: Allen Jacob Duplantier, Ledyard; James Frederick Eggler, Stonington; Anthony Marfat, Mystic; Hiroko Masamune, Noank, all of Conn.

[73] Assignee: Pfizer Inc., New York, N.Y.

[21] Appl. No.: 872,686

[22] Filed: Jun. 10, 1997

Related U.S. Application Data

[60] Division of Ser. No. 142,328, Nov. 26, 1993, abandoned, which is a continuation-in-part of Ser. No. 984,408, Dec. 2, 1992, abandoned.

[51] Int. Cl.$^6$ ........................ A61K 31/415; C07D 235/06
[52] U.S. Cl. .................... 514/394; 548/268.6; 548/267.8
[58] Field of Search ............................. 548/268.6, 267.8; 514/394

[56] References Cited

U.S. PATENT DOCUMENTS

| | | | |
|---|---|---|---|
| 5,430,062 | 7/1995 | Cushman | 514/646 |
| 5,449,687 | 9/1995 | Christensen, IV et al. | 514/520 |
| 5,622,977 | 4/1997 | Warrellow | 514/336 |

FOREIGN PATENT DOCUMENTS

| | | |
|---|---|---|
| 0247725 | 12/1987 | European Pat. Off. . |
| 0401903 | 12/1990 | European Pat. Off. . |
| 0428302 | 5/1991 | European Pat. Off. . |
| 0428313 | 5/1991 | European Pat. Off. . |
| 0511865 | 11/1992 | European Pat. Off. . |
| 8404521 | 11/1984 | WIPO . |
| 8706576 | 11/1987 | WIPO . |
| 9107178 | 5/1991 | WIPO . |
| 9115451 | 10/1991 | WIPO . |
| 9206085 | 4/1992 | WIPO . |
| 9206963 | 4/1992 | WIPO . |
| 9207567 | 5/1992 | WIPO . |
| 9219594 | 11/1992 | WIPO . |
| 9410118 | 5/1994 | WIPO . |

OTHER PUBLICATIONS

Chemical Abstracts, vol. 117:251066, abstract of EP 497564A1, 1992.
Chemical Abstracts, vol. 115, No. 15, 1991, Abs. No. 158680z.
Chemical Abstracts, vol. 112, No. 19, 1990, Abs. No. 172319h.
Beavo, J. A. et al., TiPS, Apr. 1990, vol. 11, pp. 150–155.
Nicholson, C. D. et al., TiPS, Jan. 1991, vol. 12, pp. 19–27.
Sutherland, E. W. et al., Pharmacol. Rev., 1960, 12, pp. 265–299.
Verghese, M. W. et al., J. Mol. Cell Cadiol., 1989, 12 (Suppl. II), S61.

*Primary Examiner*—John Kight
*Assistant Examiner*—D. Margaret M. Mach
*Attorney, Agent, or Firm*—Peter C. Richardson; Paul H. Ginsburg; Jolene W. Appleman

[57] ABSTRACT

This invention relates to 4-substituted catechol diether compounds which are selective inhibitors of phosphodiesterase (PDE) type IV. The compounds of the present invention are useful in inhibiting PDE$_{IV}$ and in the treatment of AIDS, asthma, bronchitis, chronic obstructive airways disease, psoriasis, allergic rhinitis, dermatitis and other inflammatory diseases. This invention also relates to pharmaceutical compositions comprising the compounds hereof.

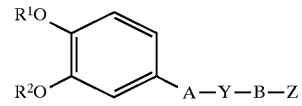

9 Claims, No Drawings

CATECHOL DIETHERS AS SELECTIVE PDE$^{IV}$ INHIBITORS

CROSS REFERENCE TO RELATED APPLICATIONS

This application is a division of application Ser. No. 08/142,328, filed Nov. 26, 1993, now abandoned, which is the national stage of International Application No. PCT/US93/10228 having an International Filing date of Oct. 29, 1993, which is a continuation-in-part of U.S. application Ser. No. 07/984,408 filed Dec. 2, 1992, now abandoned.

BACKGROUND OF THE INVENTION

This invention relates to a series of 4-substituted catechol diether compounds which are selective inhibitors of phosphodiesterase (PDE) type IV and as such are useful in the treatment of AIDS, asthma, arthritis, bronchitis, chronic obstructive airways disease, psoriasis, allergic rhinitis, dermatitis and other inflammatory diseases.

This invention also relates to the pharmaceutically acceptable salts of said compounds; to a method of using such compounds in the treatment of inflammatory conditions in mammals, especially humans; and to pharmaceutical compositions useful therefor.

The "inflammatory conditions" which can be treated according to this invention include, but are not limited to, chronic obstructive pulmonary disease, shock, atopic dermatitis, bronchitis, rheumatoid arthritis and osteoarthritis.

Since the recognition that cyclic AMP is an intracellular second messenger (E. W. Sutherland, and T. W. Rall, *Pharmacol. Rev.*, 1960, 12, 265), inhibition of the phosphodiesterases have been a target for modulation and, accordingly, therapeutic intervention in a range of disease processes. More recently, distinct classes of PDE have been recognized (J. A. Beavo and D. H. Reifsnyder, *TIPS*, 1990, 11, 150), and their selective inhibition has led to improved drug therapy (C. D. Nicholson, R. A. Challiss and M. Shahid, *TIPS*, 1991, 12, 19). More particularly, it has been recognized that inhibition of PDE type IV can lead to inhibition of inflammatory mediator release (M. W. Verghese et al., *J. Mol. Cell Cardiol.*, 1989, 12 (Suppl. II), S 61) and airway smooth muscle relaxation (T. J. Torphy in *Directions for New Anti-Asthma Drugs*, eds S. R. O'Donnell and C. G. A. Persson, 1988, 37, Birkhauser-Verlag). Thus, compounds that inhibit PDE type IV, but which have poor activity against other PDE types, would inhibit the release of inflammatory mediators and relax airway smooth muscle without causing cardiovascular effects or antiplatelet effects.

Certain pyrimidone compounds have been disclosed to be useful as antidepressants by Saccomano et al., in European Patent Application EPO 247 725 A2. The same pyrimidone compounds have been disclosed to be useful against asthma and certain skin disorders in International Patent Application No. PCT/US90/02162, filed Apr. 20, 1990.

SUMMARY OF THE INVENTION

This invention is concerned with a series of 4-substituted catechol diether compounds and to the pharmaceutically acceptable salts of such compounds. These new compounds possess antiinflammatory activity in mammals, especially humans.

The compounds of the present invention are of the formula (I)

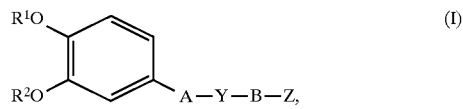

the racemic-diastereomeric mixtures and optical isomers of compounds of formula I and the pharmaceutically acceptable salts thereof wherein $R^1$ is selected from the group consisting of methyl, ethyl, difluoromethyl and trifluoromethyl;

$R^2$ is selected from the group consisting of $(C_1-C_6)$alkyl, alkoxyalkyl having 3 to 7 carbons in the alkoxy portion and 2 to 4 carbons in the alkyl portion, phenoxyalkyl having 2 to 6 carbons in the alkyl portion, $(C_3-C_7)$ cycloalkyl, $(C_8-C_9)$polycycloalkyl, phenylalkyl having 1 to 8 carbons in the alkyl portion, phenylaminoalkyl having 2 to 6 carbons in the alkyl portion and the amino may be optionally substituted with $(C_1-C_4)$ alkyl and indanyl, where the alkyl portion of said alkyl, phenoxyalkyl, cycloalkyl, polycycloalkyl, phenylalkyl and indanyl may optionally be substituted with one or more fluorine atoms, —OH or $(C_1-C_4)$alkoxy, and the aryl portion of said phenylalkyl, phenoxyalkyl and indanyl may optionally be substituted with $(C_1-C_4)$alkyl, $(C_1-C_4)$alkoxy or halogen;

A and B are independently selected from the group consisting of a covalent bond, optionally substituted $(C_1-C_5)$alkylene, optionally substituted $(C_2-C_5)$ alkenyl and optionally substituted phenylene, where said optionally substituted alkylene may be monosubstituted and each substituent is selected from the group consisting of oxo, $(C_1-C_4)$alkoxy, $CO_2R^6$ and hydroxy, said optionally substituted alkenyl may be monosubstituted with $(C_1-C_4)$alkoxy or $CO_2R^6$, and said optionally substituted phenylene may be monosubstituted with $(C_1-C_4)$ alkoxy, $CO_2R^6$ or hydroxy, wherein $R^6$ is hydrogen or $(C_1-C_4)$alkyl;

Y is selected from the group consisting of a covalent bond, O, $NR^6$ and S wherein $R^6$ is as defined above;

Z is selected from the group consisting of

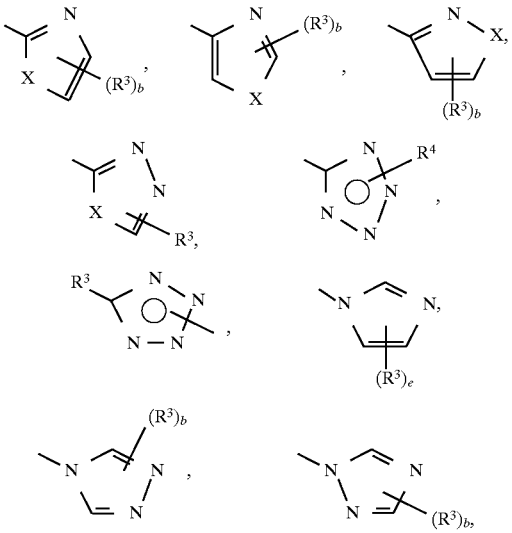

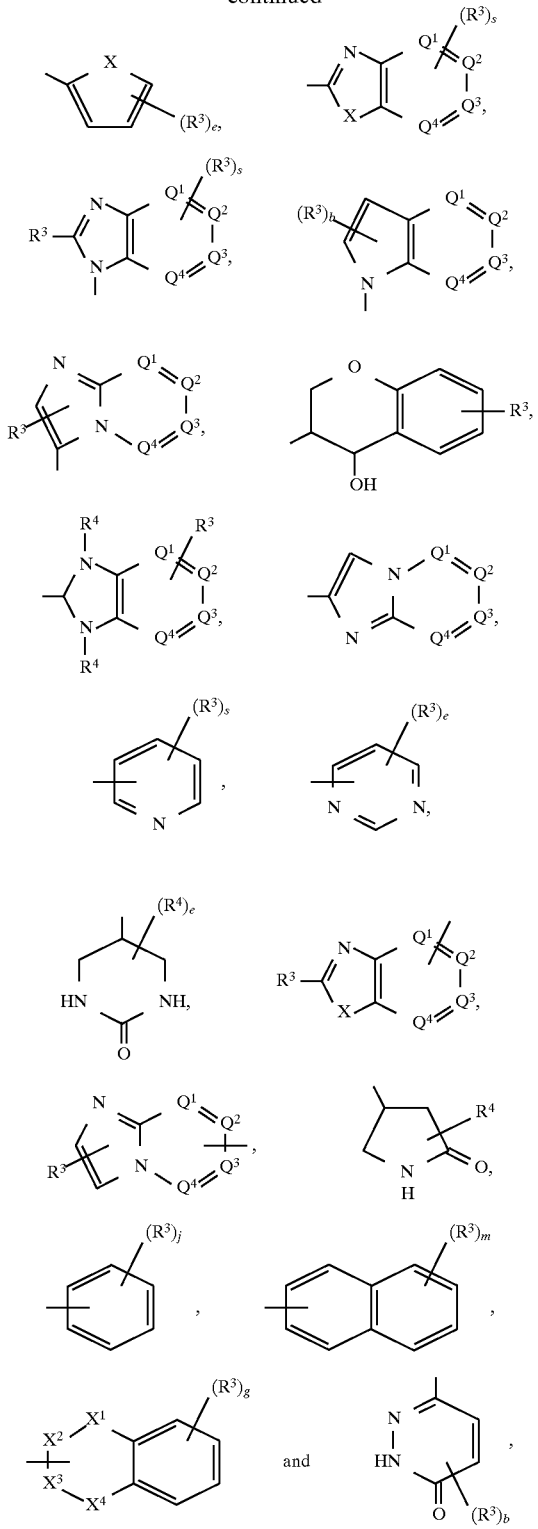

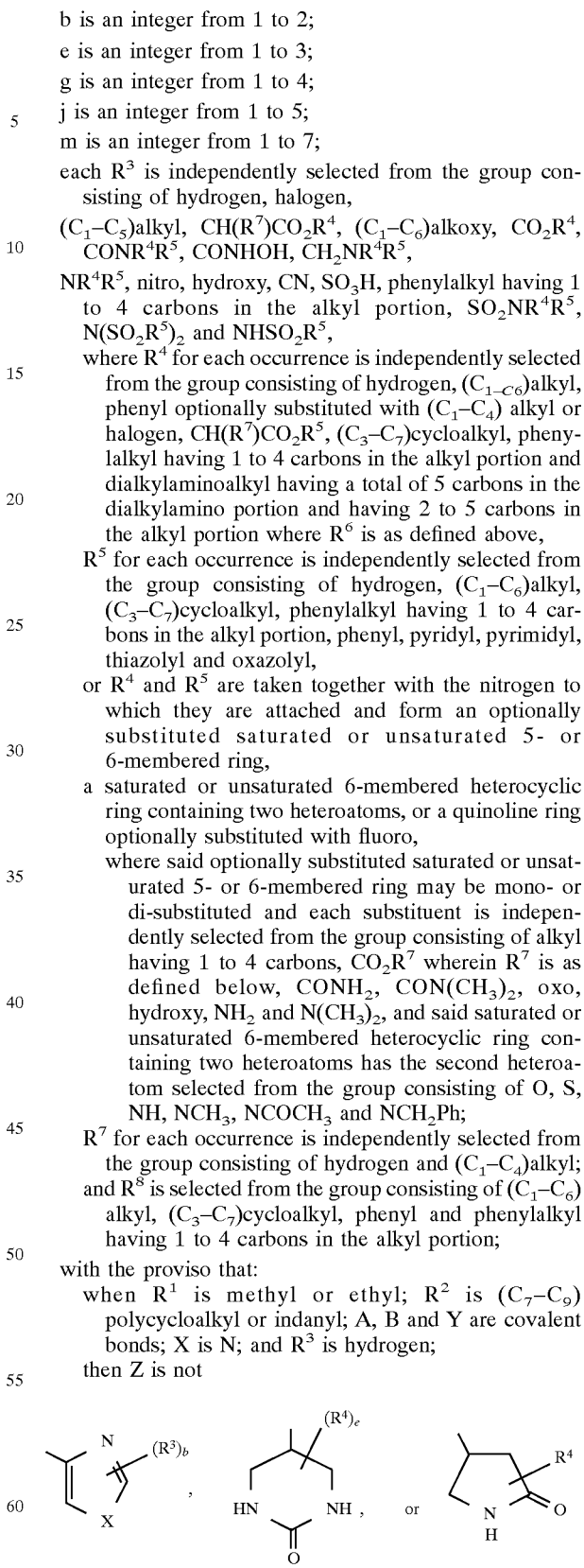

where $Q^1$, $Q^2$, $Q^3$, and $Q^4$ are independently N, CH or, when also bonded to B, C and provided that at least two of $Q^1$, $Q^2$, $Q^3$, and $Q^4$ are not N;

X is selected from the group consisting of O, $NR^4$ and S;

and $X^1$, $X^2$, $X^3$ and $X^4$ are independently selected from the group consisting of O, $NR^4$, S, C=O, $CH_2$ and, when also bonded to B, CH;

b is an integer from 1 to 2;

e is an integer from 1 to 3;

g is an integer from 1 to 4;

j is an integer from 1 to 5;

m is an integer from 1 to 7;

each $R^3$ is independently selected from the group consisting of hydrogen, halogen, $(C_1-C_5)$alkyl, $CH(R^7)CO_2R^4$, $(C_1-C_6)$alkoxy, $CO_2R^4$, $CONR^4R^5$, CONHOH, $CH_2NR^4R^5$, $NR^4R^5$, nitro, hydroxy, CN, $SO_3H$, phenylalkyl having 1 to 4 carbons in the alkyl portion, $SO_2NR^4R^5$, $N(SO_2R^5)_2$ and $NHSO_2R^5$, where $R^4$ for each occurrence is independently selected from the group consisting of hydrogen, $(C_1-C_6)$alkyl, phenyl optionally substituted with $(C_1-C_4)$ alkyl or halogen, $CH(R^7)CO_2R^5$, $(C_3-C_7)$cycloalkyl, phenylalkyl having 1 to 4 carbons in the alkyl portion and dialkylaminoalkyl having a total of 5 carbons in the dialkylamino portion and having 2 to 5 carbons in the alkyl portion where $R^6$ is as defined above, $R^5$ for each occurrence is independently selected from the group consisting of hydrogen, $(C_1-C_6)$alkyl, $(C_3-C_7)$cycloalkyl, phenylalkyl having 1 to 4 carbons in the alkyl portion, phenyl, pyridyl, pyrimidyl, thiazolyl and oxazolyl, or $R^4$ and $R^5$ are taken together with the nitrogen to which they are attached and form an optionally substituted saturated or unsaturated 5- or 6-membered ring, a saturated or unsaturated 6-membered heterocyclic ring containing two heteroatoms, or a quinoline ring optionally substituted with fluoro, where said optionally substituted saturated or unsaturated 5- or 6-membered ring may be mono- or di-substituted and each substituent is independently selected from the group consisting of alkyl having 1 to 4 carbons, $CO_2R^7$ wherein $R^7$ is as defined below, $CONH_2$, $CON(CH_3)_2$, oxo, hydroxy, $NH_2$ and $N(CH_3)_2$, and said saturated or unsaturated 6-membered heterocyclic ring containing two heteroatoms has the second heteroatom selected from the group consisting of O, S, NH, $NCH_3$, $NCOCH_3$ and $NCH_2Ph$;

$R^7$ for each occurrence is independently selected from the group consisting of hydrogen and $(C_1-C_4)$alkyl;

and $R^8$ is selected from the group consisting of $(C_1-C_6)$ alkyl, $(C_3-C_7)$cycloalkyl, phenyl and phenylalkyl having 1 to 4 carbons in the alkyl portion;

with the proviso that:

when $R^1$ is methyl or ethyl; $R^2$ is $(C_7-C_9)$ polycycloalkyl or indanyl; A, B and Y are covalent bonds; X is N; and $R^3$ is hydrogen;

then Z is not and with the further proviso that:

when $R^1$ is methyl or ethyl; $R^2$ is $(C_7-C_9)$polycycloalkyl or indanyl; A, B and Y are covalent bonds; $Q^1$, $Q^2$, $Q^3$, and $Q^4$ are CH or, when bonded to B, C; and $R^3$ is hydrogen;

then Z is not

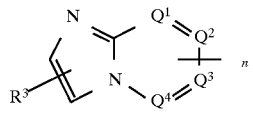

As used throughout this specification and the appendant claims, the terms

"alkyl" and "alkoxy" include both straight chain and branched groups;

the term "halogen" includes fluoro, chloro and bromo; and the symbol "Ph" in the term "NCH$_2$Ph" means phenyl.

Those members of the substituent Z which are bicyclic are attached to the remainder of the compound of formula (I) through the ring of the Z substituent in which the bond is drawn.

As will be readily apparent to one skilled in the art, when Z is either

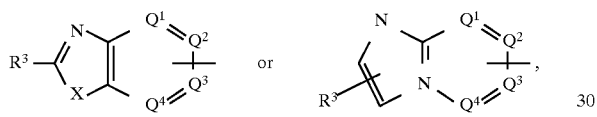

and one or more of $Q^1$, $Q^2$, $Q^3$ and $Q^4$ is N, Z cannot be bonded through one of its ring nitrogen atoms to the rest of the molecule.

Further, it will also be readily apparent to one skilled in the art, when Z is

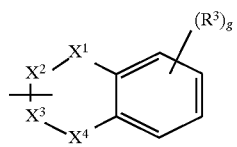

and one or more of $X^1$, $X^2$, $X^3$ and $X^4$ is O, S, C=O or CH$_2$, Z cannot be bonded through one of the above-named atoms or groups to the rest of the molecule.

A preferred group of compounds is that group of compounds of formula (I), above, wherein $R^1$ is selected from the group consisting of methyl and difluoromethyl;

$R^2$ is selected from the group consisting of $(C_3–C_7)$ cycloalkyl, $(C_6–C_9)$polycycloalkyl, phenylalkyl having 1 to 8 carbons in the alkyl portion and phenoxyalkyl having 2 to 6 carbons in the alkyl portion;

A is selected from the group consisting of a covalent bond, $(C_1–C_5)$alkylene and $(C_2–C_5)$alkenyl;

B is selected from the group consisting of a covalent bond, phenylene optionally substituted with $(C_1–C_4)$ alkoxy, $(C_1–C_5)$alkylene and $(C_2–C_5)$alkenyl;

Y is selected from the group consisting of a covalent bond, O and NR$^6$;

Z is selected from the group consisting of

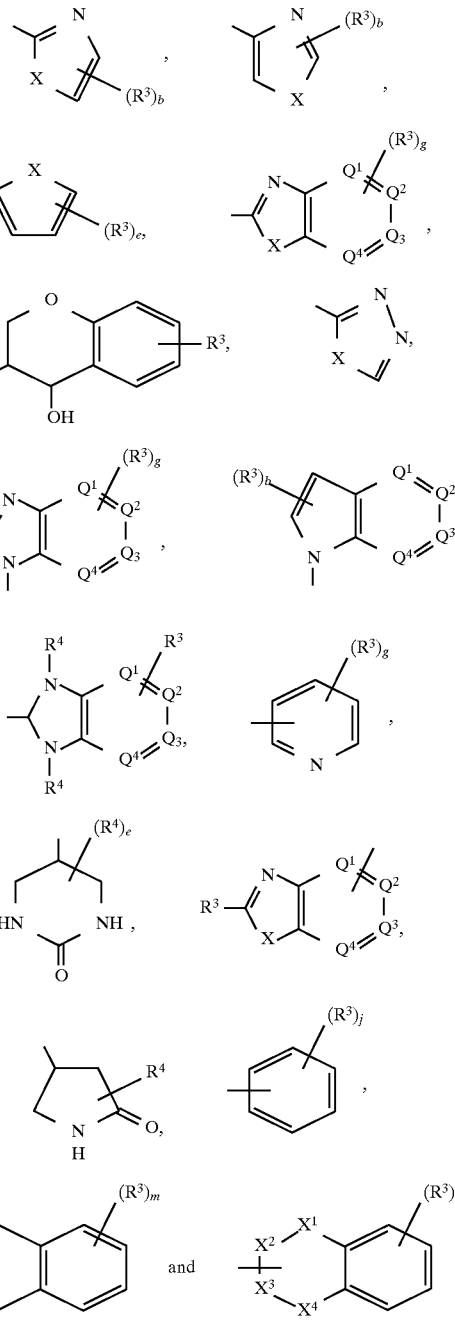

each $R^3$ is independently selected from the group consisting of hydrogen, halogen, $(C_1–C_6)$ alkyl, CH(R$^7$)CO$_2$R$^4$, $(C_1–C_6)$alkoxy, CO$_2$R$^4$, CONR$^4$R$^5$, nitro, hydroxy, N(SO$_2$R$^8$)$_2$ and NHSO$_2$R$^5$, where $R^4$ for each occurrence is independently selected from the group consisting of hydrogen and $(C_1–C_6)$ alkyl, $R^5$ is selected from the group consisting of hydrogen and $(C_1–C_6)$alkyl, and $Q^1$, $Q^2$, $Q^3$, $Q^4$, X, $X^1$, $X^2$, $X^3$, $X^4$, b, e, g, j, m, $R^6$ and $R^8$ are as defined above.

A more preferred group of compounds is that group of compounds of formula (I), above, wherein $R^1$ is selected from the group consisting of methyl and difluoromethyl;

R² is selected from the group consisting of (C₃–C₇)cycloalkyl, (C₆–C₉)polycycloalkyl and phenylalkyl having 1 to 8 carbons in the alkyl portion;

A is selected from the group consisting of a covalent bond and methylene;

B is selected from the group consisting of a covalent bond, methylene and phenylene;

Y is selected from the group consisting of a covalent bond and O;

Z is selected from the group consisting of

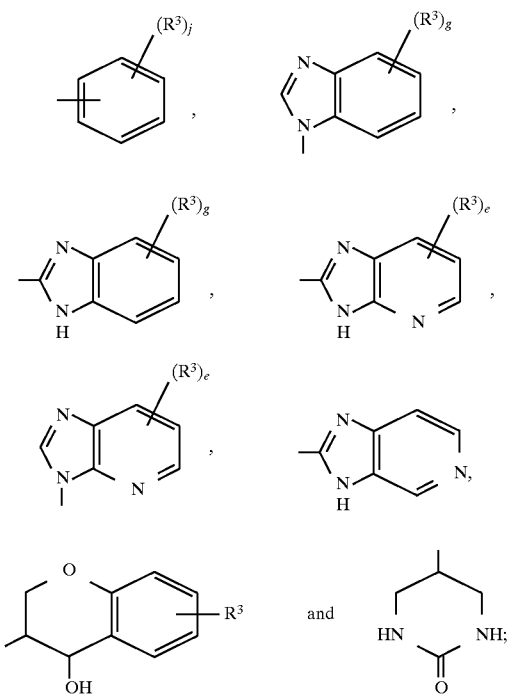

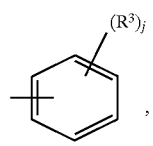 and where R³, e, g and j are as defined above.

Another group of preferred compounds is that group of compounds of formula (I), above, wherein R¹ is selected from the group consisting of methyl and difluoromethyl; R² is selected from the group consisting of (C₃–C₇)cycloalkyl, (C₆–C₉)polycycloalkyl and phenylalkyl having 1 to 8 carbons in the alkyl portion; A, B and Y are a covalent bond; and Z is

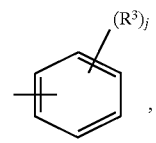

wherein R³ and j are as defined above for formula (I).

Another group of preferred compounds is that group of compounds of formula (I), above, wherein R¹ is selected from the group consisting of methyl and difluoromethyl; R² is selected from the group consisting of (C₃–C₇)cycloalkyl, (C₆–C₉)polycycloalkyl and phenylalkyl having 1 to 8 carbons in the alkyl portion; A, B and Y are a covalent bond; and Z is selected from the group consisting of

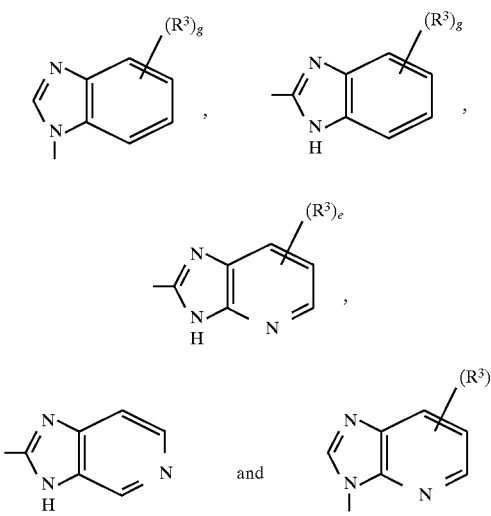

wherein R³, g and e are as defined above for formula (I).

Yet still another group of preferred compounds is that group of compounds of formula (I), above, wherein R¹ is selected from the group consisting of methyl and difluoromethyl; R² is selected from the group consisting of (C₃–C₇)cycloalkyl, (C₆–C₉)polycycloalkyl and phenylalkyl having 1 to 8 carbons in the alkyl portion; A is methylene; B is a covalent bond; Y is O; and Z is

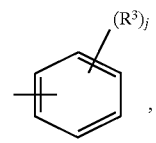

wherein R³ and j are as defined above for formula (I).

Further, another group of preferred compounds is that group of compounds of formula (I), above, wherein R¹ is selected from the group consisting of methyl and difluoromethyl; R² is selected from the group consisting of (C₃–C₇)cycloalkyl, (C₆–C₉)polycycloalkyl and phenylalkyl having 1 to 8 carbons in the alkyl portion; A is methylene; B and Y are a covalent bond; and Z is

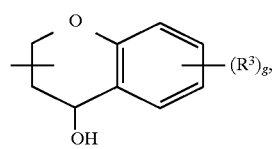

wherein R³ and g are as defined above for formula (I).

Furthermore, another group of preferred compounds is that group of compounds of formula (I), above, wherein R¹ is selected from the group consisting of methyl and difluoromethyl; R² is selected from the group consisting of (C₃–C₇)cycloalkyl, (C₆–C₉)polycycloalkyl, phenylalkyl having 1 to 8 carbons in the alkyl portion and phenoxyalkyl having 2 to 6 carbons in the alkyl portion; A is methylene; B is phenylene; Y is O and Z is selected from the group consisting of

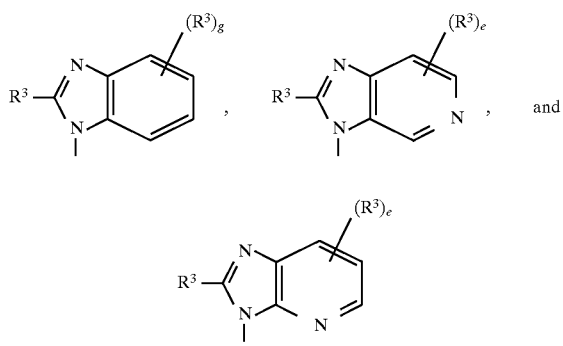

wherein $R^3$, g and e are as defined above for formula (I).

The starting materials and reagents required for the synthesis of the compounds of the present invention are readily available, either commercially, according to literature methods, or by methods exemplified in Preparations below.

DETAILED DESCRIPTION OF THE INVENTION

The compounds of the invention can be prepared by a number of different processes according to the invention.

(a) In one process certain compounds of the formula (IV) can be prepared by the Wittig synthesis, according to the following reaction scheme:

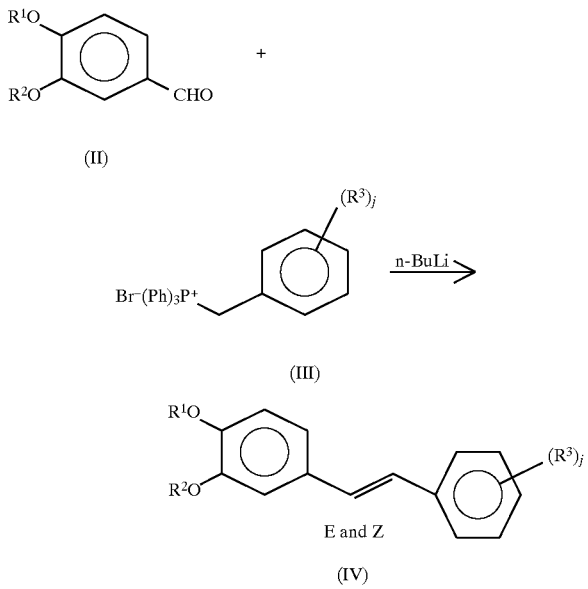

wherein $R^1$, $R^2$, $R^3$ and j are as defined above for formula (I).

In a typical procedure, approximately one equivalent of the phenylphosphonium bromide (III), dissolved or suspended in dry THF, is treated with about 1.1 equivalents of 2.5M n-BuLi in hexane. This mixture is allowed to stir at about −78° C. for about one hour. Then approximately one equivalent of the aldehyde (II), dissolved in anhydrous THF, is added to the formed yilide solution at about −78° C. After about one hour of stirring at about −78° C., the reaction mixture is allowed to warm to room temperature over about 18 hours. The reaction is worked-up by pouring it into water and extracting twice with a solvent such as ethyl acetate. The ethyl acetate is evaporated and the crude product is chromatographed on silica gel using 15% ether/hexanes as the eluant to yield the desired compound (IV). Both the cis and trans isomers of (IV) are isolated.

(b) In another process, a compound of the formula (IV), where j is 1 and the $R^3$ is either a methyl or an ethyl ester, is saponified to yield the analogous acid. In a typical procedure one equivalent of an ester of the formula (IV) is dissolved in a protic solvent, such as methanol. The ester is then mixed with about 1.5 to 10 equivalents (typically 2 equivalents) of 1N NaOH and heated at reflux temperature for about 0.5 hours to 5 hours (typically 1.5 hours). The reaction mixture is poured into water and washed once with a solvent such as ethyl acetate. The aqueous layer is acidified to about pH 4 typically with HCl (aq) and extracted 3 times with ethyl acetate. The pure desired product can be obtained by standard methods known to those skilled in the art such as crystallization or column chromatography on silica gel.

(c) In yet another process, a compound of the formula (IV) having the double bond can be hydrogenated to yield the corresponding alkylene analog. In a typical procedure about one equivalent of the compound (IV) is mixed with about 0.2 g to 1 g of 10% Pd/C in a mixture of protic and ether solvents, such as methanol and tetrahydrofuran. The mixture is placed in a Parr apparatus and pressurized with about 10 to 55 psi $H_2$, usually about 20 psi $H_2$, and shaken at room temperature (although the temperature may be raised as required) for about 1 to 24 hours, typically about 2 hours. The reaction mixture is filtered through celite to remove the catalyst and purified by chromatography on silica gel.

(d) In an alternative process, certain compounds of formula (VII) can be prepared by the Williamson synthesis, according to the following general reaction scheme:

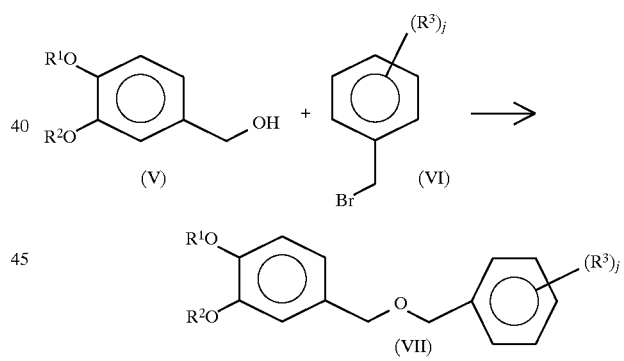

wherein $R^1$, $R^2$, $R^3$ and j are as defined above for formula (I).

In a typical procedure, about 1 to 2 equivalents, typically about 1.05 equivalents, of a 60% oil dispersion of NaH is added to a solution of the alcohol of formula (V) at room temperature. The alcohol of formula (V) is usually dissolved in dry dimethylformamide. The mixture is stirred for about 0.5 to 2 hours, typically about 1 hour, at room temperature, at which time the bromo compound of formula (VI) is added. The reaction mixture is stirred and heated to 100°–125° C. for about 24 hours to 72 hours. The reaction is worked-up by pouring it into water and extracting twice with ethyl acetate followed by purification by chromatography on silica gel.

(e) In a further process, certain compounds of general formula (IX) can be prepared by a Mitsunobu type reaction, according to the following general reaction scheme:

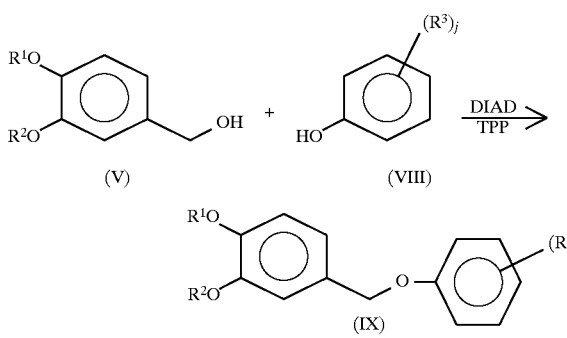

wherein $R^1$, $R^2$, $R^3$ and j are as defined above for formula (I).

In a typical procedure, about 1 to 5 equivalents, typically 1.2 equivalents, of diisopropylazodicarboxylate (DIAD) or diethylazodicarboxylate (DEAD) is added to a mixture of about one equivalent of the alcohol (V), about one equivalent of the phenol (VIII) and about 1.1 equivalents of triphenylphosphine (TPP). All of the reactants are dissolved in a dry solvent, such as tetrahydrofuran. The reaction is stirred at room temperature for about 6 to 24 hours, typically 18 hours. The solvent is evaporated and the crude oil is purified by column chromatography on silica gel to yield the compound of formula (IX).

(f) In another process, certain compounds of the formula (XI) are prepared by the following general reaction scheme:

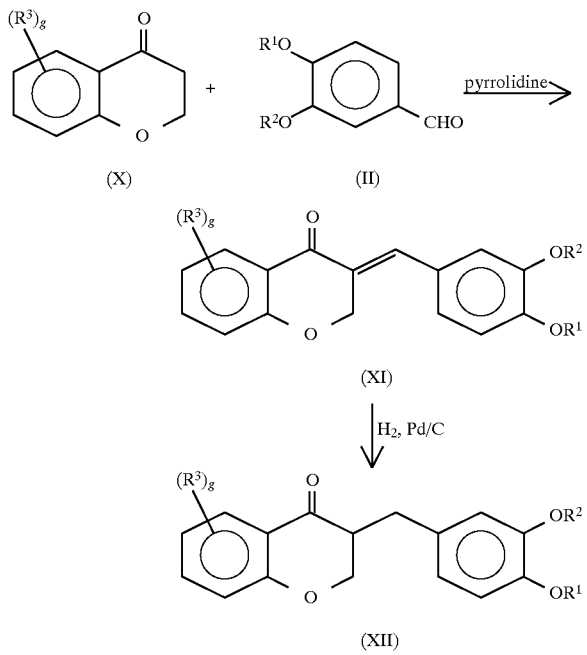

wherein $R^1$, $R^2$, $R^3$ and g are as defined above for formula (I). About 1 equivalent of a secondary amino base, such as pyrrolidine is added to a room temperature solution of about 1 equivalent of the appropriately substituted chromanone (X) and about 1 equivalent of the necessary aldehyde (II) in a protic solvent such as methanol. The mixture is stirred for about 6 to 24 hours, usually 18 hours. The mixture is filtered to give the desired product as a solid. The compound of formula (XI) is then purified by either crystallization or by column chromatography. The compound of formula (XII) is obtained by hydrogenating compound (XI) analogous to method (c) above, (g) In a further process, the ketone moiety of the chromanone compound of formula (XII) described hereinabove in method (f) can be reduced to the corresponding alcohol with a reducing agent such as $NaBH_4$. Approximately 0.8 equivalents of sodium borohydride is added to a solution of approximately 1 equivalent of the chromanone (XII) and about 1 equivalent of $CeCl_3.7H_2O$ in methanol and tetrahydrofuran. The temperature of the solution is usually about −20° C. to −78° C., preferably −50° C. The reaction mixture is allowed to warm to room temperature over about 18 hours. The reaction is worked up by diluting with ethyl acetate and washing once each with $NH_4Cl$ (aqueous), $H_2O$ and brine. It is then dried over $Na_2SO_4$ and concentrated. The crude product is purified by chromatography on silica gel.

(h) Certain compounds having the general formula

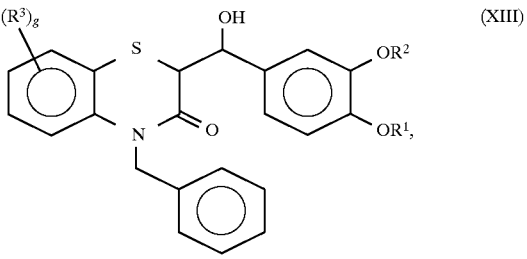

wherein $R^1$, $R^2$, $R^3$ and g are as defined above for formula (I), may be synthesized according to the following scheme:

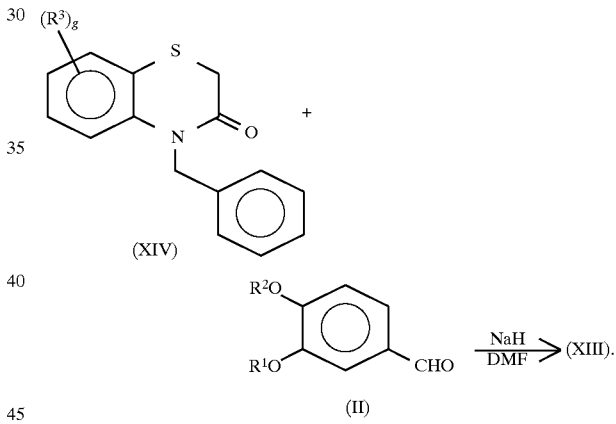

A solution of about one equivalent of (XIV) in dry DMF is added dropwise to a suspension of about 1.1 equivalents of NaH in dry DMF at about 0° C. The solution is stirred at about 0° C. for about 30 minutes when a one equivalent solution of (II) in dry DMF is added. The mixture is allowed to come to room temperature over about 18 hours. The mixture is poured into water and acidified to pH 1. The resulting precipitate is filtered and dried. Further purification is done by chromatography on silica gel.

(i) In yet another process, an alcohol of formula (XIII) described in method (h), above, may be dehydrated to give the corresponding alkenyl analog. In a typical procedure, about 1.5 equivalents of oxalyl chloride is added to a solution of about 2 equivalents of dry DMSO in dry methylene chloride at about −50° C. to −78° C., preferably at −65° C. A solution of the alcohol of the formula (XIII) described in method (h), above, dissolved in dry methylene chloride, is added to the cold solution of DMSO. This mixture is allowed to warm with stirring to about −30° C. over about 1 hour. It is then cooled to about −78° C. and 2 to 10 equivalents of triethylamine is added. This mixture is stirred at room temperature for about 1 hour. The reaction is worked-up. by standard methods known to those skilled in the art and purified either by column chromatography on silica gel or by crystallization.

(j) Certain compounds of the formula (XVI) may be synthesized according to the scheme shown below:

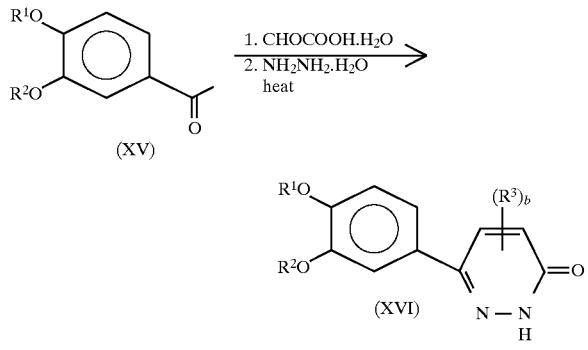

wherein $R^1$, $R^2$, $R^3$ and b are as defined above for formula (I).

In a typical procedure, a ketone of the formula (XV) is heated with glyoxylic acid monohydrate at about 100° C. to 150° C., preferably about 120° C. The reaction is cooled to about 60° C. and about 2 ml of $H_2O$ is added. About 20 to 30 drops of concentrated $NH_4OH$ and about 1 equivalent of hydrazine monohydrate are added. The mixture is then heated at reflux for about 2 hours. It is cooled to room temperature and about 5 ml of water is added. The mixture is stirred for about 50 to 72 hours, preferably for about 60 hours. The suspension is filtered and purified by column chromatography on silica gel followed by crystallization.

(k) Certain compounds of formula (XIX) are prepared by palladium cross coupling according to the following scheme:

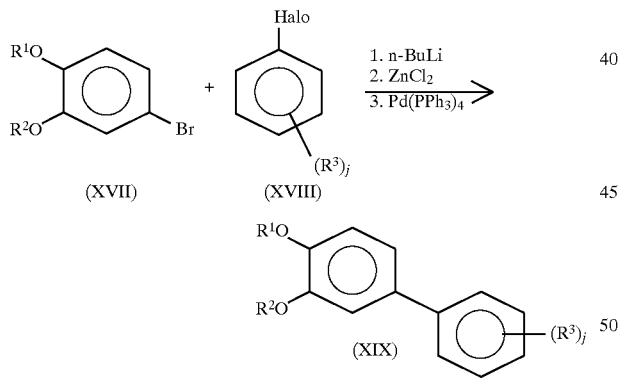

wherein $R^1$, $R^2$, $R^3$ and j are as defined above for formula (I). A typical procedure is carried out by taking a solution of about one equivalent of the appropriate bromo compound (XVII), dissolved in dry THF, and cooling it to about −78° C. About 1.1 equivalents of a 2.5M solution of n-BuLi is added to the bromo compound and stirred for about 40 minutes at about −78° C. About 1.2 equivalents of a 1.0M solution of $ZnCl_2$ in ether is added and the reaction mixture allowed to warm to room temperature over about 35 minutes. A catalytic amount, about 0.05 equivalents, of tetrakis (triphenylphosphine)palladium(O) and the required halo compound (XVIII), wherein "Halo" is I, Br or Cl but preferably I or Br, are added to the reaction mixture and allowed to stir for about 12 hours. The reaction is concentrated and chromatographed on silica gel to yield the desired compound of formula (XIX).

(I) Yet another process which is utilized to prepare certain compounds of formula (I) involves the formation of a tetrazole from a cyano group using $Bu_3SnN_3$, according to the general scheme:

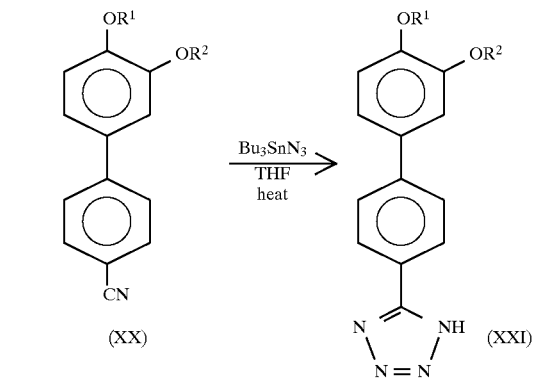

wherein $R^1$ and $R^2$ are as defined above for formula (I).

In a typical method, about one equivalent of the cyano compound of formula (XX), dissolved in dry THF, is mixed with a dry THF solution of $Bu_3SnN_3$ and the mixture heated at reflux temperature for about 4 days. The mixture is cooled to room temperature, concentrated and chromatographed on silica gel to afford the desired tetrazole (XXI).

(m) Certain compounds of formula (I) may also be synthesized by reaction of bromo compounds (XVII) with amino compounds (XXII), according to the general reaction scheme:

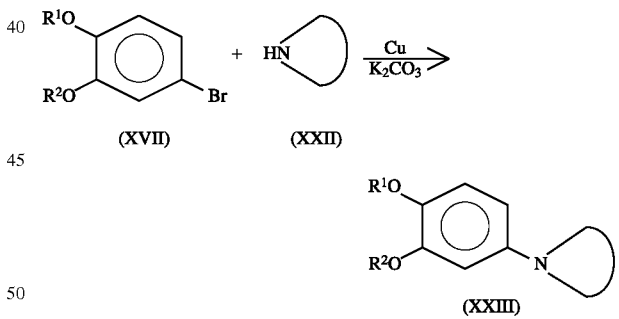

wherein $R^1$ and $R^2$ are as defined above for formula (I) and

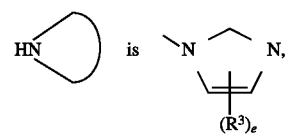

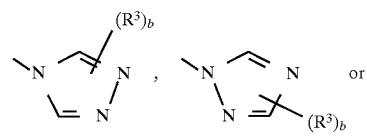

-continued

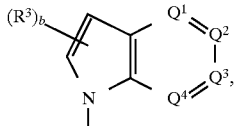

wherein $Q^1$, $Q^2$, $Q^3$, $Q^4$, $R^3$, b and e are as defined above for formula (I).

In a typical procedure, a mixture of about one equivalent of all of the reagents shown in the above scheme are heated to about 110°–150° C. for about 24 hours. The mixture is cooled to room temperature and worked-up according to standard methods well known to those skilled in the art. Chromatography on silica gel yields the desired compound of general formula (XXIII).

(n) The following procedure is employed to synthesize compounds of the formula

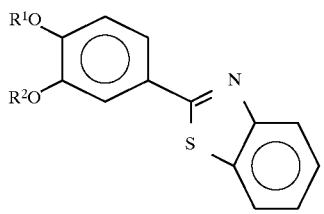 (XXIV)

wherein $R^1$ and $R^2$ are as defined above for formula (I).

About one equivalent of an aldehyde of the formula

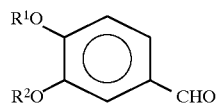 (II)

is mixed with about one equivalent of an optionally substituted 2-mercaptoaniline and heated on a steam bath for about 15 minutes. The reaction mixture is cooled and dissolved in a methanol solution of 10% $FeCl_3$ and stirred overnight. The reaction is diluted with $H_2O$ and extracted with chloroform. The chloroform is evaporated and the residue is chromatographed to yield the desired benzothiazole derivatives of formula (XXIV).

(o) The following procedure is used to synthesize compounds of the formula

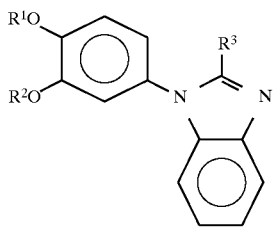 (XXV)

wherein $R^1$, $R^2$ and $R^3$ are as defined above for formula (I).

About one equivalent of a compound of the formula

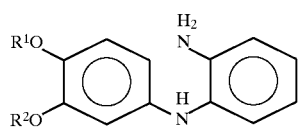 (XXVI)

is mixed with ethyl formate and approximately 25 ml of formic acid and heated at about 100° C. for about 18 hours. The solvent is evaporated and the residue chromatographed on silica gel to yield the desired benzimidazole derivatives of formula (XXV).

(p) Compounds having the general formula

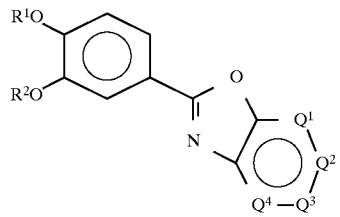 (XXVII)

wherein $R^1$, $R^2$, $Q^1$, $Q^2$, $Q^3$ and $Q^4$ are as defined above for formula (I), are synthesized by the following general method. A compound of the general formula

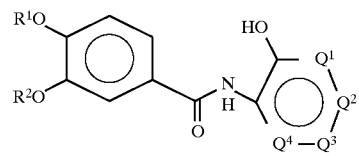 (XXVIII)

is mixed with $POCl_3$ and heated at reflux for about 24 hours. Excess $POCl_3$ is evaporated and the crude product is purified by chromatography on silica gel to yield the desired oxazolo derivatives of formula (XXVII).

(q) Compounds having the general formula

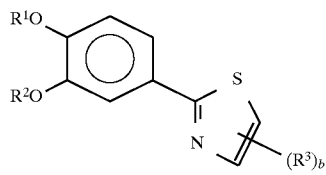 (XXIX)

wherein $R^1$, $R^2$, $R^3$ and b are as defined above for formula (I), are synthesized by the following general method. A compound of the general formula

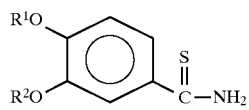 (XXX)

is mixed with chlororacetaldehyde in ethanol and heated at reflux temperature for about 6 hours. The volatile components are evaporated and the residue is purified by chromatography on silica gel to yield the desired thiazole derivative of formula (XXIX).

(r) Compounds having the general formula

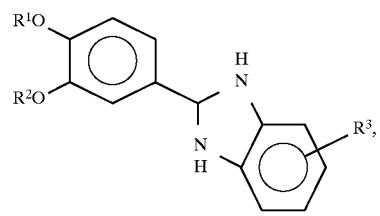 (XXXI)

wherein $R^1$, $R^2$ and $R^3$ are as defined above for formula (I), are synthesized by the following general method. A compound of the general formula (II) is mixed with an appropriate compound of the general formula

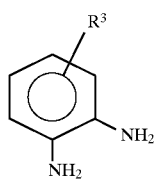
(XXXII)

and the mixture heated to about 120° C. for about 1 to 6 hours. The resulting residue is chromatographed on silica gel to yield the desired derivative of formula (XXXI).

(s) Compounds having the general formula

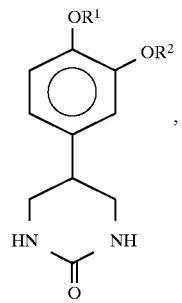
(XXXIII)

wherein $R^1$ and $R^2$ are as defined above for formula (I), are synthesized by one of the two general methods described below. The first general method is a Mitsinobu type reaction illustrated by the general scheme

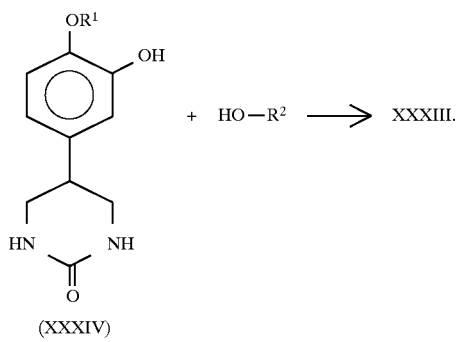

(XXXIV)

The reaction is carried out analogously to the description provided in general method (e) above.

The second general method is carried out according to the following general scheme: XXXIV+Halo-$R^2$→XXXIII, wherein "Halo" is Cl, Br or I.

A compound of general formula (XXXIV) is dissolved in anhydrous DMSO. To this mixture approximately 2.5 equivalents of anhydrous $K_2CO_3$ and the appropriate halide (Halo-$R^2$) are added. The reaction mixture is heated to about 80° C. for about 2–5 hours. After conventional work-up of the reaction mixture, the desired product is isolated by chromatography on silica gel.

The synthetic methods outlined above in methods a to s together with the following Examples describe methods which were and can be employed to prepare the compounds of this invention.

The ability of the compounds or the pharmaceutically acceptable salts thereof to inhibit phosphodiesterase IV ($PDE_4$) and, consequently, demonstrate their effectiveness for treating inflammatory diseases is shown by the following in vitro assay.

BIOLOGICAL ASSAY (Human Lung $PDE_{IV}$)

Thirty to forty grams of human lung tissue is placed in 50 ml of pH 7.4 Tris/phenylmethylsulfonyl fluoride (PMSF)/ sucrose buffer and homogenized using a Tekmar Tissumizer® (Tekmar Co., 7143 Kemper Road, Cincinnati, Ohio 45249) at full speed for 30 seconds. The homogenate is centrifuged at 48,000×g for 70 minutes at 4° C. The supernatant is filtered twice through a 0.22 μm filter and applied to a Mono-Q FPLC column (Pharmacia LKB Biotechnology, 800 Centennial Avenue, Piscataway, N.J. 08854) pre-equilibrated with pH 7.4 Tris/PMSF buffer. A flow rate of 1 ml/minute is used to apply the sample to the column, followed by a 2 ml/minute flow rate for subsequent washing and elution. Sample is eluted using an increasing, step-wise NaCl gradient in the pH 7.4 Tris/PMSF buffer. Eight ml fractions are collected. Fractions are assayed for specific $PDE_{IV}$ activity, determined by [$^3$H]cAMP hydrolysis and the ability of a known $PDE_{IV}$ inhibitor (e.g. rolipram) to inhibit that hydrolysis. Appropriate fractions are pooled, diluted with ethylene glycol (2 ml ethylene glycol/5 ml of enzyme prep) and stored at −20° C. until use.

Compounds are dissolved in DMSO at a concentration of 10 mM and diluted 1:25 in water (400 μM compound, 4% DMSO). Further serial dilutions are made in 4% DMSO to achieve desired concentrations. Final DMSO concentration in assay tube is 1%. In duplicate the following are added, in order, to a 12×75 mm glass tube (all concentrations are given as final concentrations in assay tube).

i) 25 μl compound or DMSO (1%, for control and blank)
ii) 25 μl pH 7.5 Tris buffer
iii) [$^3$H]cAMP (1 μM)
iv) 25 μl $PDE_{IV}$ enzyme (for blank, enzyme is preincubated in boiling water for 5 minutes)

The reaction tubes are shaken and placed in a water bath (37° C.) for 20 minutes, at which time the reaction is stopped by placing the tubes in a boiling water bath for 4 minutes. Washing buffer (0.5 ml, 0.1M 4-(2-hydroxyethyl)-1-piperazineethanesulfonic acid (HEPES)/0.1M NaCl, pH 8.5) is added to each tube on an ice bath. The contents of each tube are applied to an Affi-Gel 601 column (Biorad Laboratories, P.O. Box 1229, 85A Marcus Drive, Meiville, N.Y. 11747) (boronate affinity gel, 1 ml bed volume) previously equilibrated with washing buffer. [$^3$H]cAMP is washed with 2×6 ml washing buffer, and [$^3$H]5'AMP is then eluted with 4 ml of 0.25M acetic acid. After vortexing, 1 ml of the elution is added to 3 ml scintillation fluid in a suitable vial, vortexed and counted for [$^3$H].

% Inhibition is determined by the formula:

$$\% \text{ Inhibition} = 1 - \frac{\text{average cpm (test compound)} - \text{average cpm (blank)}}{\text{average cpm (control)} - \text{average cpm (blank)}}$$

$IC_{50}$ is defined as that concentration of compound which inhibits 50% of specific hydrolysis of [$^3$H]cAMP to [$^3$H] 5'AMP.

Pharmaceutically-acceptable acid addition salts of the compounds of this invention include, but are not limited to, those formed with HCl, HBr, $HNO_3$, $H_2SO_4$, $H_3PO_4$, $CH_3SO_3H$, p-$CH_3C_6H_4SO_3H$, $CH_3CO_2H$, gluconic acid, tartar and succinic acid. In the case of those compounds of the formula (I) which contain a further basic nitrogen, it will, of course, be possible to form diacid addition salts (e.g., the dihydrochloride) as well as the usual monoacid addition salt. Pharmaceutically-acceptable cationic salts of the compounds of this invention include, but are not limited to, those of sodium, potassium, calcium, magnesium, ammonium, N,N'-dibenzylethyl-enediamine, N-methylglucamine (meglumine), ethanolamine and diethanolamine.

For administration to humans in the curative or prophylactic treatment of inflammatory conditions, oral dosages of the compounds are generally in the range of from 0.1–100 mg daily for an average adult patient (70 kg). Thus for a typical adult patient, individual tablets or capsules contain from 0.1 to 50 mg of active compound, in a suitable pharmaceutically acceptable vehicle or carrier. Dosages for intravenous administration are typically within the range of 0.1 to 10 mg per single dose as required. For intranasal or inhaler administration, the dosage is generally formulated as a 0.1 to 1% (w/v) solution. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For human use, the compounds of the formula (I) can be administered alone, but will generally be administered in an admixture with a pharmaceutical diluent or carrier selected with regard to the intended route of administration and standard pharmaceutical practice. For example, they may be administered orally in the form of tablets containing such excipients as starch or lactose, or in capsules or ovales either alone or in admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substances; for example, enough salts or glucose to make the solution isotonic.

Thus in a further aspect the invention provides pharmaceutical compositions comprising a compound of the formula (I), or pharmaceutically acceptable salts thereof, together with a pharmaceutically acceptable diluent or carrier.

This invention also provides a method of inhibiting phosphodiesterase IV ($PDE_{IV}$) in a mammal in need thereof which method comprises administering to said mammal a phosphodiesterase IV inhibiting amount of a compound of the formula (I) or pharmaceutically acceptable salt thereof.

This invention further provides a method of treating an inflammatory condition in mammals which comprises administering to said mammal an antiinflammatory amount of a compound of the formula (I) or pharmaceutically acceptable salt thereof.

Further still, this invention provides a method of treating AIDS, asthma, arthritis, bronchitis, chronic obstructive pulmonary disease, psoriasis, allergic rhinitis, dermatitis or shock in a mammal which comprises administering to said mammal an effective amount of a compound or a pharmaceutically acceptable salt thereof.

The present invention is illustrated by the following examples, but it is not limited to the details thereof.

EXAMPLE 1

Methyl 3-[2-[3-(cyclopentyloxy)-4-methoxyphenyl] ethenyl] benozate

To a −78° C. suspension of (1.55 g, 3.16 mmol, 1.05 eq) 3-carbomethoxy-benzyltriphenylphosphonium bromide in 50 ml of anhydrous tetrahydrofuran (1.20 ml of 2.5M, 3.01 mmol, 1.0 eq) n-BuLi in hexane was added dropwise. After stirring 45 minutes at −78° C., a solution of (0.663 g, 3.01 mmol, 1.0 eq) 3-cyclopentyloxy-4-methoxybenzaldehyde in 20 ml of anhydrous tetrahydrofuran was added dropwise, and the reaction mixture was allowed to warm to room temperature over 18 hours. The reaction mixture was poured into 300 ml $H_2O$ and extracted twice with ethyl acetate. The ethyl acetate extracts were combined, washed once with brine, dried over $Na_2SO_4$, and concentrated to yield 2.12 g of a yellow oil. Silica gel chromatography eluting with 15% ether-hexane afforded 386 mg, 36%, of the cis isomer and 380 mg, 36%, of the trans isomer. Mass spectra: $M^+$=352.

EXAMPLE 2–3

Reaction of the appropriate aldehyde with the requisite aryitriphenylphosphonium bromide, analogous to the procedure of Example 1, afforded the following compounds having the general formula:

$$R^1O\text{-}\underset{R^2O}{\diagdown}\text{phenyl-CH=CH-}Z$$

| | | | | | | Analysis | | | | | |
| | | | | | | Calculated (%) | | | Found (%) | | |
| Ex. # | Isomer | $R^1$ | $R^2$ | Z | M.P. °C. | C | H | N | C | H | N |
| 2 | Cis & Trans Mixture | $CH_3$ | 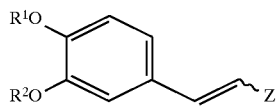 | -phenyl-$CO_2CH_3$ | 65–57° | 76.17 | 6.93 | — | 76.15 | 7.03 | — |

-continued

[Structure: R¹O and R²O substituted benzene with CH=CH-Z]

| Ex. # | Isomer | R¹ | R² | Z | M.P. °C. | Calculated (%) C | H | N | Found (%) C | H | N |
|---|---|---|---|---|---|---|---|---|---|---|---|
| 3 | Cis & Trans Mixture | CH₃ | [cyclohexyl-CH(CH₃)- with phenyl substituent] | [phenyl-CO₂CH₃, para-substituted] | Oil | 78.11 | 7.02 | — | 78.23 | 7.21 | — |

EXAMPLE 4

3-[2-[3-(Cyclopentyloxy)-4-methoxyphenyl]ethenyl]benzoic Acid

A mixture of (335 mg, 0.951 mmol, 1.0 eq) methyl, 3-[2-[3-(cyclopentyloxy)-4-methoxyphenyl]ethenyl] benzoate in 8 ml methanol and 1.9 ml (1.90 mmol, 2.0 eq) of 1N NaOH was heated to reflux for 1.5 hours. The reaction mixture was cooled to room temperature, concentrated in vacuo, poured into 100 ml H₂O, basified to pH 12, and washed once with ethyl acetate. The aqueous layer was acidified to pH 4 and extracted three times with ethyl acetate. The ethyl acetate extracts were combined, washed once with H₂O, once with brine, dried over NA₂SO₄, and concentrated to yield 295 mg of white waxy crystals. Recrystallization from ethyl acetate-hexane afforded 100 mg, 34%/, of the cis isomer as white crystals. M.P.: 93°–94° C. Elemental Analysis: Calc'd for C₂₁H₂₂O₄: Calc'd: C, 74.53; H, 6.55. Found: C, 74.32; H, 6.68.

EXAMPLES 5–6

Reaction of the appropriate methyl ester, analogous to the procedure of Example 4, afforded the following compounds:

[Structure: R¹O and R²O substituted benzene with CH=CH linked to phenyl-CO₂H]

| Ex. # | Isomer | R¹ | R² | M.P. °C. | Calculated (%) C | H | Found (%) C | H |
|---|---|---|---|---|---|---|---|---|
| 5 | Trans | CH₃ | cyclopentyl | 137–138° | 74.53 | 6.55 | 74.27 | 6.39 |
| 6 | Cis | CH₃ | cyclopentyl | 79–81° | — | — | — | — |

EXAMPLE 7

Methyl 4-[2-[4-methoxy-3-(1-methyl-phenylbutoxy)phenyl]ethyl]benzoate

A mixture of (1.18 g, 2.74 mmol, 1.0 eq) methyl 4-[2-[4-methoxy-3-(1-methyl-4-phenylbutoxy)phenyl]ethenyl] benzoate and 0.600 g of 10% Pd/C in 30 ml methanol and 30 ml tetrahydrofuran was placed on a Parr hydrogenation apparatus and shaken under 20 psi H₂ at room temperature for 1.5 hours. The reaction mixture was filtered through celite, concentrated in vacuo, and flash chromatographed on a silica gel column eluting with 20% ether-hexane to afford 1.00 g, 84%, of a clear oil. Elemental Analysis Calc'd for C₂₈H₃₂O₄: Calc'd: C, 77.75; H, 7.46. Found: C, 77.55; H, 7.55.

EXAMPLE 8–10

Reaction of the appropriate alkenylaryl methyl ester, analogous to the procedure Example 7, afforded the following compounds:

| Ex. # | $R^1$ | $R^2$ | Position of $CO_2CH_3$ | M.P. °C. | Formula (MW) | Mass Spec (M+) | Calculated (%) C | Calculated (%) H | Found (%) C | Found (%) H |
|---|---|---|---|---|---|---|---|---|---|---|
| 8 | $CH_3$ | cyclopentyl | meta | oil | $C_{22}H_{26}O_4$ 354.4 | 354 | — | — | — | — |
| 9 | $CH_3$ | norbornyl | meta | oil | $C_{24}H_{28}O_4$ 380.4 | 380 | 75.77 | 7.42 | 75.58 | 7.68 |
| 10 | $CH_3$ | norbornyl | para | 72–74° | $C_{24}H_{28}O_4$ 380.4 | 380 | — | — | — | — |

EXAMPLE 11

4-[2-[4-methoxy-3-(1-methyl-4-phenyl-butoxy)phenyl]ethyl]benzoic acid

Reaction of methyl, 4-[2-[4-methoxy-3-(1-methyl-4-phenylbutoxy)phenyl]ethyl]-benzoate, analogous to the procedure of Example 4, yielded the title compound, 735 mg, 91%, as white crystals. M.P.: 112° C. Elemental Analysis Calc'd for $C_{27}H_{30}O_4$: Calc'd: C, 77.48; H, 7.23. Found: C, 77.62; H, 7.36.

EXAMPLE 12–14

Reaction of the appropriate methyl ester, analogous to the procedures of Example 11, afforded the following compounds:

| Ex. # | $R^1$ | $R^2$ | Position of $CO_2H$ | M.P. °C. | Calculated (%) C | Calculated (%) H | Found (%) C | Found (%) H |
|---|---|---|---|---|---|---|---|---|
| 12 | $CH_3$ | cyclopentyl | meta | 86–8° | 74.09 | 7.11 | 74.21 | 7.16 |

-continued

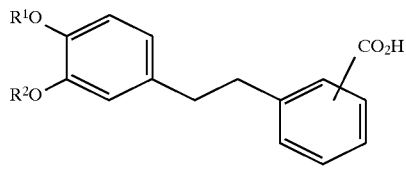

|  |  |  | Position |  | Analysis | | | |
|  |  |  |  |  | Calculated (%) | | Found (%) | |
| Ex. # | R¹ | R² | of CO₂H | M.P. °C | C | H | C | H |
|---|---|---|---|---|---|---|---|---|
| 13 | CH₃ | (norbornyl) | meta | 105–7° | 75.39 | 7.15 | 75.54 | 7.16 |
| 14 | CH₃ | (norbornyl) | para | 149–50° | 75.39 | 7.15 | 75.20 | 7.13 |

EXAMPLE 15

3-[[[3-(Bicyclo[2.2.1]hept-2-yloxy)-4-methoxyphenyl]methoxy]methyl]benzoic acid

Added (178 mg, 4.44 mol, 1.05 eq) 60% NaH to a room temperature solution of (1.05 g, 4.23 mmol, 1.0 eq) 3-(bicyclo[2.2.1]hept-2-yloxy)-4-methoxyphenylmethanol in 20 ml anhydrous dimethylformamide. After stirring 45 minutes at room temperature, (1.45 g, 6.35 mmol, 1.5 eq) of methyl-3-bromomethylbenzoate was added. After 60 hours at room temperature, the reaction mixture was poured into 300 ml H₂O and extracted twice with ethyl acetate. The ethyl acetate extracts were washed twice with H₂O, once with brine, dried over Na₂SO₄, and concentrated to yield 2.33 g of a yellow oil. Silica gel chromatography eluting with 10%, then 20% ethyl acetate-hexane afforded 322 mg, 19%, of a colorless oil, methyl, 3-[[[3-(bicyclo[2.2.1]hept-2-yloxy)-4-methoxyphenyl]methoxy]methyl]benzoate.

A mixture of (310 mg, 0.782 mmol, 1.0 eq) the above methyl ester (the colorless oil) in 10 ml methanol and 3 ml of 1N NaOH was heated to reflux for 2 hours. The reaction mixture was cooled to room temperature, concentrated in vacuo, poured into 150 ml H₂O and 25 ml ethyl acetate, acidified to pH 4.5, and extracted twice with ethyl acetate. The ethyl acetate extracts were washed once with H₂O, once with brine, dried over Na₂SO₄, and concentrated to yield 0.28 g of a pale yellow oil. Silica gel chromatography, eluting with 5% CH₃OH—CH₂Cl₂, followed by recrystallization from ether/petroleum ether afforded 217 mg, 73%, of white crystals. M.P.: 77°–79° C. Elemental Analysis: Calc'd for $C_{23}H_{26}O_5$: Calc'd: C, 72.31; H, 6.86. Found: C, 72.30; H, 6.80.

EXAMPLE 16

2-[3-(Bicyclo[2.2.1]hept-2-yloxy)-4-methoxyphenylmethoxy]nicotinic acid

A mixture of (0.82 g, 3.3 mmol, 1.0 eq) (±)-3-exo-norbornyloxy-4-methoxybenzyl alcohol and (0.263 g, 6.6 mmol, 2.0 eq) NaH (60% oil dispersion) in 20 ml of anhydrous dimethylformamide was stirred at room temperature for 0.5 hours. 2-Chioronicotinic acid (0.52 g, 3.3 mmol, 1.0 eq) was added, and the reaction mixture heated to reflux for 24 hours. The reaction mixture was cooled to room temperature, concentrated in vacuo, dissolved in ethyl acetate and washed with 2N NaOH. The base wash was acidified to pH 5–6 and extracted with ethyl acetate. The ethyl acetate extracts were washed twice with H₂O, once with brine, dried over Na₂SO₄ and concentrated to yield 944 mg of a white semi-solid. Silica gel chromatography eluting with 2½%, then 4% CH₃OH—CH₂Cl₂ afforded 69 mg, 6%, of a white amorphous foam. M.P.: 50° C.+(dec.).

EXAMPLE 17

6-[[3-(Bicyclo[2.2.1]-hept-2-yloxy)-4-methoxyphenyl]methoxy]-α-methyl-2-naphthaleneacetic acid (±)-3-Exo-norbornyloxy-4-methoxybenzyl bromide (0.719 g, 2.31 mmol, 1.0 eq) was added to a mixture of (0.50 g, 2.31 mmol, 1.0 eq) α-methyl-2-(5-hydroxynaph-thalene acetic acid and (1.12 g, 3.5 eq, 8.09 mmol) K₂CO₃ in 35 ml of anhydrous dimethylformamide. After stirring 18 hours at room temperature under N₂, the reaction mixture was poured into 350 ml of H₂O, acidified to pH 4–5 and extracted with ethyl acetate. The ethyl acetate extracts were combined, washed twice with H₂O, once with brine, dried over Na₂SO₄, and concentrated in vacuo to yield a yellow-brown oil. Silica gel chromatography eluting with 2½% CH₃OH—CH₂Cl₂ gave 0.52 g of a white amorphous solid. Recrystallization from isopropanol-hexane yielded 0.47 g, 46%, of a light yellow crystal. M.P.: 125°–128° C. Elemental Analysis: Calc'd for $C_{28}H_{30}O_5$: Calc'd: C, 75.31; H, 6.77. Found: C, 75.26; H, 7.01.

EXAMPLE 18

Methyl 3-[[3-(cyclopentyloxy)-4-methoxyphenyl]methoxy]benzoate

Diisopropylazodicarboxylate (1.2 ml, 5.99 mmol, 1.2 eq) was added to a mixture of (1.10 g, 4.99 mmol, 1.0 eq)

3-cyclopentyloxy-4-methoxybenzyl alcohol, (1.44 g, 5.49 mmol, 1.1 eq) triphenylphosphine, and (0.75 g, 4.99 mmol, 1.0 eq) methyl-3-hydroxy-benzoate in 30 ml of anhydrous tetrahydrofuran. After stirring for 18 hours at room temperature the reaction mixture was concentrated in vacuo and chromatographed on a silica gel column, eluting with 10%, then 15% ethyl acetate-hexane to yield 897 mg, 50%, of a clear oil. High Resolution Mass Spectra: Calc'd 356.1624. Found: 356.1600.

EXAMPLE 19

Tetrahydro-5-[4-methoxy-3-(difluoro-methoxy) phenyl]-2(1H)-pyrimidinone

Chlorodifluoromethane was bubbled into a solution of (102 mg, 0.459 mmol, 1.0 eq) of tetrahydro-5-(4-methoxy-3-hydroxyphenyl)-2(1H)-pyrimidinone and 64 mg (1.61 mmol, 3.5 eq) of NaOH in 3 ml of $H_2O$ and 3 ml of 1,4-dioxane. After 1 hour at room temperature, the reaction mixture was heated to 60° C. for 1.5 hours. Chlorodifluoromethane was bubbled in continuously. The reaction mixture was cooled to room temperature, poured into 150 ml of $H_2O$ and 75 ml of ethyl acetate, extracted twice with ethyl acetate. The ethyl acetate extracts were washed twice with 2N NaOH, once with brine, dried over $Na_2SO_4$, and concentrated to yield 13.5 mg of a white solid, which was recrystallized from ethyl acetate-hexane to afford 8.4 mg, 7%, of off-white crystals. M.P.: 215°–216° C. Elemental Analysis: Calc'd for $C_{12}H_{14}N_2O_3F_2$: Calc'd: C, 52.95; H, 5.18; N, 10.29. Found: C, 52.88; H, 4.91; N, 10.13.

EXAMPLE 20

5-(3-(Bicyclo[2.2.1]hept-2-yloxy)-4-difluoro-methoxyphenyl)tetrahydro-2(1H)-pyrimidone Pb(OAc)$_4$ (2.96 g of 95%, 6.67 mmol, 2.2 eq) was added portionwise to a slurry of (1.16 g, 3.03 mmol, 1.0 eq) 3-[3-bicyclo[2.2.1]hept-2-yloxy)-4-(difluoromethoxy)-phenyl]pentanediamide, in 50 ml anhydrous pyridine. After stirring 18 hours at room temperature, the reaction mixture was poured into 600 ml of $H_2O$ and extracted four times with ethyl acetate. The ethyl acetate extracts were washed once with brine, dried over $Na_2SO_4$, and concentrated to yield 1.4 g of a yellow solid. Silica gel chromatography eluting with 2½%, then 3% $CH_3OH$—$CH_2Cl_2$ yielded 1.06 g of a white solid. Recrystallization from ethyl acetate-hexane afforded 598 mg, 56%, of white crystals. M.P.: 217°–219° C. Elemental Analysis Calc'd for $C_{18}H_{22}N_2O_3F_2$: Calc'd: C, 61.35; H, 6.29; N, 7.95. Found: C, 61.53; H, 6.38; N, 7.81.

EXAMPLE 21

Tetrahydro-5-[3-(4-phenylbutoxy)-4-methoxyphenyl]-2(1H)-pyrimidinone

Diisopropylazodicarboxylate (1.1 ml, 5.70 mmol, 1.2 eq) was added to a mixture of (1.06 g, 4.75 mmol, 1.0 eq) tetrahydro-5-(3-hydroxy-4-methoxyphenyl)-2(1H)-pyrimidinone, (1.37 g, 5.23 mmol, 1.1 eq) triphenylphosphine, and (714 mg, 4.75 mmol, 1.0 eq) 4-phenyl-1-butanol in 20 ml of anhydrous tetrahydrofuran. After heating to reflux for 18 hours, the reaction mixture was cooled to room temperature, diluted with 350 ml ethyl acetate, washed twice with 1N NaOH, once with $H_2O$, once with brine, dried over $Na_2SO_4$, and concentrated to yield an orange solid. Silica gel chromatography eluting with 4% $CH_3OH$—$CH_2Cl_2$ yielded 527 mg of a white solid, which was recrystallized from ethyl acetate to afford 480 mg, 29%, of white needles. M.P.: 142°–143° C. Elemental Analysis Calc'd for $C_{21}H_{26}N_2O_3$: Calc'd: C, 71.17; H, 7.40; N, 7.90. Found: C, 71.12; H, 7.32; N, 7.75.

EXAMPLE 22–27

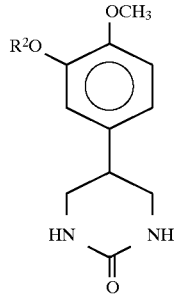

Reaction of 2(1H)-pyrimidine, tetrahydro-5-(3-hydroxy-4-methoxyphenyl)-with the appropriate alcohol of the general formula R—OH, analogous to the procedure of Example 21, yielded the following compounds:

| Ex. # | R$^2$ | M.P. °C. | Calculated (%) | | | Found (%) | | |
|---|---|---|---|---|---|---|---|---|
| | | | C | H | N | C | H | N |
| 22 | H$_3$CO-[norbornyl-O-phenyl-CH$_2$-] | 157–60° | 69.01 | 7.13 | 6.19 | 67.58 | 6.76 | 6.33 |
| 23 | Ph-CH$_2$CH$_2$-CH(CH$_3$)- | 152–4° | 71.17 | 7.40 | 7.90 | 71.13 | 7.42 | 7.80 |

-continued

| | | | Analysis | | | | | |
|---|---|---|---|---|---|---|---|---|
| | | | Calculated (%) | | | Found (%) | | |
| Ex. # | R² | M.P. °C. | C | H | N | C | H | N |
| 24 | Ph−CH(CH₃)−CH₂−CH₂− (Ph, CH₃ branch) | 99–101° | — | — | — | — | — | — |
| 25 | Ph−O−CH₂−CH₂− | 147–9° | — | — | — | — | — | — |
| 26 | Ph−(CH₂)₅− | 160–2° | 71.72 | 7.66 | 7.60 | 71.17 | 7.49 | 7.48 |
| 27 | Ph−(CH₂)₄−CH(CH₃)− | 90–2° | 72.22 | 7.91 | 7.32 | 72.20 | 7.79 | 7.27 |

EXAMPLE 28

5-[3-(Bicyclo[2.2.1]hept-2-yloxy)-4-methoxyphenyl] tetra-hydro-1,3-bis(2-quinolinylmethyl)-2(1H)-pyrimidinone NaH (63 mg, 1.58 mmol, 1.0 eq, 60% oil dispersion) was added to a mixture of (0.500 g, 1.58 mmol, 1.0 eq) 5-[3-(bicyclo[2.2.1]hept-2-yloxy)4-methoxyphenyl]tetra-hydro-2(1H)-pyrimidinone and (0.279 g, 1.58 mmol, 1.0 eq) 2-chloromethylquinoline in 12 ml of anhydrous dimethylformamide. After stirring for 18 hours at room temperature, the reaction mixture was diluted with 250 ml of H₂O and extracted with ethyl acetate. The ethyl acetate extract was washed once with H₂O, once with brine, dried over Na₂SO₄, and concentrated in vacuo. The residue was chromatographed on a silica gel column, eluting with 2½% CH₃OH–CH₂Cl₂ to yield 50 mg of a solid, which was recrystallized from ethyl acetate-hexane to afford 45 mg, 5%, of a white crystalline solid. M.P.: 135°–136° C.

EXAMPLE 29

1-[(7-Chloro-2-quinolinyl)methyl]4-[3 (cyclopentyloxy)-4methoxyphenyl]-2-pyrrolidinone 4-[3-Cyclopentyloxy-4-methoxyphenyl]-2-pyrrolidinone (1.00 g, 3.63 mmol, 1.0 eq) was added to a room temperature suspension of (145 mg, 3.63 mmol, 1.0 eq) NaH (60% oil dispersion) in 30 ml of anhydrous DMF. After stirring at room temperature for 1 hour, (0.77 g, 3.63 mmol, 1.0 eq) 2-chloromethyl-7-chloroquinoline was added, and the reaction mixture was allowed to stir at room temperature for 60 hours. The reaction mixture was then diluted with 250 mL H₂O and extracted with ethyl acetate. The ethyl acetate extract was washed twice with H₂O, once with brine, dried over Na₂SO₄ and concentrated to yield a yellow oil. Silica gel chromatography eluting with 5% CH₃OH/CH₂Cl₂ followed by recrystallization from ethyl acetate-hexane yielded 0.61 g, 37%, of white crystals. M.P.: 106°–107° C. Elemental Analysis Calc'd for C₂₆H₂₇N₂O₃Cl: Calc'd: C, 69.15; H, 6.03; N, 6.21. Found: C, 69.22; H, 5.75; N, 615.

EXAMPLE 30

1-(6-Fluoroquinolin-2-ylmethyl)-4-[3-(cyclopentyloxy)-4-methoxyphenyl]pyrrolidinone Reaction of 4-[3-(cyclopentyloxy)-4-methoxyphenyl] pyrrolidinone with 2-chloromethyl-6-fluoroquinoline, analogous to the procedure of Example 29, yielded the title compound. M.P.: 65°–68° C. High Resolution Mass Spectra: Calc'd: 434.1983. Found: 434.2005.

EXAMPLE 31

[(3-Benzoic acid)methyl-4-(3-cyclopentyloxy)-4-methoxyphenyl]-2-pyrrolidinone

NaH (145 mg, 3.63 mmol, 1.0 eq, 60% oil dispersion) was added to a room temperature solution of (1.00 g, 3.63 mmol, 1.0 eq) of [3-(cyclopentyloxy)-4-ethoxy-phenyl] pyrrolidinone in 20 ml of anhydrous DMF. After stirring 45 minutes at room temperature, (832 mg, 3.63 mmol, 1.0 eq) methyl-3-bromomethylbenzoate was added. After 60 hours at room temperature, the reaction mixture was diluted with 200 ml H₂O and extracted with 200 ml of ethyl acetate. The ethyl acetate extract was washed twice with H₂O, once with brine, dried over Na₂SO₄, and concentrated in vacuo to yield a light yellow oil. Silica gel chromatography eluting with 10%, then 20% ethyl acetate–CH₂Cl₂ yielded 0.33 g, 21%, of a clear oil.

A mixture (0.33 g, 0.78 mmol, 1.0 eq) of the above methyl ester in 8.0 ml of methanol and 2.0 ml of 1N NaOH was heated to reflux for 3 hours. The reaction mixture was cooled to room temperature, concentrated in vacuo, diluted with H₂O, acidified to pH 4.5, and extracted with 2×200 ml ethyl acetate. The ethyl acetate extracts were combined, washed once with brine, dried over Na₂SO₄, and concentrated to give 300 mg of a white foamy solid. Recrystallization from ethyl acetate-hexane yielded 271 mg, 85%, of white crystals. M.P.: 110°–113° C.

EXAMPLE 32

3-[2-[3-Bicyclo[2.2.1]hept-2-yloxy)-4methoxyphenyl]-methenyl]-2,3-dihydro-6-methoxy-4H-1-benzopyran-4-one Pyrrolidine (470 μl, 5.61 mmol, 1.0 eq) was added to a room temperature solution of (1.00 g. 5.61 mmol, 1.0 eq) 6-methoxychromanone and (1.38 g, 5.61 mmol, 1.0 eq) of 3(bicyclo[2.2.1]hept-2-yloxy)-4-methoxy benzaldehyde in 25 ml of methanol. After stirring 18 hours at room temperature, the reaction mixture was filtered, and the filtrant washed with methanol twice to yield 1.76 g, 77%/, of a yellow powder. M.P.: 82°–85° C. Elemental Analysis Calc'd for $C_{25}H_{26}O_5$: Calc'd: C, 73.86; H, 6.45. Found: C, 73.85; H, 6.33.

EXAMPLE 33

3-[2-[3-(Bicyclo[2.2.1]hept-2-yloxy)-4-methoxyphenyl]-methyl]-2,3-dihydro-5-methoxy-4H-1-benzopyran-4-one A mixture of (1.40 g, 3.44 mmol, 1.0 eq) 3-[2-[3-bicyclo[2.2.1]hept-2-yloxy)-4-methoxyphenyl]methenyl]-2,3-dihydro-6-methoxy-4H-1-benzopyran4-one and 600 mg of 10% Pd/C in 15 ml ethyl acetate and 15 ml tetrahydrofuran was placed on a Parr Hydrogenator and shaken under 40 psi $H_2$ at room temperature for 2 hours. The reaction mixture was filtered through celite, and concentrated in vacuo to yield 1.78 g of a pale yellow oil. Silica gel chromatography eluting with $CH_2Cl_2$ afforded 963 mg, 68%, of a clear oil. High Resolution Mass Spectra: Calc'd: 408.1937. Found: 408.1937.

EXAMPLE 34

3-[[3-(Bicyclo[2.2.1]hept-2-yloxy)-4-methoxyphenyl]-methyl]-3,4-dihydro-6methoxy-2H-1-benzopyran-4-ol Sodium borohydride (59 mg, 1.57 mmol, 0.8 eq) was added to a −50° C. solution of (800 mg, 1.96 mmol, 1.0 eq) 3-[2-[3-(bicyclo[2.2.1]hept-2-yloxy)-4-methoxyphenyl]ethyl]-2,3-dihydro-6-methoxy-4H-1-benzopyran-4-one and (730 mg, 1.96 mmol, 1.0 eq) $CeCl_3.7H_2O$ in 20 ml of methanol and 7 ml of tetrahydrofuran. The reaction mixture was allowed to warm to room temperature over 18 hours. The reaction mixture was concentrated in vacuo, diluted with ethyl acetate, washed once with $NH_4Cl$ (aq.), once with $H_2O$, once with brine, dried over $Na_2SO_4$, and concentrated in vacuo. The residue was chromatographed on a silica gel column eluting with 15% ethyl acetate-hexane, to yield 688 mg of a white amorphous foam. Recrystallization from ethyl acetate-hexane yielded 593 mg, 74%, of white crystals. M.P.: 115°–117° C. Elemental Analysis Calc'd for $C_{25}H_{30}O_5$: Calc'd: C, 73.14; H, 7.37. Found: C, 73.35; H, 7.39.

EXAMPLE 35

2-[[3-(Bicyclo[2.2.1]hept-2-yloxy)-4-methoxyphenyl]-α-hydroxy-methyl]-4-(phenylmethyl)-2H-1,4-benzothiazin-3(4H)-one A solution of (1.04 g, 4.06 mmol, 1.0 eq) 4-(phenylmethyl)-2H-1,4-benzothiazin-3-(4H)-one in 10 ml of dry dimethylformamide was added dropwise to a 0° C. suspension of (179 mg, 4.47 mmol, 1.1 eq) NaH (60% oil dispersion) in 5 ml of anhydrous dimethylformamide. After stirring at 0° C. for 30 minutes, a solution of (1.00 g, 4.06 mmol, 1.0 eq) 3-(bicyclo[2.2.1]hept-2-yloxy)-4-methoxybenzaldehyde in 10 ml of dry dimethylformamide was added dropwise. The reaction mixture was allowed to come to room temperature over 18 hours, then it was poured into 1 L of $H_2O$, acidified to pH 1, and the resulting precipitate filtered and dried to yield 2 g of a yellow solid. Silica gel chromatography eluting with 2.5% $CH_3OH/CH_2Cl_2$ followed by recrystallization from ether-hexane yielded 440 mg, 22%, of yellow crystals. M.P.: 159°–161° C. Elemental Analysis Calc'd for $C_{30}H_{31}NO_4S$: Calc'd: C, 71.83; H, 6.23; N, 2.79. Found: C, 71.89; H, 6.43; N, 2.81.

EXAMPLE 36

2-[[3-(Bicyclo[2.2.1]hept-2-yloxy)-4-methoxyphenyl]-methylene]-4-(phenylmethyl)-2H-1,4-benzothiazin-3(4H)-one To a stirred solution of (87 μl, 1.24 mmol, 2.0 eq) dry dimethylsulfoxide in 3 ml of dry $CH_2Cl_2$ at −65° C. was added (0.46 ml, 0.927 mmol, 1.5 eq) of 2.0M oxalyl chloride in $CH_2Cl_2$. The mixture was stirred at ca. −60° C. for 15 minutes, then a solution of (310 mg, 0.618 mmol, 1.0 eq) 2-[[3-(bicyclo[2.2.1]hept-2-yloxy)-4-methoxyphenyl] hydroxy-methyl]-4-(phenylmethyl)-2H-1,4-benzothiazin-3 (4H)-one in 10 ml dry $CH_2Cl_2$ was added dropwise at −65° C. The mixture was allowed to warm to −30° C. over 1 hour, then cooled to −78° C. and (0.43 ml, 3.09 mmol, 5.0 eq) triethylamine was added to the mixture. The mixture was stirred at room temperature for 1 hour then diluted with 400 ml ethyl acetate, washed twice with $H_2O$, once with brine, dried over $MgSO_4$, and concentrated to give 0.3 g of an oil. Silica gel chromatography eluting with 10% ethyl acetate-hexane gave 120 mg of a yellow oil, which was recrystallized from ether-hexane to yield 55 mg, 18%, of a yellow solid. M.P.: 135°–137° C. Elemental Analysis Calc'd for $C_{30}H_{29}NO_3S$: Calc'd: C, 74.51; H, 6.04; N, 2.90. Found: C, 74.53; H, 5.48; N, 2.88.

EXAMPLE 37

6-[3-(Bicyclo[2.2.1]hept-2-yloxy)-4-methoxyphenyl]-3(2H)-pyridazinone

A mixture of 3-Exo-(±)-norbornyloxy-4-methoxyacetophenone (0.88 g, 3.38 mmol, 1.0 eq) and (0.30 g, 3.29 mmol, 0.95 eq) glyoxylic acid monohydrate was heated to 120° C. for 2.2 hours. The light yellow melt was cooled to 60° C. and 2.0 ml of $H_2O$ was added. Dissolution was brought on by addition of 25 drops of concentrated $NH_4OH$. Hydrazine monohydrate (0.163 g, 3.29 mmol, 0.95 eq) was added and the reaction mixture heated to reflux for 2 hours. The reaction mixture was cooled to room temperature, 5 ml of $H_2O$ was added to it, and the mixture stirred for 60 hours at room temperature. The resulting suspension was filtered, washed with $H_2O$ and air dried to yield 0.87 g of a creamy yellow solid. Silica gel chromatography eluting with 5% $CH_3OH–CH_2Cl_2$, followed by recrystallization from isopropanol-hexane gave 0.50 g, 49%, of off-white crystals. M.P.: 188°–189° C. Elemental Analysis Calc'd for $C_{18}H_{20}N_2O_3$: Calc'd: C, 69.21; H, 6.45; N, 8.95. Found: C, 68.92; H, 6.42; N, 8.88.

EXAMPLE 38

1-[4-[[3-Bicyclo[2.2.1]hept-2-yloxy)-4-(difluoromethoxy)-phenyl]methoxy]phenyl]-2-methyl-1H-imidazo[4,5-c]pyridine Diethylazodicarboxylate (59 μl, 0.380 mmol, 1.2 eq) was added to a room temperature mixture of (90 mg, 0.317 mmol, 1.0 eq) 3-(bicyclo[2.2.1]hept-2-yloxy)-4-trifluoromethoxybenzaldehyde, (78 mg, 0.348 mmol, 1.1 eq) 4-(2-methyl-1H-imidazo[4.5-c]pyrimidin-3-yl)phenol and (91 mg, 0.348 mmol, 1.1 eq) triphenylphosphine in 5 ml dry tetrahydrofuran. After stirring 18 hours at room temperature, the reaction mixture was diluted with 200 ml of ethyl acetate and washed once with 1N NaOH, once with $H_2O$, once with brine, dried over $MgSO_4$ and concentrated to give 0.2 g of an oil. Flash chromatography on silica gel eluting with 5% $CH_3OH/CH_2Cl_2$ gave 85 mg of an oil, which was crystallized from ether/hexane to give 69 mg, 45%, of white crystals. M.P.: 140°–141° C. Elemental Analysis Calc'd for $C_{28}H_{27}F_2N_3O_3$: Calc'd: C, 68.42; H, 5.64; N, 8.55. Found: C, 68.56; H, 5.38; N, 8.53.

EXAMPLE 39–40

Reaction of the appropriate catechol with 4-(2-methyl-1H-imidazo[4,5-c]pyrimidin-3-yl)phenol, analogous to the procedure of Example 38, yielded the following compounds:

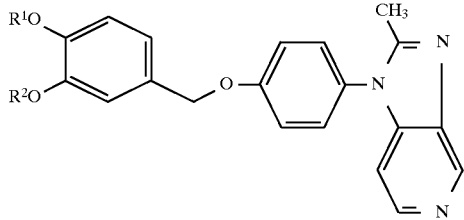

| Ex. # | R¹ | R² | M.P. °C. | Calculated (%) C | H | N | Found (%) C | H | N |
|---|---|---|---|---|---|---|---|---|---|
| 39 | CH₃ | (norbornyl) | 122–4° | 75.47 | 6.56 | 9.43 | 73.56 | 6.27 | 9.03 |
| 40 | CH₃ | (cyclopentylmethyl) | 151–3° | 72.71 | 6.34 | 9.78 | 72.05 | 6.35 | 9.16 |

EXAMPLE 41

1-[4-[2-[3-(Cyclopentyloxy)-4-methoxyphenyl]-ethenylphenyl]-2-methyl-1H-imidazo[4,5-c]pyridine To a stirred suspension of (1.74 g, 3.13 mmol, 1.2 eq) [[3-(cyclopentyloxy)-4-methoxyphenyl]methyl] triphenylphosphonium bromide in 20 ml dry tetrahydrofuran at −50° C. was added (1.1 ml, 2.78 mmol, 1.1 eq) of 2.5M n-BuLi. The mixture was warmed to 0° C. over 1 hour, cooled to −78° C., and a solution of (600 mg, 2.53 mmol, 1.0 eq)-4-(2-methyl-1H-imidazo[4,5-c]pyridin-1-yl) benzaldehyde in 20 ml dry tetrahydrofuran was added dropwise over 10 minutes. The reaction mixture was allowed to warm to room temperature over 18 hours then was quenched with 10 ml saturated NH₄Cl solution. The mixture was poured into 200 ml of H₂O and extracted twice with ethyl acetate. The ethyl acetate extracts were combined, washed once with H₂O, once with brine, dried over MgSO₄, and concentrated to give 2 g of an oil. Flash chromatography eluting with 65% acetone-hexane gave 403 mg of crude product, which was recrystallized from ether-hexane to yield 305 mg, 36%, of the cis product. The trans product was isolated from the chromatography yielding 476 mg, and crystallized from isopropylether to give 415 mg, 39%. Cis-product M.P.: 123°–125° C. Trans-Product M.P.: 156°–158° C. Elemental Analysis of the cis-product: Calc'd for $C_{27}H_{27}N_3O_2$: Calc'd: C, 76.21; H. 6.40; N, 9.87. Found: C, 76.14; H, 6.34; N. 9.71.

EXAMPLE 42

1-[4-[2-[3-(Cyclopentyloxy)-4-methoxyphenyl]-ethyl]phenyl]-2-methyl-1H-imidazo[4,5-c]pyridine A cis and trans mixture of 1-[4-[2-[3-(cyclopentyloxy)-4-methoxyphenyl]-ethenyl]phenyl]-2-methyl-1H-imidazo[4,5-c]pyridine (300 mg, 0.705 mmol 1.0 eq) and 300 mg of 10% Pd/C in 10 ml of tetrahydrofuran and 10 ml of methanol was placed on a Parr hydrogenation apparatus and shaken under 50 psi H₂ at room temperature for 6 hours. The reaction mixture was filtered through celite, concentrated, and chromatographed on a silica gel column eluting with 5% CH₃OH–CH₂Cl₂ to give 230 mg of clear oil. Recrystallization from ether-hexane gave 239 mg, 79%, of white crystals. M.P.: 123°–125° C. Elemental Analysis Calc'd for $C_{27}H_{28}N_3O_2$: Calc'd: C, 75.85; H, 6.84; N, 9.83. Found: C, 75.83; H, 6.74; N, 9.65.

EXAMPLE 43

Methyl 1-[4-[[3-(bicyclo[2.2.1]hept-2-yloxy)-4-methoxyphenyl]methoxyphenyl]-2-butyl-1H-benzimidazole-5-carboxylate Diethylazodicarboxylate (201 μL, 1.28 mmol, 1.3 eq) was added to a mixture of (320 mg, 0.986 mmol, 1.0 eq) methyl 2-butyl-1-(4-hydroxyphenyl)-1H-benzimidazole-5-carboxylate, (269 mg, 1.08 mmol, 1.1 eq) (±)-3-exo-norbornyloxy-4-methoxybenzyl alcohol and (310 mg, 1.18 mmol, 1.2 eq) of triphenylphosphine in 10 ml of dry tetrahydrofuran at room temperature. The reaction mixture was stirred at room temperature for 18 hours, diluted with 300 ml of ethyl acetate and washed twice with 1N NaOH, once with H₂O, once with brine, dried over MgSO₄ and concentrated to give 0.7 g of an oil. Silica gel chromatography eluting with 35% ethyl acetate/hexane gave 298 mg, 54%, of an off-white foam. Mass Spectra: Calc'd for $C_{34}H_{38}N_2O_5$: 554.7. Found: 554.

EXAMPLE 44

1-[4-[[3-bicyclo[2.2.1]hept-2-yloxy)-4-methoxyphenyl]methoxyphenyl]-2-butyl-1H-benzimidazole-5-carboxylic acid Reaction of (260 mg, 0.469 mmol, 1.0 eq) methyl 1-[4-[[3-(bicyclo[2.2.1]hept-2-yloxy)-4-methoxyphenyl] methoxy]phenyl]-2-butyl-1H-benzimidazole-5-carboxylate, (2.3 ml, 2.3 mmol, 5.0 eq) substantially according to the procedure of Example 4 yielded the title compound, 178 mg, 70%, as a white solid. M.P.: 209°–211° C. Elemental Analysis Calc'd for $C_{33}H_{36}N_2O_5$: Calc'd: C, 73.31; H, 6.71; N, 5.18. Found: C, 72.92; H, 6.74; N, 4.94.

EXAMPLE 45

1-[4-[[3-(Bicyclo[2.2.1]-hept-2-yloxy-4-methoxyphenyl]-methoxy]phenyl]-2-butyl-1H-imidazo[4,5-c]pyridine Diethylazodicarboxylate (441 μl, 2.56 mmol, 1.2 eq) was added to a mixture of (570 mg, 2.13 mmol, 1.0 eq) 4-[3H-imidazo[4,5-b]-2-butyl pyridine]phenol, (582 mg, 2.35 mmol, 1.1 eq) (±)-3-exo-norbornyloxy-4-methoxybenzyl alcohol and (616 mg, 2.35 mmol, 1.1 eq) of triphenylphosphine in 25 ml tetrahydrofuran at room temperature. After stirring at room temperature for 60 hours, the reaction mixture was diluted with 400 ml ethyl acetate, washed once with 1N NaOH, once with $H_2O$, once with brine, dried over $MgSO_4$, and concentrated to give 1 g of an oil. Silica gel chromatography eluting with 5% $CH_3OH/CH_2Cl_2$, followed by recrystallization from ether/hexane gave 328 mg, 31%, of a solid. M.P.: 123°–125° C. Elemental Analysis Calc'd for $C_{31}H_{35}N_3O_3$: Calc'd: C, 74.97; H, 6.90; N. 8.46. Found: C, 74.63; H, 7.12; N, 8.29.

EXAMPLE 46

1-[4-[[3-Bicyclo[2.2.1]hept-2-yloxy-]4-difluoromethoxyphenyl]methoxy]phenyl]-2-butyl-2H-imidazo[4,5-c]pyridine Reaction of (±)-3-exo-norbornyloxy-4-difluoromethyloxybenzyl alcohol with 4-3H-imidazo[4,5b]-2-butylpyridine phenol, analogous to the procedure of Example 45, yielded the above-identified compound. M.P.: 129°–131° C. Elemental Analysis Calc'd for $C_{31}H_{33}F_2N_3O_3$: Calc'd: C, 69.78; H, 6.23; N, 7.82. Found: C, 69.66; H, 6.13; N, 7.82.

EXAMPLE 47

3-[4-[[3-(Bicyclo[2.2.1]hept-2-yloxy)-4-methoxyphenyl]methoxy]phenyl]-2-butyl-3H-imidazo[4,5-b]pyridine Diethylazodicarboxylate (365 μl, 2.11 mmol, 1.2 eq) was added to a mixture of (470 mg, 1.76 mmol, 1.0 eq) 4-(2-methyl-3H-imidazo[4,5-b]pyridin-3-yl)phenol, (480 mg 1.93 mmol, 1.1 eq) (±)-3-exo-norbornyloxy-4-methoxybenzyl alcohol, and (506 mg, 1.93 mmol, 1.0 eq) triphenylphosphine in 20 ml of dry tetrahydrofuran. After stirring at room temperature for 60 hours, the reaction mixture was diluted with 400 ml of ethyl acetate, washed twice with 1N NaOH, once with $H_2O$, once with brine, dried over $MgSO_4$ and concentrated to give 0.8 g of an oil. Silica gel chromatography eluting with 60% ethyl acetate/hexane, followed by recrystallization from ether/hexane gave 195 mg, 24%, of tan crystals. M.P.: 130°–132° C. Elemental Analysis Calc'd for $C_{31}H_{35}N_3O_3$: Calc'd: C, 74.82; H, 7.09; N, 8.44. Found: C, 74.44; H, 7.23; N, 8.30.

EXAMPLE 48

3-[4-[[3-Bicyclo[2.2.1]hept-2-yloxy]-4-methoxyphenyl]methoxy]phenyl-2-methyl-3H-imidazo[4,5-b]pyridine Reaction of 2-methyl-3-(4-hydroxyphenyl)-4-azabenzimidazole with (±)-3-exo-norbornyloxy-4-methoxybenzyl alcohol, analogous to the procedure of Example 47, yielded the title compound. M.P.: 72°–75° C. Elemental Analysis Calc'd for $C_{28}H_{29}N_3O_3$: Calc'd: C, 73.82; H, 6.42; N, 9.22. Found: C, 73.12; H, 6.34; N, 8.86.

EXAMPLE 49

1-[4-[[3-Bicyclo[2.2.1]hept-2-yloxy]-4-methoxyphenyl]methoxy]phenyl-2-butyl-1H-benzimidazole Diethylazodicarboxylate (90 μl, 0.580 mmol, 1.2 eq) was added to a mixture of (120 mg, 0.483 mmol, 1.0 eq) 2-butyl-3-(4-hydroxyphenyl)benzimidazole, (126mg, 0.507 mmol, 1.05 eq) (±)-3-exo-norbornyloxy-4-methoxybenzyl alcohol, and (139 mg, 0.531 mmol, 1.1 eq) triphenylphosphine in 10 ml anhydrous tetrahydrofuran. After 18 hours at room temperature, the reaction mixture was diluted with 200 ml of ethyl acetate, washed twice with 1N NaOH, once with $H_2O$, once with brine, dried over $MgSO_4$, concentrated in vacuo to give 0.2 g of an oil. Silica gel chromatography eluting with 40% ethyl acetate/hexane followed by recrystallization from ether/hexane gave 66 mg, 28%, white crystals. M.P.: 134°–136° C. Elemental Analysis Calc'd for $C_{32}H_{36}N_2O_3$: Calc'd: C, 77.39; H, 7.31; N, 8.64. Found: C, 77.08; H, 6.94; N, 5.43.

EXAMPLE 50

4-[4-Methoxy-3-(4-phenylbutyloxy)phenyl]benzoic Acid

To a solution of (2.9 g, 8.65 mmol, 1.0 eq) 1-methoxy-2-(4-phenyl-1-butoxy)-4-bromobenzene in 30 ml of dry THF at −78° C. was added (3.81 ml, 9.52 mmol, 1.1 eq) 2.5M n-BuLi. After stirring 15 minutes at −78° C. (10.4 ml, 10.4 mmol, 1.2 eq) 1.0M $ZnCl_2$ in ether was added and the mixture allowed to warm to room temperature over 35 minutes. Tetrakis(triphenylphosphine)palladium(O) (500 mg, 0.43 mmol, 0.05 eq) and (2.27 g, 8.65 mmol, 1.0 eq) methyl-4-iodobenzoate were added to the reaction and the mixture allowed to stir at room temperature for 2.5 hours. The reaction mixture was concentrated in vacuo, costripped with $CHCl_3$, and chromatographed on a silica gel column eluting with ethyl acetate-hexane (0–10%) to afford 2.61 g, 76%, of a yellow solid. Hydrolysis of the ester according to the method of Example 4 gave the title compound, M.P.: 178°–179° C. Elemental analysis calculated for $C_{24}H_{24}O_4$: C, 76.56; H, 6.43. Found: C, 76.06; H, 5.92.

EXAMPLE 51–72

Reaction of the appropriate bromocatechol, with the required halo aromatic ester if the formula

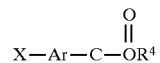

analogous to the procedure of Example 50, followed by hydrolysis substantially according to the procedure of Example 4 yielded the following compounds of the general formula:

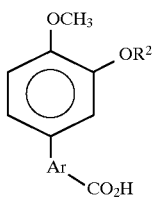
| Ex. # | R² | ArCO₂H | M.P. °C. | Calculated (%) C | H | N | Found (%) C | H | N |
|---|---|---|---|---|---|---|---|---|---|
| 51 | norbornyl | 3-C₆H₄CO₂H | 128–9° | 74.54 | 6.55 | — | 74.86 | 6.82 | — |
| 52 | norbornyl | 2-C₆H₄CO₂H | 66–8° | 74.54 | 6.55 | — | 75.10 | 6.20 | — |
| 53 | norbornyl | 4-C₆H₄CO₂H | 230–2° | 74.54 | 6.55 | — | 74.36 | 6.20 | — |
| 54 | norbornyl | 5-pyridyl-3-CO₂H | 236–8° | 70.78 | 6.24 | 4.13 | 69.95 | 6.09 | 4.17 |
| 55 | norbornyl | 6-pyridyl-3-CO₂H | 221–3° | 70.78 | 6.24 | 4.13 | 70.60 | 6.08 | 4.02 |
| 56 | norbornyl | naphthyl-CO₂H | 242–5° | 77.30 | 6.23 | — | 76.04 | 5.91 | — |

-continued

[Structure: benzene ring with OCH₃, OR², and Ar-CO₂H substituents]

| Ex. # | R² | ArCO₂H | M.P. °C. | Calculated (%) C | H | N | Found (%) C | H | N |
|---|---|---|---|---|---|---|---|---|---|
| 57 | cyclopentyl | 3-carboxyphenyl | 149–51° | 73.05 | 6.47 | — | 72.91 | 6.56 | — |
| 58 | cyclopentyl | 4-carboxyphenyl | 230–32° | 73.05 | 6.47 | — | 73.16 | 6.51 | — |
| 59 | CH(CH₃)(CH₂)₃Ph | 4-carboxyphenyl | 136–8° | 76.90 | 6.71 | — | 76.95 | 6.48 | — |
| 60 | CH(CH₃)(CH₂)₃Ph | 5-carboxypyridin-2-yl | 148–50° | 73.63 | 6.45 | 3.58 | 73.45 | 6.39 | 3.65 |
| 61 | CH(CH₃)(CH₂)₃Ph | 3-carboxyphenyl | 72–4° | 76.90 | 6.71 | — | 77.08 | 6.49 | — |
| 62 | (CH₂)₄Ph | 5-carboxythiophen-2-yl | 118–9° | 69.07 | 5.81 | — | 68.75 | 5.61 | — |
| 63 | (CH₂)₄Ph | 5-carboxypyridin-2-yl | 188–9° | 73.18 | 6.15 | 3.71 | 72.93 | 6.11 | 3.69 |

-continued

|  | | Analysis | | | | | |
|---|---|---|---|---|---|---|---|
|  | | | Calculated (%) | | | Found (%) | |
| Ex. # | R² | ArCO₂H | M.P. °C. | C | H | N | C | H | N |
| 64 | (sec-butyl with phenylpropyl chain, CH₃) | (thiophene-CO₂H) | 122–4° | — | — | — | — | — | — |
| 65 | (norbornyl, R, (−)) | (3-benzoic acid) | oil | — | — | — | — | — | — |
| 66 | (norbornyl, S, (+)) | (3-benzoic acid) | oil | — | — | — | — | — | — |
| 67 | (norbornyl, R, (−)) | (4-benzoic acid) | 234–6° | 74.53 | 6.55 | — | 74.49 | 6.24 | — |
| 68 | (norbornyl, H, (+)) | (4-benzoic acid) | 234–6° | 74.53 | 6.55 | — | 74.53 | 6.17 | — |
| 69 | (norbornyl, R, (−)) | (2-naphthoic acid) | 242–4° | 77.30 | 6.23 | — | 77.28 | 6.25 | — |

-continued

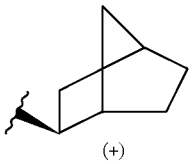

| Ex. # | R² | ArCO₂H | M.P. °C. | Calculated (%) C | H | N | Found (%) C | H | N |
|---|---|---|---|---|---|---|---|---|---|
| 70 | 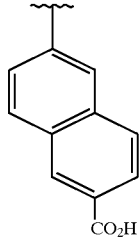 (+) | 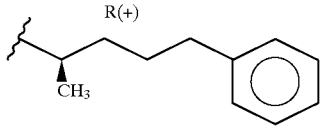 | 243–5° | — | — | — | — | — | — |
| 71 | 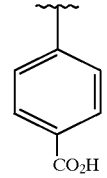 R(+) | 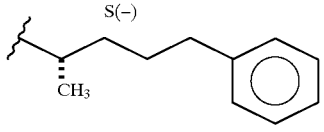 | 159–60° | 76.90 | 6.71 | — | 76.82 | 6.58 | — |
| 72 | 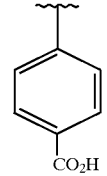 S(−) | 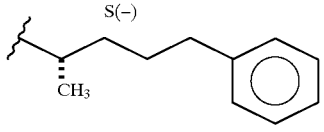 | 159–60° | 76.90 | 6.71 | — | 76.87 | 6.69 | — |

EXAMPLE 73

2-[(4-Methoxy-4'-nitro[1,1'-biphenyl]-3-yl)oxy]bicyclo[2.2.1]heptane

To a stirred solution of (2 g, 6.73 mmol, 1.0 eq) (±)-1-methoxy-2-exo-norbornyloxy-4-bromobenzene in 50 ml of dry THF at −78° C. was added 2.96 ml (7.40 mmol, 1.1 eq) 2.5M n-BuLi. After about 45 minutes at −78° C., (8.07 ml, 8.07 mmol, 1.2 eq) 1.0M ZnCl₂ in ether was added and the reaction mixture allowed to warm to room temperature over 30 minutes. Pd (PPh₃)₄ (389 mg, 0.34 mmol, 0.05 eq) and then (1.67 g, 6.73 mmol, 1.0 eq) 1-nitro-4-iodobenzene were added and the reaction mixture stirred 30 minutes at room temperature. The mixture was concentrated in vacuo and chromatographed on silica gel, eluting with ethyl acetate/hexane (0–8%).to afford 1.32 g, 58%, of a yellow solid. M.P.: 134°–135° C.

EXAMPLE 74

4'-Methoxy-3'-(1-methyl-4-phenyl-butoxy)-[1,1'-biphenyl]-4-tetrazole

A solution of (525 mg, 8.07 mmol, 1.2 eq) NaN₃ in 10 ml H₂O was added to a stirred solution of (1.8 ml, 6.70 mmol, 1.0 eq) of Bu₃SnCl in 75 ml of ether. The mixture was stirred 45 minutes at room temperature then the layers were separated and the aqueous layer extracted once with ether. The ether extracts were combined, washed once with brine, dried over MgSO₄, and concentrated to yield a clear, colorless oil, used directly in the next reaction.

To a mixture of (2.22 g, 6.7 mmol, 1.7 eq) crude Bu₃SnN₃ in 50 ml dry THF was added a solution (1.5 g, 4.04 mmol, 1.0 eq) of the nitrile (see Preparation 39) in 50 ml dry THF. The reaction mixture was heated to reflux and stirred for 4 days. The mixture was cooled, concentrated in vacuo, and chromatographed on silica gel eluting with hexane-ethyl acetate-acetic acid (75:24:1), then recrystallized from ethyl acetate-hexane to afford 565 mg, 34%, of an off white solid. M.P.: 139°–140° C.

EXAMPLE 75

4-[3-(Bicyclo[2.2.1]hept-2-yloxy)-4-methoxyphenoxy] benzoic acid

To a solution (1 g, 4.27 mmol, 1.0 eq) of 3-(bicyclo[2.2.1]hept-2-yloxy)-4-methoxy phenol and (0.63 ml, 4.27 mmol, 1.0 eq) ethyl-4-fluorobenzoate in 45 ml of dimethylacetamide was added (708 mg, 5.12 mmol, 1.2 eq) K₂CO₃. After heating to reflux for 18 hours, the reaction mixture was cooled to room temperature, poured into 75 ml of H₂O and extracted twice with ethyl acetate. The ethyl acetate extracts were combined, washed once with brine, dried over MgSO₄, and concentrated to give a dark brown oil. Chromatography on silica gel eluting with ethyl acetate-hexane (0–15%) gave 590 mg, 26%, of a light yellow oil.

A mixture of (750 mg, 1.96 mmol, 1.0 eq) of the above ester and 10 ml of 2N NaOH in 20 ml of ethanol was heated to reflux for 2 hours. The mixture was diluted with 50 ml of $H_2O$, acidified to pH 4 and extracted twice with ethyl acetate. The combined organic layers were washed once with brine, dried over $Na_2SO_4$, and concentrated to give an off-white solid. Recrystallization from ethyl acetate/hexane afforded 425 mg, 61%, of a white crystalline solid. M.P.: 116°–117° C. Elemental Analysis Calc'd for $C_{21}H_{22}O_5$: Calc'd: C, 71.16; H, 6.27. Found: C, 70.98; H, 6.18.

EXAMPLE 76

N-[3'-(Bicyclo[2.2.1]hept-2-yloxy)-4'-methoxy[1,1'-biphenyl]-4-yl]-1,1,1-trifluoromethanesulfonamide
and N,N-[3'-(Bicyclo[2.2.1]hept-2-yloxy)-4'-methoxy-[1,1'-biphenyl]-4-yl]-bis(1,1,1-trifluorodimethanesulfonamide)

To a mixture of (460 mg, 1.45 mmol, 1.0 eq) of 3'-(bicyclo[2.2.1]hept-2-yloxy)-4'-methoxy[1,1'-biphenyl]-4-amino and (0.24 ml, 1.74 mmol, 1.2 eq) triethylamine in 6 ml of $CH_2Cl_2$ at –78° C. was added 0.27 ml (1.60 mmol, 1.0 eq) of triflic anhydride dropwise. The reaction mixture was stirred 10 minutes at –78° C. and then 1.5 hours at 0° C. The mixture was concentrated in vacuo, costripped twice with $CHCl_3$ then chromatographed on silica gel eluting with ethyl acetate·hexane (10%→30%) to afford 187 mg, 22%, of N,N-[3'-(bicyclo[2.2.1]hept-2-yloxy)-4'-methoxy[1,1'-biphenyl]-4-yl]-1,1,1-trifluorodimethanesulfonamide and 70 mg, 11%, of N-[3'-(bicyclo[2.2.1]hept-2-yloxy)-4'-methoxyl[1,1'-biphenyl]-4-yl]-1,1,1-trifluoromethanesulfonamide. M.P. of the dimethanesulfonamide: 146°–147° C. M.P. of the methanesulfonamide: 138°–139° C. Dimethanesulfonamide Elemental Analysis Calc'd for $C_{22}H_{21}NO_6S_2F_6$: Calc'd: C, 46.07; H, 3.70; N, 2.44. Found: C, 46.21; H, 3.63; N, 2.51.

EXAMPLE 77

N-(3'-Bicyclo[2.2.1]hept-2-yloxy)-4-'-methoxy-[1,1'-biphenyl]-4-ylmethanesulfonamide To a stirred solution of (525 mg, 1.70 mmol, 1.0 eq) 3'-(bicyclo[2.2.1]hept-2-yloxy)-4'-methoxy[1,1'-biphenyl]-4-amino in 10 ml dry $CH_2Cl_2$ at 0° C. was added 0.28 ml of triethylamine (2.03 mmol, 1.2 eq), followed by 355 mg (2.03 mmol, 1.2 eq) methanesulfonic anhydride. The mixture was stirred at 0° C. for 10 minutes, then at room temperature for 1 hour, at which point an additional 200 mg (1.1 mmol, 0.7 eq) of methane sulfonic anhydride was added. After stirring an additional 30 minutes at room temperature, the reaction mixture was concentrated in vacuo, costripped twice with $CHCl_3$, and chromatographed on silica gel eluting with ethyl acetate-hexane (10–35%) to yield 700 mg of compound. Recrystallization from ethyl acetate/hexane afforded 650 mg, 98%, of crystals. M.P.: 151°–153° C. Elemental Analysis Calc'd for $C_{21}H_{25}NO_4S$: Calc'd: C, 65.08; H, 6.51; N, 3.61. Found: C, 64.92; H, 6.21; N, 3.53.

EXAMPLE 78

Methyl 1-[3-(Bicyclo[2.2.1]hept-2-yloxy)-4-methoxyphenyl]-1H-indole-3-carboxylate A mixture of (1.0 g, 5.71 mmol, 1.0 eq) 3-carbomethoxy indole, (2.21 g, 7.42 mmol, 1.3 eq) (±)-1-methoxy-2-exo-norbornyloxy-4-bromobenzene (30.7 mg, 0.107 mmol, 0.2 eq) cuprous bromide, and (866 mg, 6.27 mmol, 1.1 eq) potassium carbonate in 15 ml of 1-methyl-2-pyrrolidinone was heated to 150° C. for 24 hours. The reaction mixture was cooled, diluted with 350 ml of ethyl acetate and 350 ml of $H_2O$, and the layers separated. The aqueous layer was extracted twice with ethyl acetate. The ethyl acetate extracts were combined, washed twice with $H_2O$, once with brine, dried over $Na_2SO_4$ and concentrated in vacuo to give a light brown oil. Silica gel chromatography eluting with 20% ethyl acetatehexane gave 1.05 g, 47%, of a white foamy solid. M.P.: 120°–122° C. Elemental Analysis Calc'd for $C_{24}H_{25}NO_4$: Calc'd: C, 73.64; H, 6.44; N, 3.58. Found: C, 73.70; H, 6.37; N, 3.59.

EXAMPLE 79

1-[3-(Bicyclo[2.2.1]hept-2-yloxy)-4-methoxy]-1H-indole-3-carboxylic acid

A mixture of (0.85 g, 2.17 mmol, 1.0 eq) of methyl 1-[3-(bicyclo[2.2.1]-hept-2-yloxy)-4-methoxyphenyl]-1H-indole-3-carboxylic acid and 20 ml of 1N NaOH in 50 ml of $CH_3OH$ was heated to reflux for 18 hours. The reaction mixture was cooled, diluted with 150 ml of $H_2O$, and acidified to pH 1. The white precipitate that formed was filtered, washed with $H_2O$ and air dried to yield 0.68 g of a white solid. Recrystallization from ethyl acetate/hexane afforded 565 mg, 69%, of white powder. M.P.: 203°–205° C. Elemental Analysis Calc'd for $C_{23}H_{23}NO_4$: Calc'd: C, 73.64; H, 6.44; N, 3.58. Found: C, 73.01; H, 6.23; N, 3.66.

EXAMPLE 80

2-[3-(Cyclopentyloxy)-4-methoxyphenyl]-5-fluorobenzothiazole

A mixture of (440 mg, 2 mmoles) 4-methoxy-3-cyclopentyloxy benzaldehyde and (400 mg, 2.1 mmoles) 2-mercapto-5-fluoroaniline hydrochloride was heated on a steam bath for 15 minutes. The resulting thick orange oil was cooled and dissolved in 5 ml of 10% $FeCl_3$ in methanol and allowed to stir overnight. The reaction was diluted with water and extracted with $CH_2Cl_2$. The $CH_2Cl_2$ layer was dried and evaporated to give 760 mg of crude product which was purified on silica gel with $CH_2Cl_2$ to give 500 mg of product. Recrystallization from isopropanol gave 140 mg of product. M.P.: 96°–97° C. Elemental Analysis Calc'd for $C_{19}H_{18}O_2NSF$ : Calc'd: C, 66.45; H, 5.28; N, 4.08. Found: C, 66.44; H. 5.13; N. 4.06.

EXAMPLES 81–82

Reaction of the appropriate aldehyde with 2-mercapto-3-aminopyridine, analogous to the procedure of Example 80, yielded the following compounds of the formula

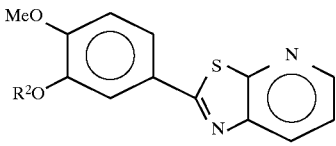

| | | | Analysis | | | | | |
|---|---|---|---|---|---|---|---|---|
| | | | Calculated % | | | Found % | | |
| Ex. # | R² | M.P. °C. | C | H | N | C | H | N |
| 81 | (cyclopentylmethyl) | 118–120° | 66.23 | 5.56 | 8.58 | 66.41 | 5.71 | 8.42 |
| 82 | (bicyclo[2.2.1]heptyl) | 110–111° | — | — | — | — | — | — |

EXAMPLE 83

1-[3-(Cyclopentyloxy)-4-methoxyphenyl]-1H-benzimidazole-5-carboxylic acid

A mixture of (800 mg, 5.3 mmoles) cyclopentyl bromide, (1.6 g, 5.3 mmoles) methyl 1-(3-hydroxy-4-methoxyphenyl)-1H-benzimidazole-5-carboxylate and 251 mg of 50% sodium hydride in 10 ml of dimethylformamide was stirred at 100° C. for 30 minutes. The reaction was cooled, poured onto H₂O and extracted with ethyl acetate. The ethyl acetate layer was dried and evaporated to give 2 g of crude product. Purification on silica gel with CH₂Cl₂ gave 1.1 g of methyl 1-(3-cyclopentyl-4-methoxyphenyl)-1H-benzimidazole-5-carboxylate. M.P.: 129°–131°.

A solution of 600 mg of the above methyl ester in 20 ml of methanol containing 6 ml of 1N NaOH was heated on a steam bath for 30 minutes. The reaction was cooled and the methanol removed in vacuo. The residue was acidified with 1N HCl and the resulting solid was filtered and recrystallized from methanol to give 198 mg of product. M.P. >250° C.

EXAMPLE 84

2-[3-(Cyclopentyloxy)-4-methoxy-phenyl]oxazolo[4,5-b]pyridine

A solution of 500 mg of 2-N[3-(cyclopentyloxy)-4-methoxyphenylcarbonyl]amino-3-hydroxypyridine in 15 ml of POCl₃ was heated at reflux for 20 hours. Excess POCl₃ was evaporated and the crude product was purified by chromatography on silica gel with CH₂Cl₂/methanol to give 165 mg of the title product. M.P.: 108°–109° C.

EXAMPLE 85

2-[3-(Cyclopentyloxy)-4-methoxy-phenyl]oxazolo[5,4b]pyridine

Reaction of 4-methoxy-3-cyclopentyloxybenzoic acid chloride with 2-hydroxy-3-amino pyridine, analogous to the procedure of Example 84 yielded the title compound. M.P.: 141°–142° C. Elemental Analysis Calc'd for C₁₈H₁₈N₂)₃: Calc'd: C, 69.66; H, 5.85; N, 9.03. Found: C, 69.51; H, 5.76; N. 8.90.

EXAMPLE 86

2-(3-Cyclopentyloxy-4-methoxyphenyl)thiazole

A solution of 130 mg of 3-cyclopentyloxy-4-methoxybenzthioamide and 100 mg of chloroacetaldehyde in 15 ml of ethanol was heated at reflux for 6 hours. The volatiles were evaporated and the residue purified on silica gel with CH₂Cl₂ to give 90 mg of product. M.P.: 72°–75° C.

EXAMPLE 87

2-(3-Cyclopentyloxy-4-methoxyphenyl)-5-thiazolecarboxylic acid

Reaction of 3-methoxy-4-cyclopentyloxybenzthioamide with chlorocarboethoxyacetaldehyde, analogous to the procedure of Example 86, yielded the ethyl ester of the title compound, which was hydrolyzed under basic conditions to yield the title compound. M.P.: 170°–171° C.

EXAMPLE 88

4-[3-(Bicyclo[2.2.1]hept-2-yloxy)-4-methoxyphenyl]-2-thiazolacetic acid

A solution of (660 mg, 6.5 mmoles) of 4-3-(bicyclo[2.2.1]hept-2-yloxy)-4-methoxyphenyl]-2-methylthiazole in THF was added dropwise to a solution of lithium diisopropylamide in THF at −78° C. After 1 hour at −78° C. dry CO₂ was bubbled into the reaction for 2 minutes. The reaction was allowed to warm to room temperature, acidified with dilute HCl and extracted with ethyl acetate. The ethyl acetate layer was dried and evaporated to give 420 mg product. Recrystallization from hexane 290 mg product. M.P.: 190°–191° C.

EXAMPLE 89

4-[3-(Bicyclo[2.2.1]hept-2-yloxy)-4-methoxyphenyl-2-thiazolecarboxylic acid

Reaction of the chloroketone of Preparation 43 with ethyl thiooxanate, analogous to the procedure of Example 88, yielded the ethyl ester of the title compound which was then hydrolyzed according to the procedure of Example 8 to give the title compound. M.P.: 112°–113° C.

EXAMPLE 90

4-[3-Bicyclo[2.2.1]hept-2-yloxy-4-methoxyphenyl]-2-thiazolamine

Reactions of the chloroketone of Preparation 43 with thiourea, analogous to the procedure of Example 88, yielded the title compound. M.P.: 168°–178° C.

EXAMPLE 91

1-[3-(Cyclopentyloxy)-4-methoxyphenyl]-1H-imidazo[4,5-c]pyridine

A solution of 2.05 g of 1-(3hydroxy-4-methoxyphenyl)-1H-imidazo[4,5-c]pyridine, 2.5 g of cyclopentylbromide and 665 mg of NaH in 20 ml of DMF was stirred at room temperature overnight. The reaction was poured into water and extracted with ethyl acetate, dried to give 1.4 g of crude product. Recrystallization from $CH_2Cl_2$ gave 574 mg product. M.P.: 66°–88° C.

EXAMPLE 92

1-[3-(Cyclopentyloxy)-4-methoxyphenyl]-2-methyl-1H-imidazo[4,5-c]pyridine

Reaction of 3-hydroxy-4-methoxy-N-[4-(3-amino)pyridinyl]aniline with acetic acid, analogous to the procedure of Preparation 44, and subsequent reactions with cyclopentylbromide analogous to the procedure of Example 91, yielded the title compound. M.P.: 144°–145° C.

EXAMPLE 93

1-[3-(Cyclopentyloxy)-4-methoxyphenyl]-2-ethyl-1H-imidazo[4,5-c]pyridine

Reaction of 3-hydroxy-4-methoxy-N-[4-(3-amino)pyridinyl]aniline with propionic acid analogous to the procedure of Preparation 44, and subsequent reaction with cyclopentylbromide, analogous to the procedure of Example 91, yielded the title compound.

EXAMPLE 94

2-[3-[2-indoxy]-4-methoxyphenyl]-1H-imidazo[4,5-b]pyridine

A. Preparation of 3-(2-indoxy)-4-methoxybenzoic acid

To a magnetically stirred solution of 3-(2-indoxy)-4-methoxybenzaldehyde (3.0 g, 11.2 mmoles) in acetone (50 ml) was added 7 ml of 2.67M solution of $Cr_2O_3$ in 50% aqueous $H_2SO_4$. This was exothermic enough to effect a mild reflux of acetone, and no external cooling was necessary. After stirring overnight at ambient temperature, 50 ml of $H_2O$ was added, and the acetone was allowed to evaporate over a steam bath. The crude product was filtered and washed with 1N HCl followed by water. Recrystallization from isopropyl ether gave 1.9 g of off-white crystals. M.P.: 189°–191° C.

B. Preparation of 3-(2-indoxy)-4-methoxybenzoyl chloride

A solution of 0.50 g of 3-(2-indoxy)-4-methoxybenzoic acid in 10 ml of thionyl chloride was heated at reflux for 1 hour. Removal of the volatiles under reduced pressure gave a dull pink solid which was immediately used in the next step without purification.

C. Preparation of the title compound

To a magnetically stirred solution of 2,3-aminopyridine (1.8 mmole) in dry pyridine (15 ml) at 0° C. was added dropwise a solution of 3-(2-indoxy)-4-methoxybenzoyl chloride in dry THF (10 ml). After 1 hour the mixture was warmed to ambient temperature and after 16 hours the volatiles were removed under reduced pressure. The residue was suspended in 25 ml of water, filtered, and washed with water to give 0.59 g of a white solid. M.P.: 226°–228° C. (dec).

The above amide was suspended in 10 ml of phosphorous oxychloride and heated at reflux for 1.5 hours, at which time the reaction mixture was homogeneous. The volatiles were removed under reduced pressure, and the residue was suspended in 25 ml of saturated sodium bicarbonate, filtered, and air-dried. Column chromatography followed by recrystallization from ethanol gave 180 mg of off-white crystals. M.P.: 206°–208° C. Elemental analysis calculated for $C_{22}H_{19}O_2N_3$: C, 73.93; H, 5.36; N, 11.76. Found: C, 73.01; H, 5.06; N, 11.76.

EXAMPLE 95

2-[3-[2-Indoxy]-4-methoxyphenyl]thiazo[5,4-b]pyridine

A. Preparation of 3-amino-2-thiopyridine

A mixture of 3-amino-2-chloropyridine (25 g, 190 mmoles), sodium hydrogen sulfide (58 g, 780 mmoles) and propylene glycol (75 ml) were heated at reflux for 5 hours. The solvent was removed under reduced pressure, and the resulting residue was dissolved in 300 ml of water and acidified to pH 5 with AcOH. After stirring for 1 hour the mixture was filtered to give 14.3 g of a dark brown solid. Recrystallization from toluene provided dark brown needles. M.P.: 131°–132° C.

B. Preparation of the title compound

To a magnetically stirred solution of 3-amino-2-thiopyridine (0.22 g) in dry pyridine (15 ml) at 0° C. was added dropwise a solution of 3-(2-indoxy)-4-methoxybenzoyl chloride (0.50 g) in dry THF (10 ml). After 1 hour the mixture was warmed to ambient temperature and after 16 hours the volatiles were removed under reduced pressure. The residue was suspended in 25 ml of water, filtered, and washed with water to give 0.60 g of a gold solid. M.P.: 252°–253° C. (dec).

The above amide (0.58 g, 1.5 mmoles) and $POCl_3$ (10 ml) were heated at reflux. After 1.5 hours the mixture was slowly poured into water, cooled, and extracted with ether. The combined organics were dried over $MgSO_4$ and concentrated to give a pale yellow solid. Recrystallization from methanol gave 0.32 g of product as its HCl salt. The salt was dissolved in methylene chloride and washed with 1N NaOH to give a white solid. Recrystallization from methanol gave 0.25 g of a white solid. M.P.: 159°–160° C. Elemental analysis calculated for $C_{22}H_{18}O_2N_2S$: C, 70.57; H, 4.84; N, 7.48. Found: C, 70.46; H, 4.72; N, 7.35.

EXAMPLE 96

2-[3-[2-Indoxy]-4-methoxyphenyl]oxazo[5,4-b]pyridine

A. Preparation of 3-amino-2-pyridone

3-Nitro-2-pyridone (2.0 g, 14 mmoles), 10%, Pd/C (0.20 g) and methanol (50 ml) were placed on a Parr shaker under 45 psi of $H_2$. After 18 hours the mixture was filtered and concentrated to give 1.3 g of a pale pink solid. M.P.: 123°–125° C.

B. Preparation of the title compound

To a magnetically stirred solution of 3-amino-2-hydroxypyridine (1.8 mmole) in dry pyridine (15 ml) at 0° C. was added dropwise a solution of 3-(2-indoxy)-4-methoxybenzoyl chloride in dry THF (10 ml). After 1 hour the mixture was warmed to ambient temperature and after 16 hours the volatiles were removed under reduced pressure. The residue was suspended in 25 ml of water, filtered, and washed with water to give 0.57 g of a white solid. M.P.: 282°–284° C. (dec).

The above amide was suspended in 10 ml of phosphorous oxychloride and heated at reflux for 1.5 hours, at which time the reaction mixture was homogeneous. The volatiles were removed under reduced pressure, and the residue was suspended in 25 ml of saturated sodium bicarbonate, filtered, and air-dried. Column chromatography (silica, 1:3 EtOAc/hexane) gave 160 mg of a white solid. M.P.: 193°–194° C.

EXAMPLE 97

4'-Methoxy-3'-(4-phenylbutoxy)-(±)[1,1'-biphenyl]-4-carboxamide

A suspension of (0.522 g, 1.38 mmoles) 4-[4-methoxy-3-(4-phenylbutyl-oxy)phenyl]benzoic acid in dry methylene chloride was treated with excess thionyl chloride (0.505 ml, 6.93 mmoles) and a catalytic amount of anhydrous DMF (3–5 drops). The resulting clear solution was heated to reflux under nitrogen atmosphere for 1 hour. The methylene chloride was removed in vacuo and the resulting light yellow solid residue azeotroped with additional 15 ml of dry methylene chloride. The residue was dissolved in 15 ml of dry $CH_2Cl_2$, cooled to 0° C. (ice bath) and dry anhydrous ammonia gas bubbled directly into the reaction mixture for approximately 5 minutes. This was followed by allowing the reaction to stir at 0° C. for an additional hour, after which time the reaction mixture was diluted with 500 ml of ethyl acetate and 300 ml of $H_2O$. The organic layer was separated and washed with 1N HCl (2×350 ml), 2N NaOH (2×350 ml), water (1×300 ml), brine, dried over $MgSO_4$ and evaporated under reduced pressure which yielded a white solid. Recrystallization from ethyl acetate-hexane gave a total of 0.37 grams of white crystals. M.P.: 180°–182° C. Elemental Analysis Calc'd for $C_{24}H_2O_3N$: Calc'd: C, 76.77; H, 6.71; N, 3.73. Found: C, 76.93; H, 6.71; N, 3.73.

EXAMPLE 98–104

Reaction id the appropriate carboxylic acid with the required amine of the general formula $NR_1R_2$, analogous to the procedure of Example 97, yielded the following compounds:

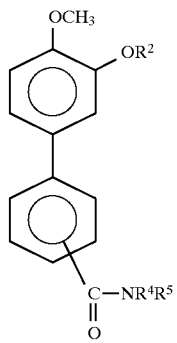

| | | | | | | Analysis | | | | | |
| | | | | | | Calculated % | | | Found % | | |
| Ex. # | $R^2$ | $R^4$ | $R^5$ | Position of Amide | M.P. °C. | C | H | N | C | H | N |
|---|---|---|---|---|---|---|---|---|---|---|---|
| 98 | (R-CH₃, phenylbutyl, one stereo) | H | H | Para | 183–184° | — | — | — | — | — | — |
| 99 | (S-CH₃, phenylbutyl, other stereo) | H | H | Para | N.T. | 77.09 | 6.49 | 3.60 | 76.75 | 6.67 | 3.55 |
| 100 | (norbornyl) | $CH_2CH_3$ | $CH_2CH_3$ | Meta | 112–114° | 76.30 | 7.94 | 3.58 | 76.55 | 8.22 | 3.61 |
| 101 | (CH₃, phenylbutyl) | H | H | Para | 169–171° | 77.08 | 7.08 | 3.59 | 77.07 | 6.95 | 3.59 |

-continued

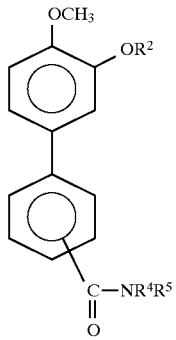

| Ex. # | R² | R⁴ | R⁵ | Position of Amide | M.P. °C. | Calculated % C | H | N | Found % C | H | N |
|---|---|---|---|---|---|---|---|---|---|---|---|
| 102 | (S)-CH(CH₃)-CH₂CH₂CH₂-phenyl | H | CH₃ | Para | 98–100° | 77.39 | 7.24 | 3.47 | 77.31 | 7.24 | 3.45 |
| 103 | norbornyl | H | H | Meta | 151–153° | 74.75 | 6.87 | 4.15 | 74.47 | 6.97 | 4.00 |
| 104 | norbornyl | H | H | Para | 245–247° | — | — | — | — | — | — |

EXAMPLE 105

N-(2-Methylphenyl)sulphonyl 4'-methoxy-3'-(1-methyl-4-phenylbutoxy)-(±)[1,1'-biphenyl]-4-carboxamide, To a solution of acid 4'-methoxy-3'-(1-methyl-4-phenylbutoxy)-(±)[1,1'-biphenyl]-4-carboxylic acid, (0.257 g, 0.658 mmoles) in 10 ml of anhydrous methylene chloride under hydrogen atmosphere was added dimethylamino pyridine (88.46 mg, 0.728 mmoles); o-Toluenesulfonamide (0.122 g, 0.712 mmoles) and dicyclohexylcarbodiimide (0.124 g, 0.6 mmoles) the reaction mixture allowed to stir for 50 hours. The solvent was evaporated and the resulting solid triturated with methylene chloride:ether (~1:1) which lead to precipitation of by-product DCU which was filtered. Concentration of the mother liquor followed by 3 g additional triturations with ethyl acetate/ether (~1:1) caused additional deposit of white solid which was filtered. The clear filtrate was concentrated and purified on a silica gel column using methylene chloride/methanol as eluant (95:5). Concentration of fractions containing desired products gave a total of 0.37 g of white foamy solid. Recrystallization from ethyl acetate/hexane gave 0.208 grams of white solid. M.P.: 97°–100° C.

EXAMPLE 106

2-[3-[4-(4-Methoxyphenyl)butoxy]-4methoxyphenyl]-1H-benzimidazole-5-carboxylic Acid 3-(4-(4-Methoxyphenyl)-butoxy)-4-methoxybenzaldehyde (2.8 g) and 3,4-diaminobenzoic acid (1.4 g) were heated to about 120° C. over 1 hour. The resulting residue was chromatographed on a 5×10 cm pad of silica gel eluting with ether to give 1.4 g of a beige solid which was recrystallized from 20 ml of methanol. M.P. 167°–169° C. MS m/e 450 (M⁺+1). Elemental analysis calculated for $C_{26}H_{28}O_5N_2$: C, 69.62; H, 6.29; N, 6.24. Found: C, 69.72; H. 6.70; N, 5.75.

EXAMPLE 107–211

Additional examples which were prepared according to the methods described and readily apparent to those skilled in the art are shown in the following table.

| Ex. # | R¹ | R² | A | Y | B | Z-R³ | M.P. (°C.) |
|---|---|---|---|---|---|---|---|
| 107 | CH₃ | indanyl | C.B. | C.B. | C.B. | 4-COOH-phenyl | 244–247 |
| 108 | CH₃ | indanyl | C.B. | C.B. | C.B. | 5-OCH₃-pyridazin-2-yl (N=N) | 119–122 dec. |
| 109 | CH₃ | 4-phenylbutyl | C.B. | C.B. | C.B. | 5-COOH-thien-2-yl | 118–119 |
| 110 | CH₃ | 4-phenylbutyl | C.B. | C.B. | C.B. | 5-COOH-pyridin-2-yl | 188–189 |
| 111 | CH₃ | indanyl | C.B. | C.B. | C.B. | 4-CN-phenyl | 199–201 |
| 112 | CH₃ | indanyl | C.B. | C.B. | C.B. | 4-CONH₂-phenyl | 237–239 |
| 113 | CH₃ | indanyl | C.B. | C.B. | C.B. | 4-CH₂NH₂-phenyl | 128–129 |
| 114 | CH₃ | 4-phenylbut-2-yl | C.B. | C.B. | C.B. | 5-COOH-thien-2-yl | 122–124 |

-continued

| Ex. # | R¹ | R² | A | Y | B | Z-R³ | M.P. (°C.) |
|---|---|---|---|---|---|---|---|
| 115 | CH₃ | (4-phenylpentyl) | C.B. | C.B. | (1,4-phenylene) | (tetrazole) | 139–140 |
| 116 | CH₃ | (6-phenylhexyl) | C.B. | C.B. | C.B. | (4-CH=CH-COOH phenyl) | 190–191 |
| 117 | CH₃ | (6-phenylhexyl) | C.B. | C.B. | C.B. | (3-CH=CH-COOH phenyl) | 85–87 |
| 118 | CH₃ | (4-phenylpentyl) | C.B. | C.B. | C.B. | (4-CONH₂ phenyl) | 183–184 |
| 119 | CH₃ | (4-phenylpentyl) | C.B. | C.B. | C.B. | (4-CONH₂ phenyl) | 182–184 |
| 120 | CH₃ | (norbornyl) | C.B. | C.B. | C.B. | (4-CON(Et)₂ phenyl) | 112–114 |

-continued

| Ex. # | R¹ | R² | A | Y | B | Z-R³ | M.P. (°C.) |
|---|---|---|---|---|---|---|---|
| 121 | CH₃ | (CH₂)₆-phenyl | C.B. | C.B. | C.B. | 4-COOH, 3-NO₂ phenyl | 124–125 |
| 122 | CH₃ | (CH₂)₆-phenyl | C.B. | C.B. | C.B. | 4-COOH, 3-CH₃ phenyl | 127–128 |
| 123 | CH₃ | (CH₂)₆-phenyl | C.B. | C.B. | C.B. | 4-COOH, 3-Cl phenyl | 127–128 |
| 124 | CH₃ | (CH₂)₄-phenyl | C.B. | C.B. | C.B. | 4-CONH₂ phenyl | 178–180 |
| 125 | CH₃ | CH(CH₃)(CH₂)₃-phenyl | C.B. | C.B. | C.B. | 4-C(O)N(H)CH₃ phenyl | 98–100 |
| 126 | CH₃ | norbornyl | C.B. | C.B. | C.B. | 3-CONH₂ phenyl | 151–153 |
| 127 | CH₃ | norbornyl | C.B. | C.B. | C.B. | 4-CONH₂ phenyl | 245–247 |

-continued

| Ex. # | R¹ | R² | A | Y | B | Z-R³ | M.P. (°C.) |
|---|---|---|---|---|---|---|---|
| 128 | CH₃ | (S)-1-methyl-3-phenylpropyl | C.B. | C.B. | C.B. | 3-COOH-phenyl | 47–50 |
| 129 | CH₃ | norbornyl | C.B. | C.B. | C.B. | 5-CONH₂-pyridin-3-yl | 169–171 |
| 130 | CH₃ | 4-phenylbutyl | C.B. | C.B. | C.B. | 4-CONH₂-3-CH₃-phenyl | 153–154 |
| 131 | CH₃ | (S)-1-methyl-3-phenylpropyl (+) | C.B. | C.B. | C.B. | 3-CONH₂-phenyl | 88–90 |
| 132 | CH₃ | 4-phenylbutyl | C.B. | C.B. | C.B. | 3-COOH-phenyl | 110–112 |
| 133 | CH₃ | 4-(4-OCH₃-phenyl)butyl | C.B. | C.B. | C.B. | 4-COOH-phenyl | 171–172 |

-continued

| Ex. # | R[1] | R[2] | A | Y | B | Z-R[3] | M.P. (°C.) |
|---|---|---|---|---|---|---|---|
| 134 | CH$_3$ | –(CH$_2$)$_5$–C$_6$H$_4$–OCH$_3$ (para) | C.B. | C.B. | C.B. | 4-COOH, 3-CH$_3$ phenyl | 139–140 |
| 135 | CH$_3$ | –(CH$_2$)$_6$–C$_6$H$_5$ | C.B. | C.B. | C.B. | 3-(CH=CH–CONH$_2$) phenyl | 145–146 |
| 136 | CH$_3$ | –(CH$_2$)$_6$–C$_6$H$_5$ | C.B. | C.B. | C.B. | 4-OCH$_3$, 3-COOH phenyl | 72–73 |
| 137 | CH$_3$ | –(CH$_2$)$_5$–C$_6$H$_5$ | C.B. | C.B. | C.B. | 3-CONH$_2$ phenyl | 117–119 |
| 138 | CH$_3$ | –(CH$_2$)$_7$–C$_6$H$_5$ | C.B. | C.B. | C.B. | 4-Cl, 3-COOH phenyl | 54–55 |
| 139 | CH$_3$ | –(CH$_2$)$_7$–C$_6$H$_5$ | C.B. | C.B. | C.B. | 4-Cl, 3-CONH$_2$ phenyl | 165–166 |

-continued
| Ex. # | R¹ | R² | A | Y | B | Z-R³ | M.P. (°C.) |
|---|---|---|---|---|---|---|---|
| 140 | CH₃ |  | C.B. | C.B. | C.B. |  | 177–178 |
| 141 | CH₃ | 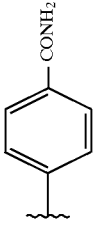 | C.B. | C.B. | C.B. | 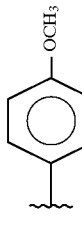 | 141–142 |
| 142 | CH₃ |  | C.B. | C.B. | C.B. |  | 124–125 |
| 143 | CH₃ |  | C.B. | C.B. | C.B. |  | 120–123 |
| 144 | CH₃ | 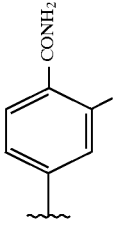 | C.B. | C.B. | C.B. | 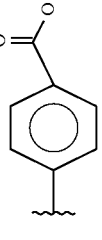 | 116–118 |
| 145 | CH₃ |  | C.B. | C.B. | C.B. |  | 99–101 |

-continued

| Ex. # | R¹ | R² | A | Y | B | Z-R³ | M.P. (°C.) |
|---|---|---|---|---|---|---|---|
| 146 | CH₃ | (phenyl-(CH₂)₃-CH(CH₃)-) | C.B. | C.B. | C.B. | 4-(N,N-dimethylcarbamoyl)phenyl | Mass Spectra M⁺ = 418 |
| 147 | CH₃ | (4-methoxyphenyl-(CH₂)₄-) | C.B. | C.B. | C.B. | 2-methoxy-5-pyridazinyl (N=N) | 83–84 |
| 148 | CH₃ | (phenyl-(CH₂)₆-) | C.B. | C.B. | C.B. | 2-hydroxy-5-carboxyphenyl | 118–121 |
| 149 | CH₃ | (phenyl-(CH₂)₂-C(cyclopropyl)-) | C.B. | C.B. | C.B. | 4-carboxyphenyl | 141–142 |
| 150 | CH₃ | (phenyl-(CH₂)₂-C(cyclopropyl)-) | C.B. | C.B. | C.B. | 3-methyl-4-carboxyphenyl | 157–158 |
| 151 | CH₃ | (phenyl-(CH₂)₄-) | C.B. | C.B. | C.B. | 3-fluoro-4-carboxyphenyl (linked via O) | 116–118 |

-continued

| Ex. # | R¹ | R² | A | Y | B | Z-R³ | M.P. (°C.) |
|---|---|---|---|---|---|---|---|
| 152 | CH₃ | (1-phenethylcyclopropyl) | C.B. | C.B. | C.B. | 4-CONH₂-phenyl | 154–155 |
| 153 | CH₃ | (S)-4-phenylbutan-2-yl | C.B. | C.B. | C.B. | 4-COOH-3-CH₃-phenyl | 128–130 |
| 154 | CH₃ | 6-phenylhexyl | C.B. | C.B. | C.B. | 2-COOH-4-COOH-phenyl | 173–175 |
| 155 | CH₃ | 6-phenylhexyl | C.B. | C.B. | C.B. | 4-COOH-3-CH₃-phenyl | 124–125 |
| 156 | CH₃ | 6-phenylhexyl | C.B. | C.B. | C.B. | 4-CONH₂-3-CF₃-phenyl | 164–165 |
| 157 | CH₃ | 6-(4-fluorophenyl)hexyl | C.B. | C.B. | C.B. | 4-COOH-3-CH₃-phenyl | 132–133 |

-continued

| Ex. # | R¹ | R² | A | Y | B | Z-R³ | M.P. (°C.) |
|---|---|---|---|---|---|---|---|
| 158 | CH₃ | (chain with CH₃ stereocenter, phenyl end) | C.B. | C.B. | C.B. | 4-CONH₂, 3-CF₃ phenyl | 79–81 |
| 159 | CH₃ | (alkyl chain, phenyl end) | C.B. | C.B. | C.B. | 4-COOH, 3-propyl phenyl | 123–124 |
| 160 | CH₃ | (alkyl chain, 4-OCH₃ phenyl end) | C.B. | C.B. | C.B. | 4-C(O)OCH₃ phenyl | Mass Spectra m/e = 420 |
| 161 | CH₃ | (alkyl chain, phenyl end) | C.B. | C.B. | C.B. | 4-C(O)OCH₃, 3-CH₃ phenyl | Mass Spectra m/e = 418 |
| 162 | CH₃ | (alkyl chain, phenyl end) | C.B. | C.B. | C.B. | 4-NH₂ phenyl | 103–104 |
| 163 | CH₃ | (alkyl chain, phenyl end) | C.B. | C.B. | C.B. | 4-COOH, 3-CF₃ phenyl | 103–105 |

-continued

| Ex. # | R¹ | R² | A | Y | B | Z-R³ | M.P. (°C.) |
|---|---|---|---|---|---|---|---|
| 164 | CH₃ | 4-fluorophenoxy-butyl | C.B. | C.B. | C.B. | 4-COOH-3-CH₃-phenyl | 136–138 |
| 165 | CH₃ | 5-phenylpentyl | C.B. | C.B. | C.B. | 4-COOH-3-ethyl-phenyl | 113–114 |
| 166 | CH₃ | 5-phenylpentyl | C.B. | C.B. | C.B. | 3-COOH-6-OCH₃-phenyl | 141–142 |
| 167 | CH₃ | 5-phenylpentyl | C.B. | C.B. | C.B. | 3-COOH-6-CH₃-phenyl | 135–136 |
| 168 | CH₃ | 5-phenylpentyl | —CH₂— | C.B. | C.B. | benzothiazol-2-yl | 64–66 |
| 169 | CH₃ | cyclopentylmethyl | —CH₂— | C.B. | C.B. | 4-OH-3-methyl-6-methoxychroman-4-yl | 104–108 |

-continued

| Ex. # | R[1] | R[2] | A | Y | B | Z-R[3] | M.P. (°C.) |
|---|---|---|---|---|---|---|---|
| 170 | CH₃ | cyclopentyl | —CH₂— | C.B. | C.B. | 4-(6-methoxychroman-4-ol), (+) | 97–99 |
| 171 | CH₃ | norbornyl | —CH₂— | C.B. | C.B. | 4-(6-methoxychroman-4-ol), (+) | 144–146 |
| 172 | CH₃ | norbornyl (R) | —CH₂— | C.B. | C.B. | 4-(6-methoxychroman-4-ol), (−) | 145–147 |
| 173 | CH₃ | norbornyl | C.B. | C.B. | —CH₂— | 4-(6-methoxychroman-4-ol), (+) | 145–147 |
| 174 | CH₃ | norbornyl (S) | C.B. | C.B. | —CH₂— | 4-(6-methoxychroman-4-ol), (−) | 144–146 |

-continued

| Ex. # | R[1] | R[2] | A | Y | B | Z-R[3] | M.P. (°C.) |
|---|---|---|---|---|---|---|---|
| 175 | CH₃ | (norbornyl, +) | —CH₂— | —O— | p-tolyl | N-pentyl-benzimidazolyl | 129–131 |
| 176 | CH₃ | (norbornyl, −) | —CH₂— | —O— | p-tolyl | N-pentyl-benzimidazolyl | 138–140 |
| 177 | CH₃ | (6-phenylhexyl) | —CH₂— | —NH— | C.B. | thiazolyl | Mass Specta e/z = 383 |
| 178 | CH₃ | (6-phenylhexyl) | —CH₂— | —NH— | C.B. | thiazolyl | 92–93 |
| 179 | CH₃ | (indanyl) | C.B. | C.B. | C.B. | nitro-pyridyl-oxazolyl | 228–229 |
| 180 | CH₃ | (indanyl) | C.B. | C.B. | C.B. | pyrazolyl | 118–119 |

-continued

| Ex. # | R¹ | R² | A | Y | B | Z-R³ | M.P. (°C.) |
|---|---|---|---|---|---|---|---|
| 181 | CH₃ | (2-indanyl) | C.B. | C.B. | C.B. | pyrazol-1-yl | 110–112 |
| 182 | CH₃ | (2-indanyl) | C.B. | C.B. | C.B. | 5-COOH-benzimidazol-2-yl | 185–187 |
| 183 | CH₃ | (norbornyl) | C.B. | C.B. | C.B. | 7-COOH-benzimidazol-2-yl | 229–230 |
| 184 | CH₃ | (2-indanyl) | C.B. | C.B. | C.B. | 5-COOH-imidazo[4,5-b]pyridin-2-yl | 301–302 dec. |
| 185 | CH₃ | -(CH₂)₅-Ph | C.B. | C.B. | C.B. | imidazol-1-yl | |
| 186 | CH₃ | -(CH₂)₅-Ph | C.B. | C.B. | C.B. | 2-methylimidazol-1-yl | |
| 187 | CH₃ | -(CH₂)₅-Ph | C.B. | C.B. | C.B. | 4-methylimidazol-1-yl | 71–72 |

-continued

| Ex. # | R¹ | R² | A | Y | B | Z-R³ | M.P. (°C.) |
|---|---|---|---|---|---|---|---|
| 188 | CH₃ | (2-indanyl) | C.B. | C.B. | C.B. | (maleimide-like diamide) | 241–242 |
| 189 | CH₃ | (2-indanyl) | C.B. | C.B. | C.B. | 5-CONH₂-benzimidazol-2-yl | 156–158 |
| 190 | CH₃ | 6-phenylhexyl | C.B. | C.B. | C.B. | thiazolo[5,4-b]pyridin-2-yl | 101–102 |
| 191 | CH₃ | 6-(4-methoxyphenyl)hexyl | C.B. | C.B. | C.B. | imidazol-1-yl | 73–74 |
| 192 | CH₃ | 6-(4-methoxyphenyl)hexyl | C.B. | C.B. | C.B. | thiazolo[5,4-b]pyridin-2-yl | 138–140 |
| 193 | CH₃ | 6-(4-methoxyphenyl)hexyl | C.B. | C.B. | C.B. | 5-COOH-benzimidazol-2-yl | 145–147 |
| 194 | CH₃ | 6-phenylhexyl | C.B. | C.B. | C.B. | 2-butyl-5-COOH-benzimidazol-1-yl | 146–148 |

-continued

| Ex. # | R¹ | R² | A | Y | B | Z-R³ | M.P. (°C.) |
|---|---|---|---|---|---|---|---|
| 195 | CH₃ | 4-fluorophenyl-(CH₂)₆- | C.B. | C.B. | C.B. | imidazol-1-yl | Mass Spectra e/z = 355 |
| 196 | CH₃ | phenyl-(CH₂)₆- | C.B. | C.B. | C.B. | 4-(N-(carboxymethyl)amino)phenyl | High Resolution Mass Spectra Calc'd: 405.19401 Found: 405.19316 |
| 197 | CH₃ | cyclopentyl- | C.B. | C.B. | C.B. | 5-carboxy-benzimidazol-2-yl | 210 |
| 198 | CH₃ | norbornyl- | C.B. | C.B. | C.B. | 5-(methoxycarbonyl)-benzimidazol-2-yl | 260–262 |
| 199 | CH₃ | norbornyl- | C.B. | C.B. | C.B. | 5-carboxy-benzimidazol-2-yl | 221–223 |
| 200 | CH₃ | 4-fluorophenoxy-(CH₂)₅- | C.B. | C.B. | C.B. | imidazol-1-yl | 68–71 |

-continued

| Ex. # | R[1] | R[2] | A | Y | B | Z-R[3] | M.P. (°C.) |
|---|---|---|---|---|---|---|---|
| 201 | CH₃ | cyclopentylmethyl | C.B. | C.B. | —CH₂— | chroman with OH, OCH₃ phenyl (−) | 105–107 |
| 202 | CH₃ | 6-phenylhexyl | C.B. | C.B. | —CH₂— | chroman with OH, CH₃O (+) | 115–119 |
| 203 | CH₃ | 6-phenylhexyl | C.B. | C.B. | —CH₂— | chroman with OH, CH₃O (−) | 115–119 |
| 204 | CH₃ | 6-phenylhexyl | C.B. | C.B. | —CH₂— | chroman with OH, CH₃O (±) | 96–98 |
| 205 | CH₃ | (S)-4-phenyl-2-methylbutyl | C.B. | C.B. | C.B. | cyclic urea | 131–133 |
| 206 | CH₃ | norbornyl | C.B. | C.B. | C.B. | imidazo[4,5-b]pyridine | 153–154 |

-continued

| Ex. # | R[1] | R[2] | A | Y | B | Z-R[3] | M.P. (°C.) |
|---|---|---|---|---|---|---|---|
| 207 | CH₃ | cyclopentyl | C.B. | C.B. | C.B. | thiazole-COOH | 123–125 |
| 208 | CH₃ | norbornyl | C.B. | C.B. | C.B. | thiazole-CH₃ | 81–82 |
| 209 | CH₃ | cyclopentyl | C.B. | C.B. | C.B. | thiazolopyridinone | 244–247 |
| 210 | CH₃ | cyclopentyl | C.B. | C.B. | C.B. | thiazolopyridinone | 226–228 |
| 211 | CH₃ | phenethyl | C.B. | C.B. | C.B. | benzimidazole-COOH | 261–262 |

*C.B. = Covalent Bond

EXAMPLE 212

4-(4-Methoxy3-(5-phenylpentyloxy)phenyl-2-methylbenzohydroxamic acid

A solution of 2-methyl-4-[4-methoxy-3-(5-phenylpentyloxy)phenyl]benzoic acid (0.13 g, 0.32 mmoles) in oxalyl chloride (5 ml) was heated to reflux under nitrogen for about 10 minutes. The solution was concentrated under reduced pressure and the residue dried at about 25° C. (0.05 mm pressure). The residue was then dissolved in dry THF (5 ml) and added slowly to a solution of hydroxylamine hydrochloride (0.022 g, 0.32 mmoles) in pyridine at about 0° C. After stirring at about 25° C. for about 16 hours the volatiles were removed under reduced pressure and the residue was slurried in 1NHCl. The mixture was then extracted with ethyl acetate and the combined organics were washed with water and brine, and dried over $MgSO_4$. Filtration followed by concentration under reduced pressure yielded a beige solid. Recrystallization from isopropyl ether (10 ml) gave 0.055 grams of the title compound as an off-white solid. M.P. 125°–126°C.; analysis calc'd. for $C_{26}H_{29}NO_4$: C,74.43; H, 6.97; N, 3.34. Found: C, 73.85; H, 6.78; N, 3.34.

EXAMPLE 213

2-[4-Methoxy-3-(5-phenylpentyloxy)phenyl]- 1H-benzimidazol-5-carboxylic acid A solution of 4-methoxy-3-(5-phenylpentoxy)-benzoic acid (5.0 grams, 15.9 mmole) in thromyl chloride (20 ml) was heated to reflux for about 1 hour. The mixture was concentrated under reduced pressure and the residue was dissolved in dry THF (20 ml) and added to a stirred solution of methyl-3,4-diaminobenzoate in pyridine (20 ml) at about 0° C. After about 1 hour the mixture was concentrated under reduced pressure and 1NHCl (50 ml) was added. The resulting mixture was extracted with ethylacetate (100 ml×3) and the combined organics were washed with water and brine, dried over sodium sulfate, filtered and concentrated under reduced pressure to give 7.3 grams of a red foam.

The above foam was suspended in phosphorous oxychloride (50 ml) and the mixture was heated to reflux for about 1 hour. The resulting homogeneous solution was concentrated under reduced pressure; water (100 ml) was added and the mixture was neutralized to pH 7–8 with 6N NaOH. To this was added saturated aqueous bicarb. (50 ml) and the mixture was extracted with ethyl acetate (3×100 ml). The combined organics were washed with water and brine, dried over sodium sulfate, filtered and concentrated under reduced pressure to give 6.81 grams of a tan solid.

The above solid was dissolved in a 1:1 mixture of ethanol (45 ml) and 1N NaOH (45 ml). After stirring at reflux for about 1 hour the solution was concentrated under reduced pressure, dissolved in water (200 ml) and extracted with ether (50 ml). The aqueous layer was acidified to pH 1 with 6N HCl and filtered. Recrystallization of the precipitate from methanol/isopropanol gave 4.4 grams of the title compound as a tan solid. MP 204°–206° C.; $^1$HNMR (250 MHz, DMSO-$d_6$) 1.44–1.53 (m,2H), 1.60–1.72 (m, 2H), 1.75–1.88 (m,2H), 2.62 (t, J=7.6 Hz, 2H), 3.87(s, 3H), 4.10(t, J=6.6 Hz, 2H), 7.15–7.31(m, 6H), 7.74(d, J=8.5 Hz, 1H), 7.87–7.97(M, 3H), 8.21 (s, 1H). Anal. calc'd for $C_{26}H_{26}N_2O_4$.HCl: C, 66.88; H, 5.83; N, 6.00. Found: C, 67.20; H, 5.75; N, 6.10.

EXAMPLE 214

4-[3-[4-(3,4-Dimethylphenyl)-4-hydroxy]butyloxy-4-methoxyl]phenyl-3-methylbenzoic acid A solution of 70 mg (0.156 mmol) of the compound of Preparation 51 in 2 ml of methanol was treated with 19 mg (0.33 mmol) of KOH, and the mixture was stirred for about 3 h at room temperature. An additional 19 mg of KOH was added, and stirring was continued for about 16 h. The mixture was heated to about 50° C. for about 0.5 h, and the solvent was removed by evaporation. The residue was diluted with water, acidified with 1N HCl, and extracted with EtOAc. The combined extracts were dried ($Na_2SO_4$) and concentrated to five 51 mg of a foam. Purification by flash chromatography using an EtOAc-hexane (1:1) eluant gave 42 mg (62%) of the title compound as a foam ($R_f$0.2 EtOAc-hexane, 1:1). $^1$H-NMR: δ1.82–1.97 (4H, m), 1.99 (3H, s), 2.00 (3H, s), 2.29 (3H, s), 3.96 (3H, s), 3.96–4.07 (2H, m) 4.6204.68 (1H, m) 6.74–7.27 (m, 7H), 7.86 (1H, d, J=8), 7.92 (1H, s) FAB MS (m/3): 434(M+), 417,258.

EXAMPLE 215

4-[3-[(4-Aminophenyl)butyloxy]-4-methoxy]phenyl-3-methylbenzoic acid

A solution of 190 mg (0.452 mmol) of the compound of Preparation 53 in a mixture of 7 ml of MeOH and 3 ml of water was treated with 20.0 mg (0.452 mmol) of NaOH, and the mixture was stirred for about 16 h at room temperature. An additional 20 mg of NaOH was added, and stirring was continued for about 24 h. The mixture was partially evaporated to remove MeOH, and the residue was carefully neutralized with 6M HCl. The oily precipitate was extracted with EtOAc (3×50 ml), and the combined extracts were combined, dried ($Na_2SO_4$), and evaporated to an oil. Crystallization from hexane afforded 60 mg (325) of the title compound, mp 150°–152° C. $^1$H-NMR ($CDCl_3$): δ1.76–1.99 (4H, m), 2.33 (3H, s), 3.22 (2H, t, J=7), 3.89 (3H, s), 4.06 (2H, t, J=5), 6.62–7.32 (9H, m), 8.90 (1H, d, J=8), 7.99 (1H, s). Anal. Calcd. for $C_{25}H_{27}O_4N.\frac{1}{2}H_2O$: C, 72.44; H, 6.81; N, 3.38; Found C, 72.77; H, 6.56 N, 3.39.

PREPARATION 1

3-(Bicyclo[2.2.1]hept-2-yloxy)-4-methoxybenzaldehyde

Diisopropyldiazodicarboxylate (7.8 ml, 39.5 mmol, 1.2 eq) was added neat to a 25° solution of (5.00 g, 32.9 mmol, 1.0 eq) 3-hydroxy-4-methoxybenzaldehyde (9.48 g, 36.1 mmol, 1.1 eq) triphenylphosphine, and (3.69 g, 32.9 mmol, 1.0 eq) (±)-endo-norborneol in 100 ml of anhydrous tetrahydrofuran. After refluxing for 6 hours, the reaction mixture was poured into 1 liter of $H_2O$ and extracted twice with ethyl acetate. The ethyl acetate layers were combined and washed twice with $H_2O$, once with 1N NaOH, once with $H_2O$ and once with brine and then the solution was dried over anhydrous sodium sulfate. Filtration, concentration, and drying afforded 26.1 g of crude product, which was chromatographed on a silica gel column, eluting with 20% ethyl acetate-hexane to afford 5.68 g, 70% yield, of a yellow oil. IR(cm$^{-1}$): 1680, 1580. NMR ($CDCl_3$): δ9.82 (s, 1H), δ4.27 (d, 1H). High resolution mass spectra (HRMS): 246.1300.

PREPARATIONS 2–8

Reaction of the appropriate vanillin with the requisite alcohol of the formula $R^2$—OH, analogous to the procedure of Preparation 1, afforded the following compounds:

![structure: 1,2-disubstituted benzene with R¹O, R²O and R groups]

| Prep. # | R¹ | R | R² | M.P. °C. | M.W. | Mass Spec (M+) | Calculated (%) C | Calculated (%) H | Found (%) C | Found (%) H |
|---|---|---|---|---|---|---|---|---|---|---|
| 2 | CH₃ | 3-CHO | cyclopentyl | oil | 220.3 | 220 | — | — | — | — |
| 3 | CH₃ | 3-OCH₃ (3-C(=O)OCH₃) | bicyclo[2.2.1]heptyl (sm = endo, prod = exo) | oil | 260.3 | 260 | 73.82 | 7.74 | 73.19 | 8.03 |
| 4 | CH₃ | 3-NO₂ | cyclopentyl | 63.5° | 237.3 | — | 60.75 | 6.37 | 60.58 | 6.05 |
| 5 | CH₃ | 4-CHO | PhCH₂CH(CH₃)– | oil | 284.4 | 284 | — | — | — | — |
| 6 | CH₃ | 4-CHO | (N-H pyrrolidin-3-yl)methyl (±) | oil | 235.3 | 235 | — | — | — | — |
| 7 | C₂H₅ | 3-CHO | cyclopentyl | oil | 234.3 | 234 | 71.76 | 7.74 | 71.74 | 8.00 |
| 8 | C₂H₅ | 3-CHO | bicyclo[2.2.1]heptyl (sm = endo, prod = exo) | oil | 260.2 | 260 | — | — | — | — |

PREPARATION 9

Bis(2-methoxy-5-bromophenyl)carbonate

Dissolved (8.26 ml, 160 mmol, 2.2 eq) bromine in 10 ml of CHCl₃ and then added it dropwise over 10 minutes to (20.0 g, 72.9 mmol, 1.0 eq) of bis(2-methoxy-phenyl) carbonate in 60 ml of CHCl₃ at room temperature. Stirred for 60 minutes at room temperature, then filtered the reaction mixture, washing the precipitate three times with CHCl₃, and once with hexane. The precipitate was recrystallized from CHCl₃ to yield 20.7 g, 66% yield, of bis(2-methoxy-5-bromophenyl)carbonate as white prisms.

PREPARATION 10

5-Bromoguaiacol

A suspension of (20.7 g, 47.9 mmol, 1.0 eq) bis(2-methoxy-5-bromophenyl)carbonate in 250 ml methanol and 60 ml (120 mmol, 2.5 eq) of 2N NaOH was refluxed for 2 hours. The reaction mixture was cooled to room temperature, concentrated to a volume of ca 100 ml, and poured 1 L of H₂O. The pH was adjusted to 2 using 1N HCl. The acidic mixture was transferred to a separatory funnel, and extracted three times with ether. The ether extracts were combined and washed once with H₂O, once with brine, and then dried over anhydrous sodium sulfate. Filtration, concentration and drying afforded 19.0 g of a white solid, which was recrystallized from petroleum ether to yield 17.63 g, 91% yield, of white prisms.

PREPARATION 11

2-(5-Bromo-2-methoxyphenoxy)bicyclo[2.2.1]heptane

Neat diethylazodicarboxylate (1.4 ml, 8.87 mmol, 1.2 eq) was added to a 25° C. solution of (1.50 g, 7.39 mmol, 1.0 eq)

5bromoguaiacol, (2.13 g, 8.13 mmol, 1.1 eq) triphenylphosphine and (0.829 g, 7.39 mmol, 1.0 eq) of S(-)endonorbomeol in 25 ml of anhydrous tetrahydrofuran. After stirring 18 hours at room temperature under $N_2$, the reaction mixture was diluted with 350 ml of ether, washed twice with 1N NaOH, once with $H_2O$, once with brine, and then dried over anhydrous $Na_2SO_4$. Filtration, concentration and drying afforded a yellow oil which was triturated with ca 250 ml of 1:1 ether-hexane to remove triphenylphosphine oxide. The filtrate was concentrated in vacuo, and chromatographed on a silica gel column, eluting with 10% ethyl acetate-hexane; to afford 1.75 g, 80% yield, of a clear, colorless oil. Elemental Analysis: Calc'd for $C_{14}H_{17}O_2Br$: Calc'd: C, 56.57; H, 5.77%. Found: C, 56.68; H, 5.73%.

PREPARATIONS 12–18

Reactions of 5-bromoguaiacol with the requisite of the formula $R^2$—OH, analogous to the procedure of Preparation 11, afforded the following compounds:

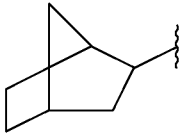

| Prep. # | $R^2$ | M.P. °C. | M.W. | Mass Spec (M+) | Calculated (%) C | H | Found (%) C | H |
|---|---|---|---|---|---|---|---|---|
| 12 | 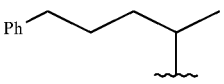 endo = sm exo = prod | oil | 297.3 | 298 | — | — | — | — |
| 13 | Ph~~~~~ (structure) | oil | 349.3 | 350 | — | — | — | — |
| 14 | 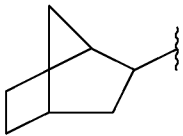 R(+) = sm S(+) = prod | oil | 297.2 | 298 | 56.67 | 5.77 | 56.74 | 5.72 |
| 15 | Ph~~~~~ (structure) R(−) = sm S(+) = prod | oil | 349.29 | 349.2 | 61.89 | 6.09 | 61.18 | 6.10 |
| 16 | Ph~~~~~ (structure) S(+) = sm R(+) = prod | oil | 349.29 | 349.2 | 61.89 | 6.09 | 59.77 | 5.66 |
| 17 | 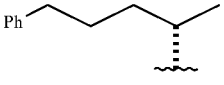 | oil | 271.17 | 271.1 | 53.16 | 5.58 | 53.41 | 5.52 |
| 18 | Ph~~~~~ (structure) | oil | 335.26 | — | — | — | — | — | sm = staring material
prod = product

PREPARATION 19

4-(Difluoromethoxy)-3-hydroxybenzaldehyde

Dissolved (5.00 g, 36.2 mmol, 1.0 eq) of 3,4-dihydroxybenzaldehyde in 60 ml of 1,4-dioxane, then added 24 ml of $H_2O$ and 36.2 ml (72.4 mmol, 2.0 eq) of 2N NaOH to the above solution at room temperature. After heating to 70° C. external, chlorodi-fluoromethane was bubbled into the reaction mixture for 50 minutes, maintaining a temperature of 60°–70° C. The reaction mixture was cooled to room temperature, concentrated in vacuo, diluted with 1 L H$_2$O and the pH adjusted to 5 using 1N HCl. The aqueous layer was then transferred to a separatory funnel, extracted four times with 300 ml each of ethyl acetate. The ethyl acetate layers were combined and washed once with brine and dried over anhydrous Na$_2$SO$_4$. The crude product was chromatographed over silica gel eluting with 25% ethyl acetate-hexane. Yield was 1.30 g, 19%, as a white solid. Elemental Analysis: Calc'd for C$_8$H$_6$O$_3$F$_2$: Calc'd: C, 51.08; H, 3.22. Found: C, 51.10; H, 3.14. NMR (300 MHz, CDCl$_3$): δ6.65 (1H, t), δ9.91 (1H, s). M.P.: 82°–83° C.

PREPARATION 20

3-(Difluoromethoxy)-4-hydroxybenzaldehyde

The title compound is prepared according to the reaction procedure of Preparation 19. The title product was isolated from the reaction mixture by column chromatography. M.P.: 64°–66° C. NMR (300 MHz, CDCl$_3$): δ6.61 (1H, t), δ9.83 (1H, s).

PREPARATION 21

3-Bicyclo[2.2.1]hept-2-yloxy-4-difluoromethoxybenzaldehyde

Into a stirred solution of (3.28 g, 14.1 mmol, 1.0 eq) of (±)-3-exo-norbornyloxy-4-hydroxybenzaldehyde in 200 ml of 2N NaOH and 100 ml of dioxane at 70° C. was bubbled in HCF$_2$Cl gas. The reaction mixture was poured into 400 ml of H$_2$O, acidified, and extracted with ether twice. The ether extracts were combined, washed twice with saturated NaHCO$_3$ solution, once with H$_2$O, once with brine, and dried over MgSO$_4$, then concentrated to yield 4 g of crude product. Flash chromatography on silica gel eluting with 15% ethyl acetate-hexane yielded 1.3 g, 33%, of an oil. Mass Spectra (M+): 282. NMR (300 MHz, CDCl$_3$): δ9.90 (s, 1H), δ6.64 (t, 1H).

PREPARATION 22

3-(Bicyclo[2.2.1]hept-2-yloxy)-4-hydroxybenzaldehyde

A mixture of (500 mg, 2.03 mmol, 1.0 eq) (±)-3-exo-norbornyloxy-4-methoxybenzaldehyde and (201 mg, 2.87 mmol, 1.4 eq) sodium thiomethoxide in 10 ml of anhydrous DMF was heated at 50°–60° C. for 20 hours. The reaction mixture was poured into 150 ml 0.5N HCl and extracted twice with ether. The ether extracts were combined, washed twice with saturated NaHCO$_3$, once with H$_2$O, once with brine, dried over MgSO$_4$, and then concentrated to give 0.5 g of an oil. Flash chromatography on silica gel, eluting with 15% ethyl acetate/hexane, yielded 320 mg, 72%, of an oil. Mass Spectra (M+): 232. NMR (300 MHz, CDCl$_3$): δ9.76 (s, 1H).

PREPARATION 23

2-Bicyclo[2.2.1]hept-2-yloxy)-4-[(methylthio)methyl]phenol

A solution of (9.00 g, 122 mol 5.0 eq) sodium thiomethoxide, (6.00 g, 24.4 mmol, 1.0 eq) (±)-3-exo-norbornyloxy-4-methoxybenzaldehyde in 120 ml of anhydrous dimethylformamide was heated to reflux under N$_2$ for 45 minutes. The reaction mixture was cooled, poured into 500 ml of 0.5 N HCl, extracted three times with ethyl acetate. The ethyl acetate extracts were combined, washed four times with H$_2$O, once with brine, dried over Na$_2$SO$_4$, and then concentrated to yield 6.85 g of a brown oil. Silica gel chromatography eluting with 10% ethyl acetate-hexane afforded 1.47 g, 26%, of a pale yellow oil. Elemental Analysis: Calcd. for C$_{15}$H$_{20}$O$_2$S: Calc'd: C, 68.14; H, 7.62; S, 12.13. Found: C, 68.10; H, 7.28; S. 12.38. M.P.=75°–77° C.

PREPARATION 24

3-(Bicyclo[2.2.1]hept-2-yloxy)-4-methoxy-α-methylbenzenemethanol

Added (108 mg, 2.85 mmol, 1.1 eq) sodium borohydride to a stirred solution of (675 mg, 2.59 mmol, 1.0 eq) (±)-3-methoxy-4-exo-norbornyloxy-acetophenone in 15 ml MeOH and 15 ml tetrahydrofuran. After 2 hours at room temperature, the reaction mixture was concentrated, poured into 200 ml of ethyl acetate, washed once with H$_2$O, once with brine, dried over Na$_2$SO$_4$, and then concentrated to yield 0.72 g of a clear oil. Silica gel chromatography eluting with 10% ethyl acetate/CH$_2$Cl$_2$ afforded 672 mg, 99%, of a clear oil. Mass spectra (M+): 262.

PREPARATIONS 25–28

Reaction of the following aldehydes, analogous to the procedure of Preparation 24 afforded the corresponding alcohols:

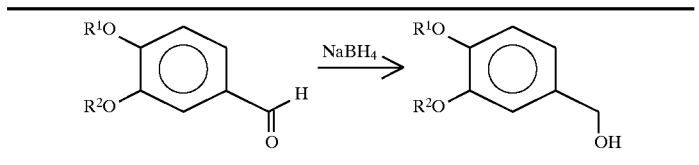

| Prep. # | R$^2$ | R$^1$ | M.W. | Mass Spec. (M+) |
|---|---|---|---|---|
| 25 | 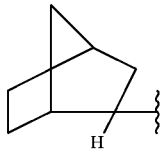 | HF$_2$C | 284.3 | 284 |

| Prep. # | R² | R¹ | M.W. | Mass Spec. (M+) |
|---|---|---|---|---|
| 26 | Ph-CH₂-CH₂-CH(CH₃)- | H₃C | 286.4 | 286 |
| 27 | H₃C | cyclopentyl-CH₂- | 222.2 | — |
| 28 | Ph-CH₂-CH₂-CH₂-CH(CH₃)- | H₃C | 300.4 | 00 |

PREPARATION 29

3-Cyclopentyl-4-methoxybenzoic acid

To a stirred suspension of (5.0 g, 27 mmol, 1.0 eq) methyl vanillate, (2.5 ml, 27 mmol, 1.0 eq) cyclopentanol, and (7.4 g, 28 mmol, 1.05 eq) triphenylphosphine in 40 ml of anhydrous tetrahydrofuran was added (4.7 ml, 29.7 mmol, 1.1 eq) of diethylazodi-carboxylate. The reaction mixture was stirred 18 hours at room temperature, concentrated in vacuo, and flash chromatographed on a silica gel column, eluting with 20% ethyl acetate/hexane, to yield 7.0 g, >100%, of an oil, methyl-3-methoxy-4-cyclopentyloxybenzoate.

A mixture of (7.0 g, 27 mmol, 1.0 eq) methyl-3-methoxy-4-cyclopentyloxy benzoate, 8 ml (42 mmol, 1.5 eq) 5N NaOH and 40 ml MeOH was refluxed for 3 hours. The mixture was concentrated to ca 20 ml, poured into 400 ml H₂O (pH 10) and washed twice with ether. The aqueous layer was acidified to pH 1 and extracted twice with ether. The ether extracts were combined, washed once with H₂O once with brine, dried over MgSO₄ and then concentrated to yield 6 g of a white solid. Recrystallization from ether-hexane yielded 5.60 g, 88%, of white crystals. Elemental Analysis: Calcd. for $C_{13}H_{16}O_4$: Calc'd: C, 66.09; H, 6.83. Found: C, 66.20; H, 6.64.

PREPARATION 30

3-Cyclopentyloxy-4-methoxybenzylbromide

To a stirred solution of (4.4 g, 20 mmol, 1.0 eq) 3-cyclopentyloxy-4-methoxybenzyl alcohol in 100 ml anhydrous tetrahydrofuran at 0° C. was added portionwise (9.2 g, 22 mmol, 1.1 eq) dibromotriphenylphosphorane over 10 minutes. The reaction was stirred at 0° C. for 1 hour, then allowed to warm to room temperature over 2 hours. The mixture was poured into 400 ml H₂O and extracted twice with 400 ml ether. The ether extracts were combined, washed once with saturated NaHCO₃, once with H₂O, once with brine, dried over MgSO₄, and then concentrated to give 10 g of a solid. Trituration with 10% ether-hexane followed by concentration of the filtrate gave ca 2 g of an oil. Flash chromatography on silica gel eluting with 15% ethyl acetate-hexane yielded 2.17 g, 38%, of an oil.

PREPARATION 31

Phosphonium, [3-(bicyclo[2.2.1]hept-2-yloxy)-4-methoxy]methyl]triphenyl-, bromide A mixture of (2.1 g, 7.36 mmol, 1.0 eq) 3-cyclopentyloxy-4-methoxybenzyl-bromide and (1.93 g, 7.36 mmol, 1.0 eq) triphenylphosphine in 50 ml of anhydrous toluene was heated to reflux for 18 hours. The resulting suspension was diluted with 50 ml hexane, cooled to 0° C., and filtered. The filament was washed with hexane and dried to yield 3.02 g, 73%, of a solid. M.P.=228°–230° C.

PREPARATION 32

1-(5-Bromo-2-methoxyphenoxy)-1-(3-phenyopropyl)cyclopropane (a) Preparation of 2-(5-bromo-2-methoxyphenoxy)-5phenyl-1-pentene Tebbe reagent (prepared from titanocene dichloride and trimethyl aluminum) (30 ml of a 0.55M solution in toluene) was added dropwise to a solution of (5-bromo-2-methoxyphenyl)-1-phenylbutyrate, pyridine(0.25 ml), anhydroustetrahydrofuran(10 ml), and anhydrous toluene (30 ml) at about 0° C. The reaction mixture was warmed to room temperature for about 2 hours, re-cooled to about 0° C. and quenched with 3N sodium hydroxide (6 ml). After gas evolution had ceased, ether was added and the mixture was dried over sodium sulfate, filtered and concentrated in vacuo. Chromatography through a short column of basic alumina eluted with 25% petroleum ether/ether afforded 4.4 g of a yellow oil. Mass spectra calculated for $C_{18}H_{19}BrO_2$: 347.2. Found: 347.

(b) Preparation of the title compound

The above oil (4.4 g) was dissolved in anhydrous ether (8 ml) and treated with methylene iodide (1.2 ml) followed by zinc-copper couple (0.9 g) and iodine (5 mg). After heating at reflux for about 17 hours the mixture was filtered and the solid washed with ether. The combined organics were washed with saturated aqueous ammonium chloride, saturated aqueous bicarbonate, brine, dried over sodium sulfate, filtered and concentrated in vacuo. Chromatography on silica gel column eluting with ethyl acetate-hexane (0–10%) afforded 3.2 g of a colorless oil. Mass spectra calculated for $C_{19}H_{21}BrO_2$: 361.3. Found: 362.

PREPARATION 33

3'-Bicyclo[2.2.1]hept-2-yloxy-4'-methoxy)-1, 1'-biphenyl-4-aminon

A mixture of (1.7 g, 5.01 mmol, 1.0 eq) of 2-[(4-methoxy-4'-nitro-[1, 1-biphenyl]-3-yl) oxy]bicyclo[2.2.1]heptane and 1.5 g of 10% Pd/C in 100 ml ethyl acetate was shaken on a Parr hydrogenation apparatus under 40 psi $H_2$ at room temperature for 10 minutes. The reaction mixture was filtered through celite, concentrated in vacuo, and the residue chromatographed on silica gel eluting with $CH_3OH$—$CH_2Cl_2$ (1%→2½%) to afford 1.45 g, 95%, of a white waxy solid. M.P.: 46°–50° C.

PREPARATION 34

3-[3-Bicyclo[2.2.1]hept-2-lyoxy)-4 (diffuoromethoxy) phenyl]pentanediamide

A mixture of (3.40 g, 12.0 mmol, 1.0 eq) 3-(bicyclo[2.2] hept-2-yloxy)-4-difluoromethoxybenzaldehyde, (334 µl, 3.37 mmol, 0.28 eq) piperidine and (3.06 g, 36.0 mmol, 3.0 eq) cyanoacetic acid in 50 ml of anhydrous pyridine was heated to reflux for 17 hours. The reaction mixture was cooled to room temperature, diluted with $H_2O$ and extracted three times with ethyl acetate. The ethyl acetate extracts were combined, washed twice with 1N HCl, once with saturated $NaHCO_3$, once with $H_2O$, once with brine, dried over $Na_2SO_4$ and concentrated in vacuo. The residue was chromatographed on a silica gel column eluting with 1:3 ethyl acetate:hexane to yield 2.13 g, 51%, of a yellow oil. Elemental Analysis: Caic'd for $C_{19}H_{20}N_2O_2F_2$: Calc'd: C, 65.87; H, 5.82; N, 8.09. Found: C, 65.53; H, 5.63; N, 8.25.

$H_2O_2$ (250 ml of 30%, 29.2 mmol, 5.0 eq) was added dropwise to a 0° C. mixture of (2.02 g, 5.83 mmol, 1.0 eq) 2-[3-(bicyclo[2.2.1]hept-2-yloxy)-4-difluoromethoxyphenyl]propane-1,3-dinitrile and 1.67 ml of 10% aqueous $Na_2CO_3$ in 30 ml of acetone and 15 ml of $H_2O$. After stirring 1hour at 0° C., the reaction mixture was allowed to warm to room temperature and was left stirring for 72 hours. The reaction mixture was poured into 550 ml of ethyl acetate and 400 ml of $H_2O$ and stirred for 1 hour. The 2 layers were separated, and the aqueous layer was extracted four times with ethyl acetate. The ethyl acetate extracts were combined, washed once with $H_2O$, once with brine, dried over $Na_2SO_4$ and concentrated to yield 2.0 g of a white solid. Silica gel chromatography eluting with 10% $CH_3OH$–$CH_2Cl_2$ afforded 1.29 g, 58%, of a white powder. M.P.: 168°–169° C. Elemental Analysis: Calc'd for $C_{19}H_{24}N_2O_4F_2$: Calc'd: C, 59.67; H, 6.33; N, 7.33. Found: C, 59.60; H, 5.99; N, 7.11.

PREPARATION 35

Methyl 2-butyl-1-(4-hydroxyphenyl)-1H-benzimidazole-5-carboxylate

A mixture of (1.5 g, 6.98 mmol, 1.0 eq) methyl-3nitro-4-chlorobenzoate and (760 mg, 6.98 mmol, 1.0 eq) 4-aminophenol in 30 ml dry dimethylsulfoxdde was heated to reflux for 18 hours. The mixture was poured into 300 ml of $H_2O$, acidified to pH 5 and extracted once with ether. The resulting sludge was filtered through celite, and the filtrate layers separated. The aqueous layer was extracted with ether, and the ether extracts were combined, washed twice with $H_2O$, once with brine, dried over $MgSO_4$, and concentrated to give 3.0 g of an oil. Silica gel chromatography eluting with 30% ethyl acetate-hexane gave 850 mg, 42%, of a dark red gum.

A mixture of (850 mg, 2.95 mmol, 1.0 eq) of methyl 4-[(4-hydroxyphenyl) amino]-3-nitrobenzoate and 850 mg of 10% Pd/C in 40 ml ethyl acetate was placed on a Parr hydrogenation apparatus and shaken for 3 hours under 40 psi $H_2$. The mixture was filtered through celite, concentrated, and chromatographed on a silica gel column eluting with 40% ethyl acetate/hexane to yield 470 mg, 56%, of an off-white solid.

A mixture of (436 mg, 1.69 mmol, 1.0 eq) methyl 4-[4-hydroxyphenyl)amino]-2-aminobenzoate and 3 ml of valeric anhydride was heated to reflux for 3 hours. The reaction mixture was cooled to room temperature and flash chromatographed on a silica gel column eluting with 10% ethyl acetate/$CH_2Cl_2$ to give an oil, which was taken up in 15 ml MeOH and treated with 5 ml 1N NaOH for 1 hour. The mixture was poured into 300 ml of $H_2O$, acidified to pH 5 and extracted twice with ethyl acetate. The ethyl acetate extracts were combined, washed once with $H_2O$, once with brine, dried over $MgSO_4$ and concentrated to give 0.6 g of an oil. Flash chromatography on silica gel eluting with 2½% $CH_3OH/CH_2Cl_2$ gave 345 mg, 63%, of white foam. Mass Spectra: 324.2.

PREPARATION 36

4-3H-lmidazo[4,5b]-2-butylpyridinephenol

A mixture of (1.0 g, 4.33 mmol, 1.0 eq) 4-[(2-nitro-4pyridinyl)amino]phenol and 500 mg of 10% Pd/C in 100 ml of tetrahydrofuran and 100 ml of methanol was placed on a Parr hydrogenation apparatus and shaken under 50 psi $H_2$ for 1 hour. The reaction mixture was filtered through celite and the filtrate concentrated in vacuo to give 1.01 g, >100%, of a tan solid.

A miture of 900 mg (4.47 mmol, 1.0 eq) of the above diamine in 10 ml of valeric anhydride was heated to reflux for 3 hours. The reaction mixture was poured into 150 ml of 0.5N HCl, stirred 5 minutes, washed once with ether and the ether wash extracted with 0.5N HCl. The acidic extracts were combined, basified to pH 10 and extracted with ethyl acetate. The ethyl acetate extracts were combined, washed once with 0.5N NaOH, once with $H_2O$, once with brine, dried over $MgSO_4$ and concentrated to give 1 g of an oil. Silica gel chromatography eluting with 5% $CH_3OH/CH_2Cl_2$ gave 900 mg, 57%, of an oil.

A mixture of (908 mg, 2.47 mmol, 1.0 eq) butyl 4-(2-butyl-1H-lmidazo[4,5-c]pyridin-1-yl)benzoate and 6 ml (6 mmol, 5.0 eq) of 1N NaOH in 25 ml methanol was stirred at room temperature for 2 hours. The reaction mixture was concentrated to ca. 10 ml, poured into 200 ml of $H_2O$, and extracted twice with ether. The aqueous layer was neutralized and extracted twice with ethyl acetate. The ethyl acetate extracts were combined, washed once with $H_2O$, once with brine, dried over $MgSO_4$ and concentrated to give 1 g of solid. Silica gel chromatography eluting with 10% $CH_3OH/CH_2Cl_2$ yielded 590 mg, 89%, of white solid. M.P.: 161°–163° C.

PREPARATION 37

4-(2-Methyl-3H-imidazo[4,5-b]pyridin-3-yl)phenol

A mixture of (3.5 g, 22 mmol, 1.0 eq) 2-chloro-3-nitro-pyridine, (3.65 g. 22 mmol, 1.0 eq) Kl, (1.85 g, 22 mmol, 1.0 eq) NaHCO$_3$, and (2.40 g, 22 mmol, 1.0 eq) 4-amino-phenol in 25 ml of dry dimethylformamide was heated to reflux for 18 hours. The mixture was poured into 400 ml of H$_2$O, neutralized to pH 7 and extracted twice with ethyl acetate. The ethyl acetate extracts were combined, washed twice with 5% Na$_2$S$_2$O$_3$, once with H$_2$O, once with brine, dried over MgSO$_4$ and concentrated to give 4.8 g of a black solid. Flash chromatography on silica gel eludng with 50% ethyl acetate/CH$_2$Cl$_2$, followed by crystallization from isopropyl ether/CH$_2$Cl$_2$ gave 3.7 g, 73%, of an orange-red solid.

A mixture of (3.6 g, 15.6 mmol, 1.0 eq) the nitropyridine and 0.9 g of 10% Pd/C in 50 ml of tetrahydrofuran and 50 ml of methanol was placed on a Parr hydrogenation apparatus and shaken under 50 psi H$_2$ for 1 hour. The mixture was filtered through celite, concentrated in vacuo (4 g purple solid), and flash chromatographed on a silica gel column eluting with 10% CH$_3$OH/CH$_2$Cl$_6$ to give 3.5 g of solid. Trituration from ethyl acetate gave 3.0 g, 96%, of a pink solid.

A mixture of (1.0 g, 4.97 mmol, 1.0 eq) 4-[(3-amino-2-pyridinyl)amino]phenol in 25 ml of valeric anhydride was heated to reflux for 8 hours. The reaction mixture was cooled, poured into 150 ml of 0.5N HCl, stirred 10 minutes, and extracted twice with ether. The ether extracts were combined, washed three times with saturated NaHCO$_3$, once with H$_2$O, once with brine, dried over MgSO$_4$, and concentrated to give an oil. The oil was taken up in 100 ml CH$_3$OH and treated with 60 ml of 2N NaOH and allowed to stir at room temperature for 1 hour. The mixture was concentrated, poured into 200 ml of H$_2$O and washed twice with ether. The aqueous layer was neutralized, and extracted twice with ethyl acetate. The ethyl acetate extracts were combined, washed once with H$_2$O, dried over MgSO$_4$, and concentrated to give 0.7 g of a solid. Silica gel chromatography eluting with 10% CH$_3$OH/CH$_2$Cl$_2$ gave 510 mg, 38%, of a solid. M.P.: 268°–2690° C.

PREPARATION 38

2-Butyl-3-(4-hydroxyphenyl)benzimidazole

A mixture of (8.0 g, 51 mmol, 1.0 eq) 1-chloro-2-nitrobenzene and (5.54 g, 51 mmol, 1.0 eq) 4-aminophenol in 40 ml of dry dimethylsulfoxide was heated to reflux for 18 hours. The reaction mixture was cooled, poured into 400 ml of 0.1 N HCl and 400 ml ethyl acetate, stirred, and filtered through celite. The filtrate layers were separated, and the aqueous layer was extracted with ethyl acetate. The ethyl acetate extracts were combined, washed twice with H$_2$O, once with brine, dried over MgSO4, and concentrated to give 8 g of a dark oil. Silica gel chromatography eluting with 20% ethyl acetate/hexane gave 1.63 g, 14%, of a red solid.

A mixture of (1.6 g, 6.89 mmol, 1.0 eq) 4N-(2-nitrophenyl)amino phenol and 800 mg of 10% Pd/C in 100 ml ethyl acetate was placed on a Parr hydrogenation apparatus and shaken under 50 psi H$_2$ for 3 hours. The mixture was filtered through celite, concentrated in vacuo, and chromatographed on a silica gel column eluting with 50% ethyl acetate/hexane to give 1.3 9g 94%, of an orange-yellow solid.

A mixture of (600 mg, 3.00 mmol, 1.0 eq) 4-N-(2-aminophenyl)arnino phenol and 10 ml valeric anhydride was heated to reflux for 18 hours. The mixture was taken up in 50 ml of methanol, basified with 2N NaOH to pH 10, and stirred 1 hour at room temperature. The reaction mixture was then neutralized and extracted twice with ethyl acetate. The ethyl acetate extracts were combined, washed twice with H$_2$O, once with brine, dried over MgSO$_4$ and concentrated to give 1 g of an oil. Silica gel chromatography eluting with 2½% CH$_3$OH–CH$_2$Cl$_2$ gave 124 mg, 16%, solid. M.P.: 192°–194° C.

PREPARATION 39

4'-Methoxy-3'-(1-methylphenylbutoxy)-[1,1'-biphenyl]-4-carbonitrle

To a solution of (1.4 g, 4.01 mmol, 1.0 eq) of (±)-1-methoxy-2-exo-norbomyloxy-4-boromobenzene in 40 ml dry THF at –78° C. was added dropwise 1.76 ml (4.4 mmol, 1.1 eq) of 25M n-BuLi. After stirring 40 minutes at –7820 C., (4.81 ml, 4.81 mmol, 1.2 eq) 1.0M ZnCl$_2$ in ether was added, and the mixture warmed to room temperature over 30 minutes. Pd (PPh$_3$)$_4$ (231 mg, 0.2 mmol, 0.05 eq) and (918 mg, 4.01 mmol, 1.0 eq) 4-iodobenzonitrile were added, and the mixture stirred 2 hours at room temperature. The reaction mixture was concentrated in vacuo and chromatographed on silica gel eluting with ether-hexane (5–30%) to afford 1.1 g, 74%, of 4'-methoxy-3'-(1-methyl+phenylbutoxy)-[1,1'-biphenyl]-4-carbonitrile. NMR (250 MHz, CDCl$_3$): 7.70 (2H, m); 7.59 (2H, m); 7.17 (7H, m); 6.96 (1H, m); 4.42(1H, m); 3.90 (3SH, s); 1.35 (3H, d, j=6.1 Hz).

PREPARATION 40

Methyl 1-(3-hydroxymmethoxyphenyl)-1H-benzimidazole-5-carboxylate

A mixture of (10 g, 74.5 moles) 5-amino-2-methoxyphenol and (13.3 g, 62 mmoles) methyl 3-nitro-4-chlorobenzoate in 50 ml of pyridine was stirred at room temperature overnight. The volatiles were removed in vacuo and the residue was dissolved in ethyl acetate and washed with dilute HCl, then dried over MgSO$_4$ and evaporated to give 12.7 g of crude product which was triturated with CH$_2$Cl$_2$ and filtered to give 3.9 g of purified methyl 4-N(4-methoxy-3-hydroxyphenyl)amino-3-nitrobenzoate.

A solution of 3.9 g of the above nitro compound in 75 ml of methanol and 50 ml of THF and 400 mg of 10% palladium on charcoal was shaken on a Parr shaker, at 40 psi H$_2$ for 5 hours. The catalyst was removed -by fiitration and the solvent evaporated in vacuo. The product methyl 4-N (4-methoxy-3-hydroxyphenyl) amino-3-aminobenzoate (3.4 g) was used without purification.

A mixture of 3.4 g of the above amine and 900 mg of ethyl formate in 25 ml of formic acid was heated at 100° overnight. The solvents were evaporated in vacuo to give 1.6 g of the title product.

PREPARATION 41

2-N[3-(Cyclopentyloxy)-4-methoxyphenyl-carbonyl] amino-3-hydroxypyridine

A mixture of (1.2 g, 5 mmoles) of 4-methoxy-3-cyclopentyloxybenzolc acid and 25 ml of thionyl chloride was heated at reflux for 30 minutes. Excess thionyl chloride was removed in vacuo and the resulting acid chloride was used without purification.

The crude acid chloride from above was dissolved in THF and was added to a solution of 600 mg of 2-amino-3-hydroxypyridine in 5 ml of pyridine at 0° C. After stirring at 0° C. for 2 hours, the reaction was allowed to stir at room temperature overnight. The volatiles were evaporated and the residue was triturated with H$_2$O and filtered to give 1.4 g of the desired amide. M.P. 165°–166° C.

PREPARATION 42

3-Cyclopentyloxy-4-methoxybenzthioamide

4-Methoxy-3-cyclopentyloxybenzoic acid was converted to its acid chloride analogous to the procedure of Preparation 41.

The acid chloride (500 mg) was dissolved in 10 ml of THF and added dropwise to a solution of aqueous ammonium hydroxide at 0° C. After 30 minutes the reaction was extracted with ethyl acetate. The ethyl acetate layer was dried and evaporated to give 420 mg of product. M.P.: 167°–1680° C.

A mixture of 400 mg of the amide and 413 mg of Lawesson's reagent in 20 ml of toluene was heated at reflux for 1 hour. The volatiles were evaporated and the residue purified on silica gel with $CH_2Cl_2$/methanol to give 220 mg of product. M.P.: 145°–1470° C.

PREPARATION 43

4-[3-(Bicyclo[2.2.1]hept-2-yloxy)-4-methoxyphenyl]-2-methylthiazole

4-Methoxy-3-norbornyloxybenzoic acid was converted to the corresponding acid chloride using the procedure of Preparation 41.

To a solution of 6.9 gm of the acid chloride in 50 ml of ether was added dropwise to a solution of 2 equivalents of diazomethane in ether. The resulting diazoketone was then converted to chloromethyl ketone by addition of excess HCl(g). Evaporation of the volatiles gave 3.5 g of chloromethyl ketone which was used without purification.

A solution of 294 mg of chloromethyl ketone and 120 mg of thioacetamide in 5 mls of DMF was heated on a steam bath for 8 hours. The reaction was then poured onto $H_2O$ and extracted with ethyl acetate. The ethyl acetate layer was dried and evaporated to give 260 mg crude product. Purification on silica gel with $CH_2Cl_2$/ethyl acetate gave 90 mg of the title product, M.P. 81°–82° C.

PREPARATION 44

1-(3-Hydroxyvmethoxyphenyl)-1H-imidazo[4,5c]pyridine

A miture of 5.7 g of 3-nitro-4-chloropyridine, 3 g of $NaHCO_3$ and 5 g of 5-amino-2-methoxyphenol in 100 ml of ethanol was sfirred at room temperature overnight. The ethanol was evaporated and the residue slurried with hot THF to dissolve the product. Evaporation of the THF gave 8.7 g of the nitro product used without purification.

The nitro compound from above (8.7 g) was reduced with $H_2$ and Pd/C on a Parr shaker during 5 hours. The reaction was filtered over celite and evaporated to give 8.2 g of the amine product.

A solution of 2.7 g of the amino pyridine from above in 75 ml of formic acid containing 1.7 g of ethyl formate was heated at 100° C. for 8 hours. The volatiles were evaporated and the residue was treated with methanolic NaOH at 100° C. for 2 hours. The reaction was cooled and the pH adjusted to 7.0 with 1N HCl. The resulting solid was fiftered and dried to give 2.05 g of product. M.P.: 231°–233° C.

PREPARATION 45

1-(5-Bromo-2-methoxyphenoxy)-5-(4-fiuorophenyl)pentane (a) Preparation of 5-(4-fluorophenyl)pentane A suspension of 6-bromo-1-hexene (10 g), magnesium (1.5g), and lodoethane (1 drop) in anhydrous tetrahydrofuran was heated at reflux until all of the magnesium dissolved. The resulting Grignard reagent was cooled to about 0° C. and was treated with a 1M solution of $ZnCl_2$ in ether (67 ml), and the mixture was allowed to warm to room temperature over 30 minutes. Tetraids(triphenylphosphine)palladium (0) (3.5 g) and 4-bromofluorobenzene (6.73 ml) were added to the reaction and the mixture was heated to reflux for 1 hour. The mixture was cooled to room temperature, concentrated in vacuo, diluted with hexane, filtered and concentrated once more in vacuo. Chromatography on a silica gel column eluting with ether-hexane (0–5%) afforded 5 g of a colorless oil.

(b) Preparation of 5-(4-fluorophenyl)pentanal

The above oil (2.6 g) was dissolved in 1:9 methanol-methylenechloride (50 ml), cooled to about −78° C. and treated with ozone gas until the mixture became light blue. At this time ozone addition was ceased and the mixture was purged with nitrogen gas. Triphenylphosphine (5 g) was added and the mixture was allowed to stand at room temperature over 24 hours. The reaction mixture was concentrated in vacuo, diluted with ether, filtered and concentrated once more in vacuo. Chromatography on a silica gel column eluting with ethyl acetate-hexane (10–20%) gave 1.3 g of aldehyde as a colorless oil.

(c) Preparation of 5-(4-fluorophenyl)pentanol

The above aldehyde (1.3 9) was dissolved in methanol (20 ml) at about 0° C. and treated with sodium borohydride (1.0 g). After 10 minutes the mixture was quenched with saturated aqueous ammonium chloride, and was extracted with ether. The combined organics were washed with water followed by brine, dried over sodium sulfate, filtered and concentrated in vacuo. Filtration through silica gel gave 1.2 g as a colorless oil.

(d) Preparation of the title compound 1-(5-Bromo-2-methoxyphenoxy)-5-(4-fluorophenyl)pentane was prepared from 5-bromoguaiacol and 5-(4-fluorophenyl)pentanol as in Preparation 11. M.P.: 46°–47° C.

PREPARATION 46

1-(5-Bromo-2-methoxyphenoxy)-4-(4-fluorophenoxy)butane (a) Preparation of 4-(4-fluorophenoxy)-1-butene A solution of 4-bromo-1-butene (4.0 g), 4-fluorophenol (3.0 g), potassium carbonate (3.8 g) and acetone (75 ml) was heated at reflux over 16 hours. The mixture was then concentrated in vacuo, dluted with ether, washed with water followed by 1N sodium hydroxide, dried over sodium sulfate, filtered, and concentrated in vacuo. Chromatography on a silica gel column eluting with 25% ethyl acetate-hexane afforded 1.6 g of a colorless oil.

(b) Preparation of 1-bromor-4-(4-fluorophenoxy)butane

Anhydrous HBr was bubbled through a mixture of the above oil (1.6 g) and benzoyl peroxide (0.136 g) in petroleum ether (60 ml) kept below 15° C. using an ice-bath. After 30 minutes the system was purged with nitrogen, diluted with petroleum ether (50 ml) and washed with saturated aqueous sodium bicarbonate and brine. The mixture was then dried over sodium sulfate, filtered and concentrated in vacuo. Chromatography on a silica gel column eluting with ethyl acetate-hexane (5–10%) afforded 2.08 g as a colorless oil.

(c) Preparation of the title compound

A mixture of the above oil (2.08g), 5-bromoguaiacol (1.71 g), potassium carbonate (3.5 g) and dimethylformamide (35 ml) was stirred at about 80° C. over 3 hours. The mixture was cooled to room temperature, poured into water (250 ml) and extracted with 20% ethyl acetate-hexane. The combined organics were washed with brine, dried over sodium sulfate and concentrated in vacuo. Chromatography on a silica gel column eluting with 25% ethyl acetate-hexane afforded 2.27 g of a white crystalline solid. M.P.: 44°–47° C.

PREPARATION 47

4-Methoxy-3-(5-phenylpentoxy)benzoio acid

A To a magnetically stirred solution of 4-methoxy-3-(5-phenylpentoxy)-benzaldehyde (9.90 grams, 332 mmols) and 2-methyl-2-butene (56.2 ml, 530 mmoles) in tert-butanol (300 ml) was added a solution of sodium chlorite (24.0 grams) and sodium phosphate monobasic (24.0 grams) in water (200 ml) over 10 minutes. After stirring vigorously for about 30 minutes the miture was concentrated under reduced pressure and acidified to pH2 with 6N HCl. The precipate was filtered and dried to give 9.4 grams of a white solid, MS m/z [M$_+$]314.

PREPARATION 48

4-[(5-Bromo-2-methoxy)phenoxy]butanoic acid ethyl ester

A mixture of 15.0 g (0.0740 mol) of 2-methoxy-4-bromophenol, 17.4 g (0.0890 mol) of ethyl 4-bromobutyrate, 20.5 g (0.148 mol) or $K_2CO_3$, and 200 ml of DMF was stirred at about 80° C. was continued for about 16 h. The combined ether extracts were washed with brine (1×300 ml), dried ($MgSO_4$), and evaporated to give 26.0 g of an orange oil. Purification by flash chromatography using an ethyl acetate-hexane (1:4) eluant gave 19.7 g (84%) of the title compound as a clear oil (R, 0.5 EtOAc-hexane, 3:7). $^1$H-NMR (CDCl$_3$) δ1.25 (3H, t, J=7), 2.09–2.18 (2H, m), 2.51 (2H, t, J=7), 3.82 (3H, s), 4.03 (2H, t, J=7), 4.13 (2H, q, J=7), 6.72 (1H, d, J=8), 6.97–7.08 (2H, m).

PREPARATION 49

4-[(5-Bromo-2-methoxy)phenoxy]butanal

A solution of 1.50 g (4.72 mmol) of the compound of Preparation 48 in 15 ml of dry THF was chilled to about −78° C. and was treated dropwise with 7.08 ml (7.08 mmol) of a solution of 1.0M diusobutylaluminum hydride in hexane at such a rate that the reaction temperature did not rise above −60° C. After stirring an additional 0.5 h, 5 ml of methanol was added dropwise. After the exotherm had subsided, 25 ml of 1N HCl was added and the mixture was allowed to warm room temperature. The THF and methanol was removed by evaporation, and the residue was diluted with 150 ml of 1N HCl and was extracted with EtOAc (2×100 ml). The combined extracts were washed with saturated NaHCO$_3$ solution (2×100 ml), brine (1×100 ml), dried (MgSO$_4$), and evaporated to give 1.25 g of a clear oil. Purification by flash chromatography using an EtOAc-hexane eluant (3:7) afforded 523 mg (41%) of the title compound as a clear oil (R$_1$ 0.5 EtOAc-hexane, 1:1). $^1$H-NMR δ2.10–2.20 (2H, m), 2.68 (2H, t, J=6), 3.80 (3H, s), 4.00 (2H, t, J=6), 6.71 (1H, d, J=9), 6.95–7.04 (2H, m), 9.82 (1H, s).

PREPARATION 50

4-(5-Bromo-2-methoxy)phenoxy-1-(3,4-dimethyl)phenyl-1-butanol

A solution of 176 mg (0.952 mmol) of 4-bromo-o-xylene in 5 ml of dry THF was chilled to about −78° C. and was treated dropwise with 0.322 ml (0.805 mmol) of a 2.5M solution of n-Buli in hexane. When the exotherm had subsided, the mixture was stirred an additional 10 min, and a solution of 200 mg (0.732 mmol) of the compound of Preparation 49 in 5 ml of THF was added. The mixture was stirred an additional 20 min and was quenched by the addition of saturated aqueous NH$_4$Cl solution. After warming to room temperature, the THF was removed by evaporation and the residue. was diluted to 100 ml with water and was extracted with EtOAc (2×100 ml). The extracts were combined, dried (Na$_2$SO$_4$), and evaporated to give 400 mg of a clear oil. Purification by flash chromatography using an EtOAc-hexane eluant (3:7) afforded 172 mg (62%) of the title compound as an oil (R$_1$ 0.4 EtOAc-hexane). $^1$H NMR (CDCl$_3$): δ1.81–1.87 (4H, m), 2.22 (3H, s), 2.23 (3H, s), 3.89 (3H, s), 3.96–4.01 (2H, m), 4.60–4.69 (1H, m), 6.66 (1H, d, J=g ), 6.87–7.08 (5H, m).

PREPARATION 51

4-Carbomethoxy-2-methylphenylboronlc acid

To a solution of 50.0 g (0.232 mol) of 4bromo-3-methylbenzoic acid in 500 ml of dry THF at about −78° C. was added dropwise 300 ml (0.511 mol) of a 2.5M solution of n-Buli in hexane over a period of about 0.5 h. After 20 min. of additional stirring at about −78° C., 64.0 g (0.278 mol) of tributylborane was added dropwise. The mixture was stirred an additional 3 h at about −78° C., and, following removal of the ice bath, 500 ml of 1N HCl solution was added carefully. The mixture was stirred for about 16 h at room temperature and the organic layer was separated. The aqueous layer was extracted with EtOAc (2×50 ml) and the combined organic extracts were dried (Na$_2$SO$_4$) and evaporated. The residue was triturated in hexane and 16 g of a white solid was removed by flitralion. The mother liquor was concentrated and was purified by flash chromatography using an EtOAc-hexane eluant (3:7 to 1:1) to give 4.00 g of crude 4-carboxy-2-methylphenylboronlc acid; (R$_1$ 0.1 EtOAc-hexane, 1:1). This material was dissolved in 60 ml of thionyi chloride and was refluxed for 1 h. The excess thionyl chloride was removed by distillation under reduced pressure, and the oily residue was diluted with 100 ml of methanol. The mixture was stirred for about 16 h at room temperature and the methanol was removed by evaporation. The residue was purified by flash chromatography using an EtOAc-hexane eluant (3:7 to 1:1) to afford 2.35 g (4%) of the title compound as a white solid (R$_1$ 0.35 EtOAc-hexane, 1:1). $^1$H-NMR (DMSO-d$^8$): δ6 2.68 (3H, s), 3.81 (3H, s), 7.66–7.72 (2H, m), 7.93 (1H, d, J=8).

PREPARATION 52

4-[3-[4-(3,4-Dimethylphenyl)-4-hydroxy]butyloxy-4-methoxy]phenyl-3-methylbenzoic acid methyl ester To a solution of 170 mg (0.448 mmol) of the compound of Preparation 49 in 4 ml of toluene was added 17 mg of tetrakistriphenylphosphinepalladium, a solution of 82 mg (0.448 mmol) of the compound of Preparation 51 in 2 ml of EtOH, and 0.670 ml of saturated aqueous solution of Na$_2$CO$_3$. The resulting mixture was heated to reflux for about 4 h. The mixture was partially evaporated to remove toluene and ethanol, and the residue was diluted with EtOAc and was washed with water. The organic layer was dried (Na$_2$SO$_4$) and evaporated to give 228 mg of a brown oil. Purification by flash chromatography with an ETOAc-hexane eluant (3:7) afforded 72 mg (36%) of the title compound as a foam ($R_1$ 0.45 EtOAC-hexane 1:1). $^1$H-NMR: δ1.82–1.97 (4H, m), 2.20 (3H, s), 2.21 (3H, s), 3.87 (3H, s), 3.90 (3H, s), 3.97–4.08 (2H, m), 4.63–4.72 (1H, m) 6.73–7.25 (6H, m), 7.82 (1H, d, J=8), 7.88 (1H, s).

PREPARATION 53

4-Bromo-4-methoxy-3-[(4-aminophenyl)butyloxy]benzene

A mixture of 298 mg (1.09 mmol) of the compound of Preparation 49, 11 mg (1.20 mmol) of aniline, and 5 ml of MeOH was stirred at room temperature for about 1 h. The mixture was chilled to about 0° C. and was treated with 46 mg (1.22 mmol) of NaBH$_4$. After stirring for about 2 h at about 0° C., excess 1N HCl was added and the mixture was partially evaporated to remove MeOH. The residue was overlayed with EtOAc, and the aqueous layer was basiied to pH 8. The organic layer was separated and was combined with two EtOAc extracts of the aqueous layer. The combined organic extracts were dried (Na$_2$SO$_4$) and evaporated to give an oil, which was purified by flash chromatography using an EtOAc-hexane eluant (1:4) to afford 135 mg (35%) of the title compound as an oil ($R^1$ 0.4 EtOAo-hexane, 3:7). $^1$H-NMR δ; 1.77–1.94 (4H, m), 3.19 (2H, t, J=6), 3.81 (3H, s), 4.00 (2H, t, J=6), 6.58–7.16 (8H, m).

PREPARATION 54

4-[3-[(4-Aminophenyl)butyloxy]-4-methoxy]phenyl-3-methylbenzoic acid methyl ester Following the same procedures in Preparation 52, 1.88 mg (0.536 mmol) of the pound of Preparation 53 and 109 mg (0.590)mmol) of the compound of Preparation 51 were coupled to give 193 mg (86%) of the title compound. Purification was performed by flash chromatography using an EtOAc-hexane (1:4) eluant. $^1$H-NMR δ1.82–2.02 (4H, m), 2.32 (3H, s), 3.21 (2H, t, J=7), 3.91 (s, 3H), 3.93 (s, 3H), 4.06 (2H, t, J=6), 6.60–7.30 (9H, m), 7.87 (1H, d, J=8), 7.93 (1H, s).

What is claimed is:
1. A compound of the formula

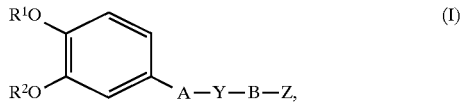

the racemic-diastereomeric mixtures and optical isomers of said compounds and the pharmaceutically acceptable salts thereof wherein $R^1$ is selected from the group consisting of methyl, ethyl, difluoromnethyl and triifuoromethyl;

$R^2$ is selected from the group consisting of (C$_1$–C$_6$)alkyl, alkoxyalkl having 3 to 7 carbons in the alkoxy portion and 2 to 4 carbons in the alkyl portion, phenoxyalkyl having 2 to 6 carbons in the alkyl portion, (C$_3$–C$_7$)cycloalkyl, (C$_6$–C$_9$)polycycloalkyl, phenylalkyl having 1 to 8 carbons in the alkyl portion, phenylaminoalkyl having 2 to 6 carbons in the alkyl portion and the amino may be optionally substituted with (C$_1$–C$_4$) alkyl and indanyl, where the alkyl portion of said alkyl, phenoxyalkyl, cycloalkyl, polycycloalkyl, phenylalkyl and indanyl may optionaliy be substituted with one or more fluorine atoms, —OH or (C$_1$–C$_4$) alkoxy, and the aryl portion of said phenylalkyl, phenoxyalkyl and indanyl may optionally be substituted with (C$_1$–C$_4$)alkyl, (C$_1$–C$_4$)alkoxy or halogen;

A and B are independently selected from the group consisting of a covalent bond, optionally substituted (C$_1$–C$_5$)alkylene, optionally substituted (C$_2$–C$_5$) alkenyl and optionally substituted phenylene, where said optionally substituted alkylene may be monosubstituted and each substituent is selected from the group consisting of oxo, (C$_1$–C$_4$)alkoxy, CO$_2$R$^6$ and hydroxy, said optionally substituted alkenyl may be monosubstituted with (C$_1$–C$_4$)alkoxy or CO$_2$R$^5$, and said optionally substituted phenylene may be monosubstituted with (C$_1$–C$_4$)alkoxy, CO$_2$R$^6$ or hydroxy, wherein R$^6$ is hydrogen or (C$_1$–C$_4$)alkyl;

Y is selected from the group consisting of a covalent bond, O, NR$^6$ and S wherein R$^6$ is as defined above;

Z is selected from the group consisting of

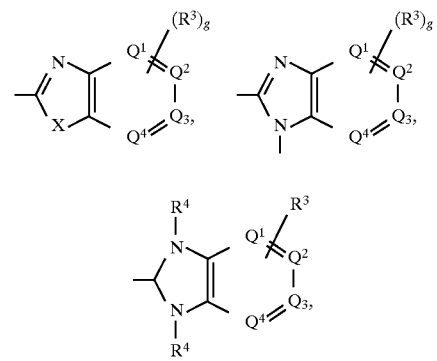

where Q$^1$, Q$^2$, Q$^3$, and Q$^4$ are CH

X is NR$^4$, g is an integer from 1 to 4;

each R$^3$ is independently selected from the group consisting of hydrogen, halogen, (C$_1$–C$_6$)alkyl, CH(R$^7$)CO$_2$R$^4$, (C$_1$–C$_6$)alkoxy, CO$_2$R$^4$, CONR$^4$R$^5$, CONHOH, CH$_2$NR$^4$R$^5$, NR$^4$R$^5$, nitro, hydroxy, CN, SO$_3$H, phenylalkyl having 1 to 4 carbons in the alkyl portion, SO$_2$NR$^4$R$^5$, N(SO$_2$R$^8$)$_2$ and NHSO$_2$R$^8$, where R$^4$ for each occurrence is independently selected from the group consisting of hydrogen, (C$_1$–C$_6$) alkyl, phenyl optionally substituted with (C$_1$–C$_4$) alkyl or halogen, CH(R$^7$)CO$_2$R$^6$, (C$_3$–C$_7$)cycloalkyl, phenylalkyl having 1 to 4 carbons in the alkyl portion and dialkylaminoalkyl having a total of 5 carbons in the dialkylamino portion and having 2 to 5 carbons in the alkyl portion where R$^5$ is as defined above, R$^5$ for each occurrence is independently selected from the group consisting of hydrogen, (C$_1$–C$_6$)alkyl, (C$_3$–C$_7$)cycloalkyl, phenylalkyl having 1 to 4 carbons in the alkyl portion, phenyl, pyridyl, pyrimidyl, thiazolyl and oxazolyl, or R$^4$ and R$^5$ are taken together with the nitrogen to which they are attached and form an optionally substituted saturated or unsaturated 5- or 6-membered ring, a saturated or unsaturated 6-membered heterocyclic ring containing two heteroatoms, or a quinoline ring optionally substituted with fluoro, where said optionally substituted saturated or unsaturated 5- or 6-membered ring may be mono- or di-substituted and each substituent is independently selected from the group consisting of alkyl having 1 to 4 carbons, $CO_2R^7$ wherein $R^7$ is as defined below, $CONH_2$, $CON(CH_3)_2$, oxo, hydroxy, $NH_2$ and $N(CH_3)_2$, and said saturated or unsaturated 6-membered heterocyclic ring containing two heteroatoms has the second heteroatom selected from the group consisting of O, S, NH, $NCH_3$, $NCOCH_3$ and $NCH_2Ph$;

$R^7$ for each occurrence is independently selected from the group consisting of hydrogen and $(C_1-C_4)$alkyl; and $R^8$ is selected from the group consisting of $(C_1-C_6)$ alkyl, $(C_3-C_7)$cycloalkyl, phenyl and phenylalkyl having 1 to 4 carbons in the alkyl portion.

2. A compound or a pharmaceutically acceptable salt thereof according to claim 1, wherein $R^1$ is selected from the group consisting of methyl and difluoromethyl;

$R^2$ is selected from the group consisting of $(C_3-C_7)$ cycloalkyl, $(C_6-C_8)$polycycloalkyl, phenylalkyl having 1 to 8 carbons in the alkyl portion and phenoxyalkyl having 2 to 6 carbons in the alkyl portion;

A is selected from the group consisting of a covalent bond, $(C_1-C_5)$alkylene and $(C_2-C_5)$alkenyl;

B is selected from the group consisting of a covalent bond, phenylene optionally substituted with $(C_1-C_4)$ alkoxy, $(C_1-C_5)$alkylene and $(C_2-C_5)$alkenyl;

Y is selected from the group consisting of a covalent bond, O and $NR^6$;

Z is selected from the group consisting of

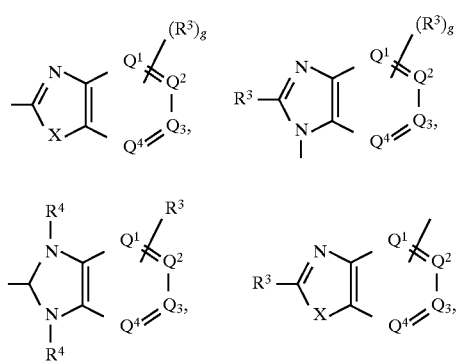

each $R^3$ is independently selected from the group consisting of hydrogen, halogen, $(C_1-C_6)$alkyl, $CH(R^7)$ $CO_2R^4$, $(C_1-C_6)$alkoxy, $CO_2R^4$, $CONR^4R^5$, nitro, hydroxy, $N(SO_2R^8)_2$ and $NHSO_2R^8$, where $R^4$ for each occurrence is independently selected from the group consisting of hydrogen and $(C_1-C_6)$ alkyl and $R^5$ is selected from the group consisting of hydrogen and $(C_1-C_6)$alkyl.

3. A compound or a pharmaceutically acceptable salt thereof according to claim 2, wherein $R^2$ is selected from the group consisting of $(C_3-C_7)$ cycloalkyl, $(C_6-C_9)$polycycloalkyl and phenylalkyl having 1 to 8 carbons in the alkyl portion;

A is selected from the group consisting of a covalent bond and methylene;

B is selected from the group consisting of a covalent bond, methylene and phenylene;

Y is selected from the group consisting of a covalent bond and O; and

Z is selected from the group consisting of

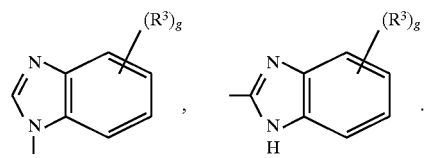

4. A compound or a pharmaceutically acceptable salt thereof according to claim 3, wherein A, B and Y are a covalent bond; and Z is selected from the group consisting of

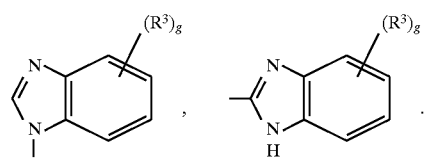

5. A compound or a pharmaceutically acceptable salt thereof according to claim 2 wherein A is methylene;

B is phenylene;

Y is O; and

Z is selected from the group consisting of

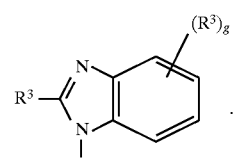

6. A pharmaceutical composition comprising an amount of a compound or a pharmaceutically acceptable salt thereof according to claim 1 and a pharmaceutically acceptable diluent or carrier.

7. A method of inhibiting phosphodiesterase IV in a mammal in need thereof which comprises administering to said mammal a phosphodiesterase IV inhibiting amount of a compound or a pharmaceutically acceptable salt thereof according to claim 1.

8. A method of treating an inflammatory condition in a mammal which comprises administering to said mammal an antiinflammatory amount of a compound or a pharmaceutically acceptable salt thereof according to claim 1.

9. A method of treating AIDS, asthma, arthritis, bronchitis, chronic obstructive pulmonary disease, psoriasis, allergic rhinitis, dermatitis or shock in a mammal which comprises administering to said mammal an effective amount of a compound or a pharmaceutically acceptable salt thereof according to claim 1.

* * * * *